(12) United States Patent
Raychaudhuri et al.

(10) Patent No.: US 8,906,860 B2
(45) Date of Patent: Dec. 9, 2014

(54) METHODS AND COMPOSITIONS INHIBITING TUMOR CELL PROLIFERATION

(71) Applicant: The Board of Trustees of the University of Illinois, Urbana, IL (US)

(72) Inventors: Pradip Raychaudhuri, Oak Park, IL (US); Alexander V. Lyubimov, Chicago, IL (US); Zebin Wang, Malden, MA (US); Robert Costa, Oak Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/840,092

(22) Filed: Mar. 15, 2013

(65) Prior Publication Data
US 2013/0196933 A1    Aug. 1, 2013

Related U.S. Application Data

(63) Continuation-in-part of application No. 13/652,390, filed on Oct. 15, 2012, now abandoned.

(60) Provisional application No. 61/547,671, filed on Oct. 14, 2011.

(51) Int. Cl.
*A61K 38/00* (2006.01)
*C07K 14/47* (2006.01)
*A61K 38/17* (2006.01)

(52) U.S. Cl.
CPC ............ *C07K 14/47* (2013.01); *A61K 38/1709* (2013.01); *C07K 2319/10* (2013.01); *C07K 14/4703* (2013.01); *C07K 14/4738* (2013.01); *C07K 2319/09* (2013.01)
USPC ........................................ 514/19.2

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 7,635,673 B2 * | 12/2009 | Costa et al. | 514/1.1 |
| 7,799,896 B2 * | 9/2010 | Costa et al. | 530/300 |
| 8,029,980 B2 | 10/2011 | Gartel et al. | |
| 2004/0109844 A1 | 6/2004 | Costa et al. | |

FOREIGN PATENT DOCUMENTS

| | | |
|---|---|---|
| EP | 036676 | 9/1981 |
| EP | 058481 | 8/1982 |
| EP | 088046 | 2/1983 |
| EP | 133988 | 3/1985 |
| EP | 143949 | 6/1985 |
| WO | 2004/100977 | 11/2004 |
| WO | 2007/109609 | * 9/2007 |
| WO | 2011/127297 | * 10/2011 |
| WO | 2011/133948 | 10/2011 |

OTHER PUBLICATIONS

Park et al., 2009, Embo J. 28: 2908-2918.
Pic et al., 2000, EMBO J 19: 3750-3761.
Polyalc et al., 1994, Genes Dev 8:9-22.
Radhakrishnan et al., 2006, Cancer Res, 66: 9731-9735.
Rausa et al., 2000, Mol Cell Biol 20:8264-8282.
Rausa et al., 2003, MoL Cell Biol. 23:437-449.
Raychaudhuri & Park, 2011, Cancer Res. 71: 4329-4333.
Rizo and Gierasch, 1992, Ann. Rev. Biochem. 61: 387.
Russell et al., 1996, MoL Carcinog. 15:183-189.
Samadani et al., 1996, MoL Cell. Biol. 16:6273-6284.
Sargent et al., 1996, Cancer Res. 56:2985-91.
Sengupta & Harris, 2005, Nat Rev Mol Cell Biol, 6: 44-55.
Sherr and McCormick, 2002, Cancer Cell 2:103-112.
Sidman et al., 1983, Biopolymers 22: 547-556.
Slagle et al., 1996, MoL Carcinog. 15:261-269.
Takeda et al., 2001, J Biol Chem 276:1993-1997.
Tamano et al., 1994, Carcinogenesis 15:1791-1798.
Tan et al., 2007, Mol Cell Biol. 27: 1007-1016.
Teh et al., 2002, Cancer Res. 62: 4773-80.
Veber and Freidinger, 1985, TINS p. 392.
Wang et al., 2002, J. Biol. Chem. 277:44310-44316.
Wang et al., 2011, Cancer Res, 71: 4292-4302.
Wang et al., 2002, Proc Natl Acad Sci USA 99:16881-16886.
Wang et al., 2005, Mol Cell Biol, 25: 10875-10894.
Weber et al., 2000, Mol Cell Biol 20:2517-2528.
Wender et al., 2000, Proc Natl Acad Sci USA 97:13003-13008.
Wohlschlegel et al., 2001, Mol Cell Biol 21:4868-4874.
Wolkow et al., 2000, Science 290: 147-150.
Wonsey & Follettie, 2005, Cancer Res. 65: 5181-5189.
Xie et al., 2010, Nucleic Acids Res. 38: 8027-8038.
Yao et al., 1997, J Biol. Chem. 272: 19827-19836.
Yao et al., 1998, Hum Gene Ther 9:1939-1950.
Ye et al., 1999, Mol Cell Biol, 19: 8570-8580.
Ye et al., 1997, Mol. Cell Biol. 17: 1626-1641.
Zerfass-Thome et al., 1997, Mol Cell Biol 17:407-415.
International Search Report and Written Opinion of International Application No. PCT/US2012/060304, dated Oct. 15, 2012 (mailed Mar. 5, 2013).
Adessi et al., 2002, Current Medicinal Chemistry 9:963-978).
Altieri, D. C., 2003, Oncogene, 22: 8581-8589.
Barsotti & Prives, 2009, Oncogene, 28: 4295-4305.
Barsyte et al., 2001, FASEB J. 15: 627-634.
Becker-Hapak et al., 2001, Methods 24:247-256.
Bhat et al. 2009, PLoS One, 4: e5592.
Biggs et al., 1999, Proc. Natl. Acad. Sci. USA 96: 7421-7426.
Brunet et al., 1999, Cell 96: 857-68.
Carr et al., 2010, Cancer Res, 70: 5054-5063.
Chawla et al., 2001, Science 294:1866-1870.

(Continued)

*Primary Examiner* — Sheela J Huff

(74) *Attorney, Agent, or Firm* — McDonnell Boehnen Hulbert & Berghoff LLP

(57) ABSTRACT

The invention provides agents, compositions, pharmaceutical compositions and method for inhibiting tumor cell proliferation by inhibiting FoxM1B activity, expression, or nuclear localization in a tumor cell.

2 Claims, 31 Drawing Sheets

(56) References Cited

OTHER PUBLICATIONS

Chen et al., 1997, Crit Rev Eukaryot Gene Expr 7:11-41.
Conzen et al., 2000, Mol Cell Biol 20:6008-6018.
Donehower, et al., 1992, Nature, 356: 215-221.
Eppstein et al., 1985, Proc. Natl. Acad. Sci. USA 82: 3688-3692.
Evans et al., 1987, J Med. Chem. 30: 1229.
Goldfarb et al., 1983, Environ. Health Perspect. 50:149-161.
Guo et al., 1999, J Biol. Chem. 274: 17184-17192.
Gusarova et al., 2007, J Clin Invest, 117: 99-111.
Hatayama et al., 1993, Carcinogenesis 14:537-538.
Hollenhorst et al., 2001, Genes Dev. 15: 2445-2456.
Honda et al., 1999, FASEB J. 13: 1385-1393.
Jacobs et al., 1999, Genes Dev, 13: 2678-2690.
Kalinichenko et al., Genes Dev. 2004, 18: 830-850.
Kalinina et al., 2003, Oncogene 22:6266-6276.
Kamijo et al., 1997, Cell 91:649-659.
Koranda et al., 2000, Nature 406: 94-98.
Korver et al., 1997, Nucleic Acids Res. 25: 1715-1719.
Korver et al., 1997, Genomics 46: 435-442.
Krupczak-Hollis et al., 2003, Hepatology 38:1552-1562.
Kumar et al., 2000, Curr. Biol. 10: 896-906.
Kunnath and Locker, 1983, Embo J2:317-324.
Kuribayashi, et al., 2011, Cell Cycle. 10: 2380-2389.
Kwok, et al., 2010, Mol Cancer Res, 8: 24-34.
Kwon et al., 2002, J Biol Chem 277:41417-41422.
Langer et al., 1981, J. Biomed Mater. Res. 15: 267-277.
Langer, 1982, Chem. Tech. 12: 98-105.
Laoukili et al., 2005, Nat Cell Biol. 7: 126-136.
Ledda-Columbano et al., 2002, Hepatology 36:1098-1105.
Lee et al., 2001, Curr. Biol. 11: 1950-1957.
Li et al., 2008 , J Biol Chem. 283: 16545-16553.
Lin et al., 1997, Science 278: 1319-1322.
Liu et al., Proc Natl Acad Sci USA, 107:18115-18120.
Lopes et al., 1997, J Biol Chem .272: 12893-12896.
Major et al., 2004, MoL CelL BioL 24:2649-2661.
Medema et al., 2000, Nature 404: 782-787.
Mirza et al., 2002, Oncogene, 21: 2613-2622.
Ogg et al., 1997, Nature 389: 994-999.
Pandit et al., 2009, Cell Cycle, 8: 3425-3427.
Pani et al., 1992, MoL Cell Biol. 12:3723-373245.
Paradis and Ruvkun, 1998, Genes Dev. 12: 2488-2498.
Park et aL, 2011, EMBO Mol Med, 3: 21-34.

\* cited by examiner

```
ggagcccgga gcccgccttc ggagctacgg cctaacggcg gcggcgactg cagtctggag 60
ggtccacact tgtgattctc aatggagagt gaaaacgcag attcataatg aaaactagcc 120
cccgtcggcc actgattctc aaaagacgga ggctgcccct tcctgttcaa aatgccccaa 180
gtgaaacatc agaggaggaa cctaagagat cccctgccca acaggagtct aatcaagcag 240
aggcctccaa ggaagtggca gagtccaact cttgcaagtt tccagctggg atcaagatta 300
ttaaccaccc caccatgccc aacacgcaag tagtggccat ccccaacaat gctaatattc 360
acagcatcat cacagcactg actgccaagg gaaaagagag tggcagtagt gggcccaaca 420
aattcatcct catcagctgt gggggagccc caactcagcc tccaggactc cggcctcaaa 480
cccaaaccag ctatgatgcc aaaaggacag aagtgaccct ggagaccttg ggaccaaaac 540

ctgcagctag ggatgtgaat cttcctagac cacctggagc cctttgcgag cagaaacggg 600
agacctgtgc agatggtgag gcagcaggct gcactatcaa caatagccta tccaacatcc 660
agtggcttcg aaagatgagt tctgatggac tgggctcccg cagcatcaag caagagatgg 720
aggaaaagga gaattgtcac ctggagcagc gacaggttaa ggttgaggag ccttcgagac 780
catcagcgtc ctggcagaac tctgtgtctg agcggccacc ctactcttac atggccatga 840
tacaattcgc catcaacagc actgagagga agcgcatgac tttgaaagac atctatacgt 900
ggattgagga ccactttccc tactttaagc acattgccaa gccaggctgg aagaactcca 960
tccgccacaa cctttccctg cacgacatgt ttgtccggga gacgtctgcc aatggcaagg 1020
tctccttctg gaccattcac cccagtgcca accgctactt gacattggac caggtgttta 1080
agcagcagaa acgaccgaat ccagagctcc gccggaacat gaccatcaaa accgaactcc 1140
ccctgggcgc acggcggaag atgaagccac tgctaccacg ggtcagctca tacctggtac 1200
ctatccagtt cccggtgaac cagtcactgg tgttgcagcc ctcggtgaag gtgccattgc 1260
ccctggcggc ttccctcatg agctcagagc ttgcccgcca tagcaagcga gtccgcattg 1320
cccccaaggt gctgctagct gaggagggga tagctcctct ttcttctgca ggaccaggga 1380
aagaggagaa actcctgttt ggagaagggt tttctccttt gcttccagtt cagactatca 1440
```

Figure 1A

```
aggaggaaga aatccagcct ggggaggaaa tgccacactt agcgagaccc atcaaagtgg 1500
agagccctcc cttggaagag tggccctccc cggccccatc tttcaaagag gaatcatctc 1560
actcctggga ggattcgtcc caatctccca ccccaagacc caagaagtcc tacagtgggc 1620
ttaggtcccc aacccggtgt gtctcggaaa tgcttgtgat tcaacacagg gagaggaggg 1680
agaggagccg gtctcggagg aaacagcatc tactgcctcc ctgtgtggat gagccggagc 1740
tgctcttctc agaggggccc agtacttccc gctgggccgc agagctcccg ttcccagcag 1800
actcctctga ccctgcctcc cagctcagct actcccagga agtgggagga cctttaaga  1860
cacccattaa ggaaacgctg cccatctcct ccaccccgag caaatctgtc ctccccagaa 1920
cccctgaatc ctggaggctc acgccccag ccaaagtagg gggactggat tcagcccag   1980
tacaaacctc ccagggtgcc tctgacccct tgcctgaccc cctggggctg atggatctca 2040
gcaccactcc cttgcaaagt gctccccccc ttgaatcacc gcaaaggctc ctcagttcag 2100
aaccttaga  cctcatctcc gtcccctttg gcaactcttc tccctcagat atagacgtcc 2160
ccaagccagg ctccccggag ccacaggttt ctggccttgc agccaatcgt tctctgacag 2220
aaggcctggt cctggacaca atgaatgaca gcctcagcaa gatcctgctg gacatcagct 2280
ttcctggcct ggacgaggac ccactgggcc ctgacaacat caactggtcc cagtttattc 2340
ctgagctaca gtagagccct gcccttgccc ctgtgctcaa gctgtccacc atcccgggca 2400
ctccaaggct cagtgcaccc caagcctctg agtgaggaca gcaggcaggg actgttctgc 2460
tcctcatagc tccctgctgc ctgattatgc aaaagtagca gtcacaccct agccactgct 2520
gggaccttgt gttccccaag agtatctgat tcctctgctg tccctgccag gagctgaagg 2580
gtgggaacaa caaaggcaat ggtgaaaaga gattaggaac ccccagcct gtttccattc  2640
tctgcccagc agtctcttac cttccctgat ctttgcaggg tggtccgtgt aaatagtata 2700
aattctccaa attatcctct aattataaat gtaagct                          2737
                                                         SEQ ID NO. 1
```

Figure 1B

```
MKTSPRRPLI LKRRRLPLPV QNAPSETSEE EPKRSPAQQE SNQAEASKEV AESNSCKFPA    60
GIKIINHPTM PNTQVVAIPN NANIHSIITA LTAKGKESGS SGPNKFILIS CGGAPTQPPG   120
LRPQTQTSYD AKRTEVTLET LGPKPAARDV NLPRPPGALC EQKRETCADG EAAGCTINNS   180
LSNIQWLRKM SSDGLGSRSI KQEMEEKENC HLEQRQVKVE EPSRPSASWQ NSVSERPPYS   240
YMAMIQFAIN STERKRMTLK DIYTWIEDHF PYFKHIAKPG WKNSIRHNLS LHDMFVRETS   300
ANGKVSFWTI HPSANRYLTL DQVFKQQKRP NPELRRNMTI KTELPLGARR KMKPLLPRVS   360
SYLVPIQFPV NQSLVLQPSV KVPLPLAASL MSSELARHSK RVRIAPKVLL AEEGIAPLSS   420
AGPGKEEKLL FGEGFSPLLP VQTIKEEEIQ PGEEMPHLAR PIKVESPPLE EWPSPAPSFK   480
EESSHSWEDS SQSPTPRPKK SYSGLRSPTR CVSEMLVIQH RERRERSRSR RKQHLLPPCV   540
DEPELLFSEG PSTSRWAAEL PFPADSSDPA SQLSYSQEVG GPFKTPIKET LPISSTPSKS   600
VLPRTPESWR LTPPAKVGGL DFSPVQTSQG ASDPLPDPLG LMDLSTTPLQ SAPPLESPQR   660
LLSSEPLDLI SVPFGNSSPS DIDVPKPGSP EPQVSGLAAN RSLTEGLVLD TMNDSLSKIL   720
LDISFPGLDE DPLGPDNINW SQFIPELQ                                     748
                                                           SEQ ID NO. 2
```

Figure 1C

SEQUENCE LISTING

<160> NUMBER OF SEQ ID NOS: 21

<210> SEQ ID NO 1
<211> LENGTH: 2737
<212> TYPE: DNA
<213> ORGANISM: Homo sapiens

<400> SEQUENCE: 1
ggagcccgga gcccgccttc ggagctacgg cctaacggcg gcggcgactg cagtctggag        60

| | |
|---|---|
| ggtccacact tgtgattctc aatggagagt gaaaacgcag attcataatg aaaactagcc | 120 |
| cccgtcggcc actgattctc aaaagacgga ggctgcccct tcctgttcaa aatgccccaa | 180 |
| gtgaaacatc agaggaggaa cctaagagat cccctgccca acaggagtct aatcaagcag | 240 |
| aggcctccaa ggaagtggca gagtccaact cttgcaagtt tccagctggg atcaagatta | 300 |
| ttaaccaccc caccatgccc aacacgcaag tagtggccat ccccaacaat gctaatattc | 360 |
| acagcatcat cacagcactg actgccaagg gaaaagagag tggcagtagt gggcccaaca | 420 |
| aattcatcct catcagctgt gggggagccc caactcagcc tccaggactc cggcctcaaa | 480 |
| cccaaaccag ctatgatgcc aaaaggacag aagtgaccct ggagaccttg ggaccaaaac | 540 |
| ctgcagctag ggatgtgaat cttcctagac cacctggagc cctttgcgag cagaaacggg | 600 |
| agacctgtgc agatggtgag gcagcaggct gcactatcaa caatagccta tccaacatcc | 660 |
| agtggcttcg aaagatgagt tctgatggac tgggctcccg cagcatcaag caagagatgg | 720 |
| aggaaaagga gaattgtcac ctggagcagc gacaggttaa ggttgaggag ccttcgagac | 780 |
| catcagcgtc ctggcagaac tctgtgtctg agcggccacc ctactcttac atggccatga | 840 |
| tacaattcgc catcaacagc actgagagga agcgcatgac tttgaaagac atctatacgt | 900 |
| ggattgagga ccactttccc tactttaagc acattgccaa gccaggctgg aagaactcca | 960 |
| tccgccacaa cctttccctg cacgacatgt tgtccgggga gacgtctgcc aatggcaagg | 1020 |
| tctccttctg gaccattcac cccagtgcca accgctactt gacattggac caggtgttta | 1080 |
| agcagcagaa acgaccgaat ccagagctcc gccggaacat gaccatcaaa accgaactcc | 1140 |
| ccctgggcgc acgcggaag atgaagccac tgctaccacg ggtcagctca tacctggtac | 1200 |
| ctatccagtt cccggtgaac cagtcactgg tgttgcagcc ctcggtgaag gtgccattgc | 1260 |
| ccctggcggc ttccctcatg agctcagagc ttgcccgcca tagcaagcga gtccgcattg | 1320 |
| cccccaaggt gctgctagct gaggagggga tagctcctct ttcttctgca ggaccaggga | 1380 |
| aagaggagaa actcctgttt ggagaagggt tttctccttt gcttccagtt cagactatca | 1440 |
| aggaggaaga aatccagcct ggggaggaaa tgccacactt agcgagaccc atcaaagtgg | 1500 |
| agagccctcc cttggaagag tggccctccc cggccccatc tttcaaagag gaatcatctc | 1560 |
| actcctggga ggattcgtcc caatctccca ccccaagacc caagaagtcc tacagtgggc | 1620 |
| ttaggtcccc aacccggtgt gtctcggaaa tgcttgtgat tcaacacagg gagaggaggg | 1680 |
| agaggagccg gtctcggagg aaacagcatc tactgcctcc ctgtgtggat gagccggagc | 1740 |
| tgctcttctc agaggggccc agtacttccc gctgggccgc agagctcccg ttcccagcag | 1800 |
| actcctctga ccctgcctcc cagctcagct actcccagga agtgggagga ccttttaaga | 1860 |
| cacccattaa ggaaacgctg cccatctcct ccaccccgag caaatctgtc ctccccagaa | 1920 |
| cccctgaatc ctggaggctc acgccccag ccaaagtagg gggactggat ttcagcccag | 1980 |
| tacaaacctc ccagggtgcc tctgacccct tgcctgaccc cctggggctg atggatctca | 2040 |
| gcaccactcc cttgcaaagt gctcccccccc ttgaatcacc gcaaaggctc ctcagttcag | 2100 |
| aacccttaga cctcatctcc gtcccctttg gcaactcttc tccctcagat atagacgtcc | 2160 |
| ccaagccagg ctccccggag ccacaggttt ctggccttgc agccaatcgt tctctgacag | 2220 |
| aaggcctggt cctggacaca atgaatgaca gcctcagcaa gatcctgctg gacatcagct | 2280 |
| ttcctggcct ggacgaggac ccactggggc ctgacaacat caactggtcc cagtttattc | 2340 |
| ctgagctaca gtagagccct gcccttgccc ctgtgctcaa gctgtccacc atcccgggca | 2400 |
| ctccaaggct cagtgcaccc caagcctctg agtgaggaca gcaggcaggg actgttctgc | 2460 |

-continued

```
tcctcatagc tccctgctgc ctgattatgc aaaagtagca gtcacaccct agccactgct    2520
gggaccttgt gttccccaag agtatctgat tcctctgctg tccctgccag gagctgaagg    2580
gtgggaacaa caaaggcaat ggtgaaaaga gattaggaac cccccagcct gtttccattc    2640
tctgcccagc agtctcttac cttccctgat ctttgcaggg tggtccgtgt aaatagtata    2700
aattctccaa attatcctct aattataaat gtaagct                             2737
```

```
<210> SEQ ID NO 2
<211> LENGTH: 748
<212> TYPE: PRT
<213> ORGANISM: Homo sapiens

<400> SEQUENCE: 2
```

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320
```

-continued

```
Asp Gln Val Phe Lys Gln Gln Lys Arg Pro Asn Pro Glu Leu Arg Arg
            325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
            405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
            435                 440                 445

Ile Gln Pro Gly Glu Glu Met Pro His Leu Ala Arg Pro Ile Lys Val
    450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
            515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
            565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
            595                 600                 605

Trp Arg Leu Thr Pro Pro Ala Lys Val Gly Gly Leu Asp Phe Ser Pro
            610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
            645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
            675                 680                 685

Ser Pro Glu Pro Gln Val Ser Gly Leu Ala Ala Asn Arg Ser Leu Thr
            690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
```

```
                        740             745

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid

<400> SEQUENCE: 3

Leu Xaa Leu Xaa Xaa Leu
1               5

<210> SEQ ID NO 4
<211> LENGTH: 66
<212> TYPE: DNA
<213> ORGANISM: Artificial Sequence
<220> FEATURE:
<223> OTHER INFORMATION: Synthetic, 5' EcoR1 T-epitope tagged FoxM1B
      primer

<400> SEQUENCE: 4
gcggaattca ccatggctag catgactggt ggacagcaaa tgggttggca gaactctgtg    60
tctgag                                                               66

<210> SEQ ID NO 5
<211> LENGTH: 18
<212> TYPE: DNA
<213> ORGANISM: Artificial Sequence
<220> FEATURE:
<223> OTHER INFORMATION: Synthetic; antisense primer for CMV expression
      vector SV-40 poly A region

<400> SEQUENCE: 5
gtttgtccaa ttatgtca                                                  18

<210> SEQ ID NO 6
<211> LENGTH: 12
<212> TYPE: DNA
<213> ORGANISM: Artificial Sequence
<220> FEATURE:
<223> OTHER INFORMATION: FoxM1B/FoxA binding site

<400> SEQUENCE: 6
tttgtttgtt tg                                                        12

<210> SEQ ID NO 7
<211> LENGTH: 6
<212> TYPE: RNA
<213> ORGANISM: Artificial Sequence
<220> FEATURE:
<223> OTHER INFORMATION: Synthetic; transcription termination signal

<400> SEQUENCE: 7 aauaaa                                                                6

<210> SEQ ID NO 8
<211> LENGTH: 82
<212> TYPE: PRT
```

<213> ORGANISM: Homo sapiens

<400> SEQUENCE: 8

Pro Phe Lys Thr Pro Ile Lys Glu Thr Leu Pro Ile Ser Ser Thr Pro
1               5                   10                  15

Ser Lys Ser Val Leu Pro Arg Thr Pro Glu Ser Trp Arg Leu Thr Pro
            20                  25                  30

Pro Ala Lys Val Gly Gly Leu Asp Thr Phe Ser Pro Val Gln Thr Ser
        35                  40                  45

Gln Gly Ala Ser Asp Pro Leu Pro Asp Pro Leu Gly Leu Met Asp Leu
    50                  55                  60

Ser Thr Thr Pro Leu Gln Ser Ala Pro Pro Leu Glu Ser Pro Gln Arg
65                  70                  75                  80

Leu Leu

<210> SEQ ID NO 9
<211> LENGTH: 28
<212> TYPE: PRT
<213> ORGANISM: Artificial Sequence
<220> FEATURE:
<223> OTHER INFORMATION: Synthetic, LXLXXL motif from FoxM1B amino acid
      residue 635 to 662
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (11)..(14)
<223> OTHER INFORMATION: Xaa is any amino acid
<220> FEATURE:
<221> NAME/KEY: MISC_FEATURE
<222> LOCATION: (16)..(20)
<223> OTHER INFORMATION: Xaa is any amino acid
<220> FEATURE:
<221> NAME/KEY: MISC_FEATURE
<222> LOCATION: (22)..(26)
<223> OTHER INFORMATION: Xaa is any amino acid

<400> SEQUENCE: 9

Leu Xaa Xaa Xaa Leu Xaa Leu Xaa Xaa Leu Xaa Xaa Xaa Xaa Leu Xaa
1               5                   10                  15

Xaa Xaa Xaa Xaa Leu Xaa Xaa Xaa Xaa Xaa Leu Leu
            20                  25

<210> SEQ ID NO 10
<211> LENGTH: 28
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Xaa is D-Arginine

<400> SEQUENCE: 10

Xaa Xaa Xaa Xaa Xaa Xaa Xaa Xaa Xaa Lys Phe Val Arg Ser Arg Arg
1               5                   10                  15

Pro Arg Thr Ala Ser Cys Ala Leu Ala Phe Val Asn
            20                  25

<210> SEQ ID NO 11
<211> LENGTH: 19
<212> TYPE: PRT
<213> ORGANISM: Mus musculus

<400> SEQUENCE: 11

Lys Phe Val Arg Ser Arg Arg Pro Arg Thr Ala Ser Cys Ala Leu Ala
1               5                   10                  15

Phe Val Asn

<210> SEQ ID NO 12
<211> LENGTH: 30
<212> TYPE: PRT
<213> ORGANISM: Mus musculus

<400> SEQUENCE: 12

Lys Phe Val Arg Ser Arg Arg Pro Arg Thr Ala Ser Cys Ala Leu Ala
1               5                   10                  15

Phe Val Asn Met Leu Leu Arg Leu Glu Arg Ile Leu Arg Arg
            20                  25                  30

<210> SEQ ID NO 13
<211> LENGTH: 13
<212> TYPE: PRT
<213> ORGANISM: Human immunodeficiency virus

<400> SEQUENCE: 13

Met Gly Tyr Gly Arg Lys Lys Arg Arg Gln Arg Arg Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(9)
<223> OTHER INFORMATION: Xaa is D-Arginine

<400> SEQUENCE: 14

Xaa Xaa Xaa Xaa Xaa Xaa Xaa Xaa Xaa
1               5

<210> SEQ ID NO 15
<211> LENGTH: 169
<212> TYPE: PRT
<213> ORGANISM: Mus musculus

<400> SEQUENCE: 15

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
            20                  25                  30

Pro Arg Thr Ala Ser Cys Ala Leu Ala Phe Val Asn Met Leu Leu Arg
        35                  40                  45

Leu Glu Arg Ile Leu Arg Arg Gly Pro His Arg Asn Pro Gly Pro Gly
    50                  55                  60

Asp Asp Asp Gly Gln Arg Ser Ser Ser Ser Ala Gln Leu Arg
65                  70                  75                  80

```
Cys Arg Phe Glu Leu Arg Gly Pro His Tyr Leu Leu Pro Pro Gly Asp
             85                  90                  95

Arg Arg Ser Ala Gly Arg Leu Pro Gly His Ala Gly Ala Ala Arg
        100                 105                 110

Val Arg Gly Ser Ala Gly Cys Ala Arg Cys Leu Gly Ser Pro Ala Ala
        115                 120                 125

Arg Leu Gly Pro Arg Ala Gly Thr Ser Arg His Arg Ala Ile Phe Ala
    130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

<210> SEQ ID NO 16
<211> LENGTH: 19
<212> TYPE: PRT
<213> ORGANISM: Mus musculus

<400> SEQUENCE: 16

Lys Phe Val Arg Ser Arg Arg Pro Arg Thr Ala Ser Cys Ala Leu Ala
1               5                   10                  15

Phe Val Asn

<210> SEQ ID NO 17
<211> LENGTH: 13
<212> TYPE: PRT
<213> ORGANISM: Human immunodeficiency virus

<400> SEQUENCE: 17

Met Gly Tyr Gly Arg Lys Lys Arg Arg Gln Arg Arg
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(9)
<223> OTHER INFORMATION: Xaa is D-Arginine

<400> SEQUENCE: 18

Xaa Xaa Xaa Xaa Xaa Xaa Xaa Xaa Xaa
1               5

<210> SEQ ID NO 19
<211> LENGTH: 28
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Xaa is D-Arginine

<400> SEQUENCE: 19

Xaa Xaa Xaa Xaa Xaa Xaa Xaa Xaa Xaa Lys Phe Val Arg Ser Arg Arg
1               5                   10                  15

Pro Arg Thr Ala Ser Cys Ala Leu Ala Phe Val Asn
            20                  25

<210> SEQ ID NO 20
```

-continued

```
<211> LENGTH: 131
<212> TYPE: PRT
<213> ORGANISM: Homo sapiens

<400> SEQUENCE: 20

Met Val Arg Arg Phe Leu Val Thr Leu Arg Ile Arg Arg Ala Cys Gly
1               5                   10                  15

Pro Pro Arg Val Arg Val Phe Val Val His Ile Pro Arg Leu Thr Gly
            20                  25                  30

Glu Trp Ala Ala Pro Gly Ala Pro Ala Ala Val Ala Leu Val Leu Met
        35                  40                  45

Leu Leu Arg Ser Gln Arg Leu Gly Gln Pro Leu Pro Arg Arg Pro Gly
    50                  55                  60

His Asp Asp Gly Gln Arg Pro Ser Gly Gly Ala Ala Ala Pro Arg
65                  70                  75                  80

Arg Gly Ala Gln Leu Arg Arg Pro Arg His Ser His Pro Thr Arg Ala
                85                  90                  95

Arg Arg Cys Pro Gly Gly Leu Pro Gly His Ala Gly Gly Ala Ala Pro
            100                 105                 110

Gly Arg Gly Ala Ala Gly Arg Ala Arg Cys Leu Gly Pro Ser Ala Arg
        115                 120                 125

Gly Pro Gly
    130

<210> SEQ ID NO 21
<211> LENGTH: 17
<212> TYPE: PRT
<213> ORGANISM: Artificial Sequence
<220> FEATURE:
<223> OTHER INFORMATION: Synthetic; primer
<220> FEATURE:
<221> NAME/KEY: MISC_FEATURE
<222> LOCATION: (1)..(9)
<223> OTHER INFORMATION: Xaa is D-Arginine

<400> SEQUENCE: 21

Xaa Xaa Xaa Xaa Xaa Xaa Xaa Xaa Xaa Ser Cys Ala Leu Ala Phe Val
1               5                   10                  15

Asn
```

METHODS AND COMPOSITIONS INHIBITING TUMOR CELL PROLIFERATION

This application is a continuation-in-part of U.S. patent application Ser. No. 13/652,390 filed on Oct. 15, 2012, which claims priority to U.S. Provisional Pat. App. No. 61/547,671, filed on Oct. 14, 2011, each of said prior applications being fully incorporated by reference herein for all purposes.

This invention was made with government support under AG21842-02 awarded by the National Institute on Aging, under CA124488 awarded by the National Cancer Insititue and under DK54687-06 awarded by the National Institute of Diabetes and Digestive and Kidney Diseases. The government has certain rights in the invention.

BACKGROUND OF THE INVENTION

1. Field of the Invention

The invention relates to methods of inhibiting tumor cell proliferation by inhibiting FoxM1B activity. Specifically, the invention relates to methods and compositions for inhibiting tumor cell proliferation by inhibiting FoxM1B activity, expression, or nuclear localization in a tumor cell.

2. Background of the Related Art

The Forkhead box transcription factors have been implicated in regulating cellular longevity and proliferative capacity. Such studies include a finding of increased longevity in *C. elegans* bearing a mutant daf-2 gene, which encodes the worm homolog of the insulin/Insulin-like Growth Factor 1 (IGF1) receptor (Lin et al., 1997, *Science* 278: 1319-1322; Ogg et al., 1997, *Nature* 389: 994-999). Disruption of the daf-2 gene abolishes insulin-mediated activation of the phosphatidylinositol 3-kinase (PI3K)-protein kinase B/Akt (Akt) signal transduction pathway and prevents inhibition of the forkhead transcription factor daf-16 (corresponding to mammalian homologs FoxO1 or Fkhr) (Paradis and Ruvkun, 1998, *Genes Dev.* 12: 2488-2498). Activation of the PI3K/Akt pathway phosphorylates the C-terminus of the Daf-16 (FoxO1; Fkhr) gene product and mediates its nuclear export into the cytoplasm, thus preventing FoxO1 transcriptional activation of target genes (Biggs et al., 1999, *Proc. Natl. Acad. Sci. USA* 96: 7421-7426; Brunet et al., 1999, *Cell* 96: 857-68; Guo et al., 1999, *J. Biol. Chem.* 274: 17184-17192).

Studies of Daf-2⁻ *C. elegans* mutants have demonstrated that Daf-16 stimulates expression of genes that limit oxidative stress (Barsyte et al., 2001, *FASEB J.* 15: 627-634; Honda et al., 1999, *FASEB J.* 13: 1385-1393; Wolkow et al., 2000, *Science* 290: 147-150) and that the mammalian FoxO1 gene could functionally replace the Daf-16 gene in *C. elegans* (Lee et al., 2001, *Curr. Biol.* 11: 1950-1957). In proliferating mammalian cells, the PI3K/Akt signal transduction pathway is essential for G1 to S-phase progression because it prevents transcriptional activity of the FoxO1 and FoxO3 proteins, which stimulate expression of the CDK inhibitor p27$^{kip1}$ gene (Medema et al., 2000, *Nature* 404: 782-787). Moreover, genetic studies in budding yeast demonstrated that forkhead Fkh1 and Fkh2 proteins are components of a transcription factor complex that regulates expression of genes critical for progression into mitosis (Hollenhorst et al., 2001, *Genes Dev.* 15: 2445-2456; Koranda et al., 2000, *Nature* 406: 94-98; Kumar et al., 2000, *Curr. Biol.* 10: 896-906; Pic et al., 2000, *EMBO J.* 19: 3750-3761).

Forkhead Box M1B (FoxM1B) transcription factor (also known as Trident and HFH-11B) is a proliferation-specific transcription factor that shares 39% amino acid homology with the HNF-3 winged helix DNA binding domain. The molecule also contains a potent C-terminal transcriptional activation domain that possesses several phosphorylation sites for M-phase specific kinases as well as PEST sequences that mediate rapid protein degradation (Korver et al., 1997, *Nucleic Acids Res.* 25: 1715-1719; Korver et al., 1997, *Genomics* 46: 435-442; Yao et al., 1997, *J. Biol. Chem.* 272: 19827-19836; Ye et al., 1997, *Mol. Cell Biol.* 17: 1626-1641).

In situ hybridization studies have shown that FoxM1B is expressed in embryonic liver, intestine, lung, and renal pelvis (Ye et al., 1997, *Mol. Cell Biol.* 17: 1626-1641). In adult tissue, however, FoxM1B is not expressed in postmitotic, differentiated cells of the liver and lung, although it is expressed in proliferating cells of the thymus, testis, small intestine, and colon (Id). FoxM1B expression is reactivated in the liver prior to hepatocyte DNA replication following regeneration induced by partial hepatectomy (Id).

FoxM1B is expressed in several tumor-derived epithelial cell lines and its expression is induced by serum prior to the $G_1$/S transition (Korver et al., 1997, *Nucleic Acids Res.* 25: 1715-1719; Korver et al., 1997, *Genomics* 46: 435-442; Yao et al., 1997, *J. Biol. Chem.* 272: 19827-19836; Ye et al., 1997, *Mol. Cell Biol.* 17: 1626-1641). Consistent with the role of FoxM1B in cell cycle progression, elevated FoxM1B levels are found in numerous actively-proliferating tumor cell lines (Korver et al., 1997, *Nucleic Acids Res.* 25: 1715-1719; Yao et al., 1997, *J. Biol. Chem.* 272: 19827-36; Ye et al., 1997, *Mol. Cell Biol.* 17: 1626-1641). Increased nuclear staining of FoxM1B was also found in human basal cell carcinomas (Teh et al., 2002, *Cancer Res.* 62: 4773-80), suggesting that FoxM1B is required for cellular proliferation in human cancers.

FOXM1B facilitates development of cancers in several ways. First, it transcriptionally activates genes involved in cell-proliferation, and promotes progression through G1-S and G2-M phases of the cell cycle (Wang, et al., 2005, *Mol Cell Biol*, 25: 10875-10894; Laoukili et al., 2005, *Nat Cell Biol.* 7: 126-136). It stimulates expression of DNA repair genes, ensuring chromosome stability (Tan et al., 2007, *Mol Cell Biol.* 27: 1007-1016; Wonsey & Follettie, 2005, *Cancer Res.* 65: 5181-5189). In addition, FoxM1 has been implicated in alleviating oxidative stress in tumor cells by activating ROS scavenger proteins (Park et al., 2009, *Embo J.* 28: 2908-2918) and mediating resistance to Herceptin and paclitaxel (Carr et al., 2010, *Cancer Res*, 70: 5054-5063; Kwok, et al., 2010, *Mol Cancer Res*, 8: 24-34). One study in a mouse hepatocellular carcinoma (HCC) model demonstrated that FOXM1 also functions as a potent activator of tumor metastasis through promoting the epithelial-to-mesenchymal transition (EMT), increased motility of the tumor cells, and establishment of pre-metastatic niches in the distal target organ (Park et al., 2011, *EMBO Mol Med*, 3: 21-34; Raychaudhuri & Park, 2011, *Cancer Res.* 71: 4329-4333). Two studies in neuroblastoma and embryonic carcinoma cells indicated a role of FOXM1 in the maintenance of the undifferentiated state of the tumor cells by activating pluripotency-associated genes (Wang et al., 2011, *Cancer Res*, 71: 4292-4302; Xie et al., 2010, *Nucleic Acids Res.* 38: 8027-8038).

FOXM1 is a proliferative-specific transcriptional factor whose expression is unique to the proliferating cells (Korver et al., 1997, *Nucleic Acids Res*, 25: 1715-1719; Ye et al., 1999, *Mol Cell Biol*, 19: 8570-8580). Several strategies have been developed to target FoxM1 in cancer cells. Based on the fact that FoxM1 is an inhibitory target of mouse ARF tumor suppressor, a cell penetrating ARF 26-44 peptide which consists of 9 N-terminal D-arginine (D69 Arg) residues and amino acid residues 26-44 of the mouse ARF protein was synthesized (Kalinichenko et al., *Genes Dev.* 2004, 18: 830-

850). The ARF 26-44 peptide, which inhibits FOXM1 by sequestering it to the nucleolus, was effective in diminishing tumor size in HCC by reducing tumor cell proliferation and inducing apoptosis (Gusarova et al., 2007, *J Clin Invest*, 117: 99-111). That ARF peptide also effectively prevented pulmonary metastasis of HCC cells (Park et al., 2011, *EMBO Mol Med.* 3: 21-34). In addition, thiazole antibiotics have been shown to down-regulate FOXM1 and induce apoptosis in various cancer cells (Bhat et al., 2009, PLoS One, 4: e5592; Radhakrishnan et al., 2006, *Cancer Res*, 66: 9731-9735).

SUMMARY OF THE INVENTION

The invention provides methods of inhibiting proliferation of a tumor cell, comprising the step of inhibiting FoxM1B activity in the tumor cell. The methods of the invention can be accomplished by regulating FoxM1B activity through any of the mechanisms as described herein or described in co-owned U.S. patent application Ser. No. 12/871,560 and co-owned U.S. Pat. Nos. 7,799,896 and 7,635,673. The disclosures of U.S. patent application Ser. No. 12/871,560 and U.S. Pat. Nos. 7,799,896 and 7,635,673 are herein incorporated by reference in their entireties.

In one aspect of the invention, cellular FoxM1B activity is inhibited by causing FoxM1B protein to localize in the tumor cell cytoplasm, to localize to the nucleolus of the tumor cell nucleus, preventing or inhibiting translocation of FoxM1B to the cell nucleus, or any combination of these effects. Causing FoxM1B protein to localize in the cytoplasm can be accomplished, for example, by contacting a cell with a compound that causes FoxM1B to translocate from the nucleus to the cytoplasm, or that sequesters FoxM1B in the cytoplasm and prevents FoxM1B from translocating from the cytoplasm to the nucleus. Causing FoxM1B protein to localize in the nucleolus of the cell nucleus can be achieved when FoxM1B protein interacts with the tumor suppressor $p19^{ARF}$ protein or a peptide containing the $p19^{ARF}$ sequences 26-44 or compounds that mimic $p19^{ARF}$ function. Such compounds can be identified using screening methods of the invention as described herein.

In another aspect, FoxM1B activity can be inhibited by contacting a cell, preferably a tumor cell, with a peptide having an amino acid sequence of the $p19^{ARF}$ tumor suppressor protein as set forth in SEQ ID NO: 10 (rrrrrrrrrKFVRSR-RPRTASCALAFVN; referred to herein as the (D-Arg)$_9$-$p19^{ARF}$ 26-44 peptide), SEQ ID NO: 11 (KFVRSRRPRTASCALAFVN; referred to herein as the $p19^{ARF}$ 26-44 peptide), or SEQ ID NO: 12 (KFVRSR-RPRTASCALAFVNMLLRLERIL RR; referred to herein as the $p19^{ARF}$ 26-55 peptide).

In another aspect, the invention provides a modified polypeptide that inhibits FoxM1B activity in a tumor cell. In a preferred embodiment, the polypeptide comprises a $p19^{ARF}$ peptide fragment comprising amino acid residues KFVRSR-RPRTASCALAFVN (SEQ ID NO:16), and an HIV Tat peptide of SEQ ID NO:17. In another embodiment, the polypeptide comprises a $p19^{ARF}$ peptide fragment comprising amino acid residues KFVRSRRPRTASCALAFVN (SEQ ID NO:16), and a nine-D-Arg peptide of SEQ ID NO:18. In some embodiments, the nine-D-Arg peptide of SEQ ID NO:18 or the HIV Tat peptide of SEQ ID NO:17 is covalently linked to the N-terminus of the $p19^{ARF}$ peptide fragment. In other embodiments, the polypeptide has the amino acid sequence of SEQ ID NO:19.

In another aspect, the invention provides a modified polypeptide that inhibits FoxM1B activity in a tumor cell wherein the polypeptide is modified at the N-terminus, at the C-terminus, or at both the N terminus and the C terminus. In certain embodiments, the polypeptide is modified by acetylation. In other embodiments, the polypeptide is modified by amidation. In still other embodiments, the polypeptide is modified by both acetylation and amidation. In particular embodiments the polypeptide is simultaneously modified at the N and the C termini.

The methods of the invention can be used to inhibit growth of any tumor cell that expresses FoxM1B protein or that is derived from a cell that expressed FoxM1B protein. A cell that expresses FoxM1B protein can be, in non-limiting example, a cell from an aging individual, wherein expression of FoxM1B protein is diminished as a result of aging. In a particular aspect, the methods of the invention can be used to inhibit tumor cell growth in vitro (i.e. under cell culture conditions) or in vivo (i.e. in a live animal). In other aspects, the methods of the invention can be used to inhibit growth of tumor cells that are derived from benign or malignant tumors. In a particular aspect, the tumor cells are of epithelial cell origin, for example, from liver, lung, skin, intestine (small intestine or colon), colorectal, spleen, prostate, breast, brain, pancreas, or thymus cells. The tumor cells can also be of mesoderm cell origin, for example, from liver, lung, skin, intestine (small intestine or colon), colorectal, spleen, prostate, breast, brain, pancreas, bone marrow or thymus cells. In other embodiments of the invention the tumor cells have a loss-of-function p53 mutation.

The invention also provides methods for inhibiting tumor growth in an animal comprising administering to an animal, bearing at least one tumor cell present in its body, a therapeutically effective amount of a FoxM1B inhibitor for a therapeutically effective period of time. In another aspect, the FoxM1B inhibitor can be a compound that inhibits FoxM1B activity. In yet another aspect, the FoxM1B inhibitor can be a peptide having an amino acid sequence as set forth in SEQ ID NO: 10, SEQ ID NO: 11, or SEQ ID NO: 12, for a therapeutically effective period of time. In other aspects, the FoxM1B inhibitor can be a compound comprising a $p19^{ARF}$ peptide fragment comprising amino acid residues KFVRSR-RPRTASCALAFVN (SEQ ID NO:16), and an HIV Tat peptide of SEQ ID NO:17. In other embodiments, the FoxM1B inhibitor can be a compound comprising a $p19^{ARF}$ peptide fragment comprising amino acid residues KFVRSR-RPRTASCALAFVN (SEQ ID NO:16), and a nine-D-Arg peptide of SEQ ID NO:18. In yet other embodiments, FoxM1B inhibitor can be a compound wherein the nine-D-Arg peptide of SEQ ID NO:18 or the HIV Tat peptide of SEQ ID NO:17 is covalently linked to the N-terminus of the $p19^{ARF}$ peptide fragment. In other embodiments, the FoxM1B inhibitor can be a compound having the amino acid sequence of SEQ ID NO:19.

In another aspect, the FoxM1B inhibitor is a compound modified at the N-terminus, at the C-terminus, or at both the N terminus and the C terminus. In certain embodiments, the FoxM1B inhibitor is a compound modified by acetylation. In other embodiments, the FoxM1B inhibitor is a compound modified by amidation. In still other embodiments, the FoxM1B inhibitor is a compound modified by both acetylation and amidation.

In additional aspects, a combination of peptides that inhibit FoxM1B activity can be administered to the animal. For example, peptides having an amino acid sequence as set forth in SEQ ID NO: 10 can be administered with peptides having an amino acid sequence as set forth in SEQ ID NO: 11 and/or SEQ ID NO: 12. One of skill in the art will recognize that any combination of these peptides can be administered to the animal bearing at least one tumor cell in its body.

The invention also provides pharmaceutical compositions comprising a peptide having an amino acid sequence as set forth in SEQ ID NO: 10, SEQ ID NO: 11, or SEQ ID NO: 12 or therapeutically-effective mixture thereof. In certain aspects, pharmaceutical compositions of the invention are useful for inhibiting tumor cell growth in an animal by inhibiting FoxM1B activity in the tumor cell. In other embodiments, the pharmaceutical composition comprises a modified polypeptide that inhibits FoxM1B activity in a tumor cell.

Specific preferred embodiments of the invention will become evident from the following more detailed description of certain preferred embodiments and the claims.

DETAILED DESCRIPTION OF THE DRAWINGS

FIGS. 1A and 1B depict a human FoxM1B cDNA comprising a deletion of the terminal 972 nucleotides at the 3' end (SEQ ID NO: 1).

FIG. 1C depicts a human FoxM1B protein sequence (SEQ ID NO: 2) encoded by the nucleotide sequence as set forth in SEQ ID NO: 1.

FIGS. 4A and 4B show RNase protection assays (RPA) with a FoxM1B probe after infection of human osteoblastoma U2Os cells with AdFoxM1B AS.

Figure 5:
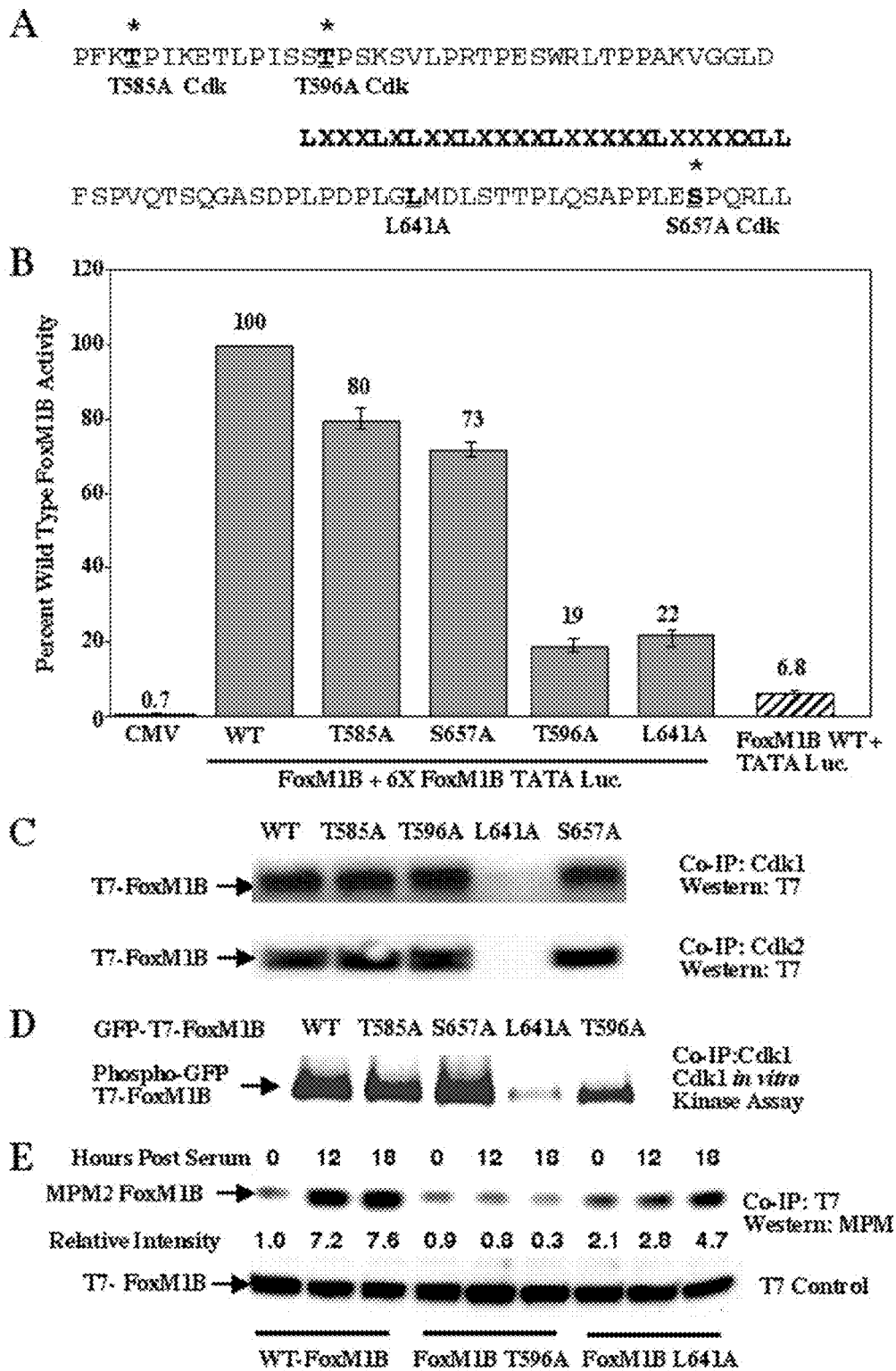

FIG. 5A shows the FoxM1B amino acid sequence from amino acid residue 582-662 (SEQ ID NO: 8) and the LXLXXL (SEQ ID NO: 3) motif, which extends from amino acid residue 635-662 (SEQ ID NO: 9). All of the Thr or Ser residues in the FoxM1B protein sequence that are potential Cdk1/Cdk2 phosphorylation sites were changed to alanine and the Leu residue at 641 in the LX<u>L</u>XXL (SEQ ID NO: 3) motif was changed to alanine.

FIG. 5B depicts a graph showing that mutation of the Cdk1 phosphorylation site at 596 and Leu residue at 641 causes diminished FoxM1B transcriptional activity. Results are expressed as the percent activity with respect to wild-type FoxM1B where CMV-empty served as a control for basal expression levels of the FoxM1B reporter gene. Four separate transfection experiments were performed in triplicate to calculate ±SD.

FIG. 5C shows the results of Western blot analysis with T7 epitope-tagged antibody of U20S cells transiently transfected with CMV-GFP-T7-FoxM1B following immunoprecipitation with a Cdk1 or Cdk2 polyclonal antibody. The immunoprecipitated proteins were subjected to Western blot analysis using a monoclonal antibody against the T7 epitope tagged antibody protein. These co-immunoprecipitation studies showed that the Leu residue at 641 was required for association with the Cdk-Cyclin complexes.

FIG. 5D shows the results of a kinase assay of U20S cells transiently transfected with CMV GFP-FoxM1B (lane1), CMV-GFP-FoxM1B T585A (lane 2), CMV GFP-FoxM1B T596A (lane 3), CMV GFP-FoxM1B L641A (lane 4), or CMV GFP-FoxM1BS657A (lane 5).

FIG. 5E shows diminished in vivo phosphorylation of the FoxM1B T596A Cdk mutant and FoxM1B L641A mutant proteins by the Cdk-Cyclin protein complexes. U20S cells were transiently transfected with either CMV T7-FoxM1B, CMV T7-FoxM1B T596A or FoxM1B L641A, and transfected cells were then serum starved for 48 hours. The cells were then incubated in the presence or absence of serum for 12 or 18 hours, the cells harvested and protein extracts prepared. Protein extracts were immunoprecipitated (IP) with an antibody specific for the T7 epitope and then subjected to Western blot analysis with MPM2 monoclonal antibody that recognizes phosphorylated Cdk sites. Western blot analysis with T7 antibody demonstrated equal amounts of FoxM1B protein in all the lanes. Relative intensity of MPM2 signal was determined and FoxM1B levels from cells not stimulated with serum was set at one.

Figure 6:
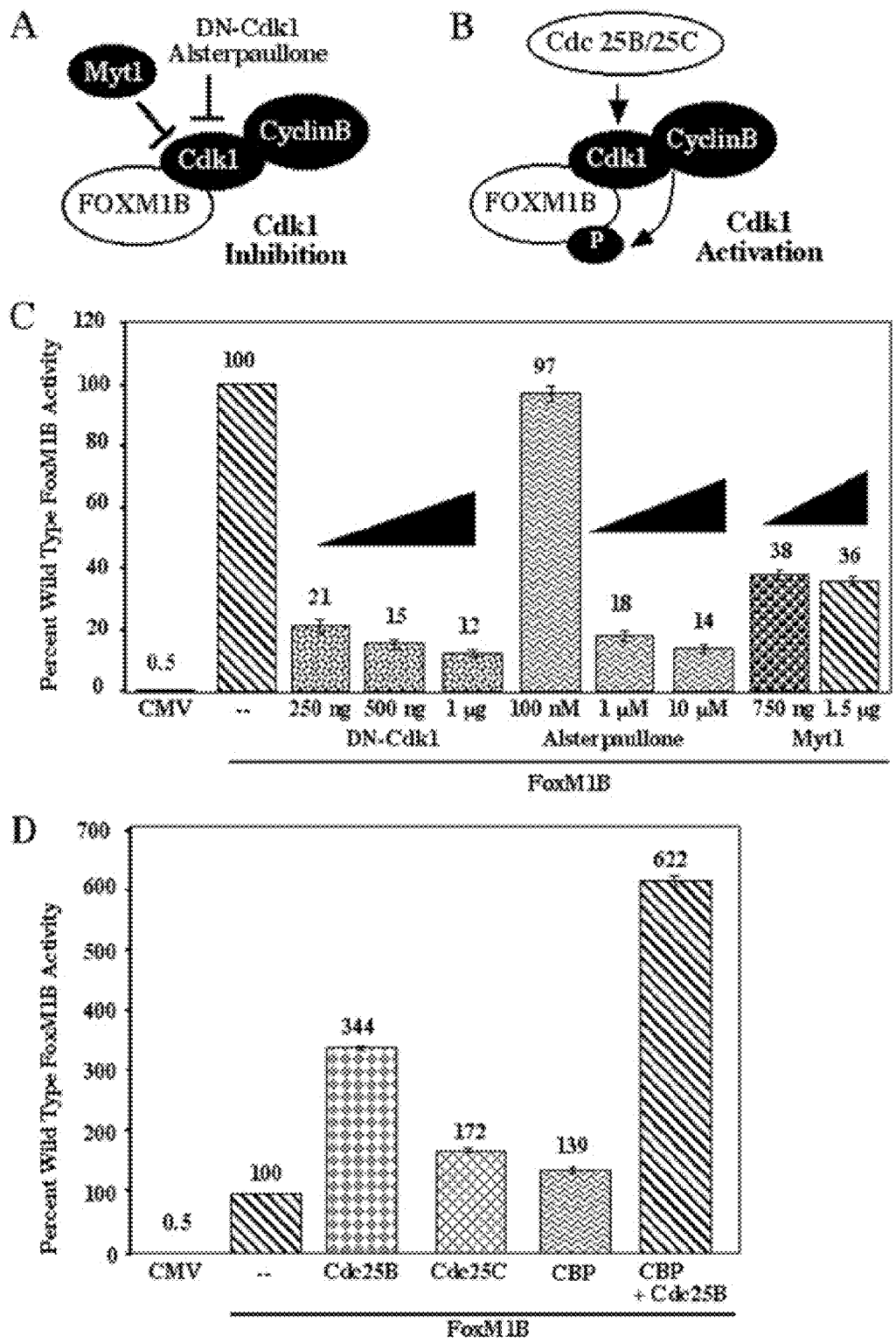
Figure 7:
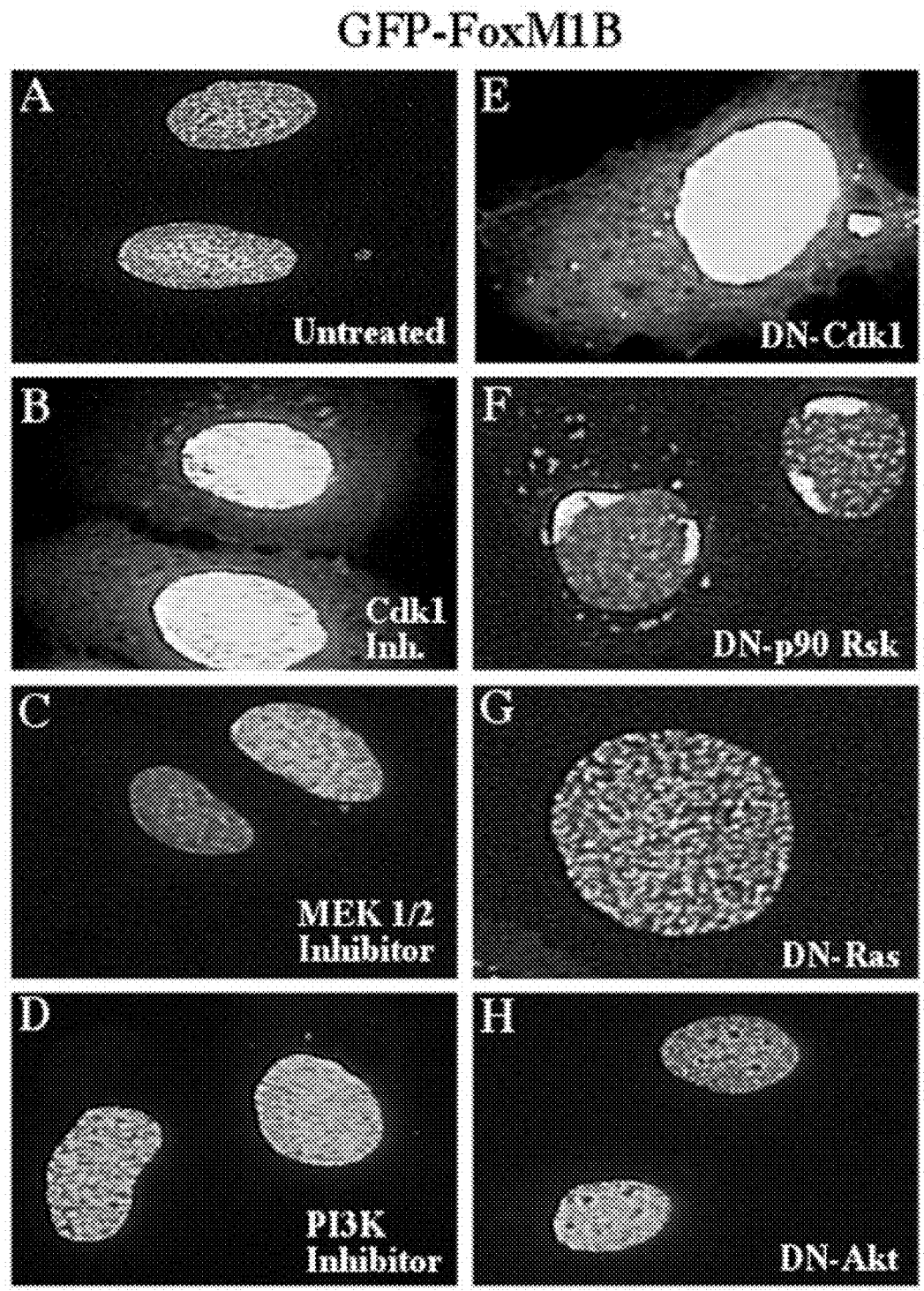

FIG. 6A is a schematic diagram depicting inhibition of Cdk1 kinase activity by either Myt1 phosphorylation, dominant-negative (DN) Cdk1 or the Cdk1 inhibitor Alsterpaullone.

FIG. 6B is a schematic diagram depicting stimulation of Cdk1 activity by Cdc25B and Cdc25C dephosphorylation.

FIG. 6C is a graph demonstrating that inhibition of Cdk1 activity diminished FoxM1B transcriptional activity in cotransfection assays. U20S TetR cells were transiently co-transfected with the reporter 6X-FoxM1B-TATA-Luciferase and CMV-TO-FoxM1B (500 ng) alone or with increasing amounts of either CMV-DN-Cdk1, Cdk1 pharmacological inhibitor Alsterpaullone or CMV-Myt1. Results are expressed as the percent activity with respect to wild-type FoxM1B using four separate transfection experiments were performed in triplicate to calculate ±SD.

FIG. 6D is a graph demonstrating that activation of Cdk1 activity by dephosphorylation with either Cdc25B or Cdc25C stimulated FoxM1B transcriptional activity, which was potentiated by increased CBP levels.

FIGS. 7A-H show nuclear localization of GFP-FoxM1B fusion protein following treatment with either pharmacological kinase inhibitors or dominant negative kinases. U20S cells were transiently transfected with CMV GFP-FoxM1B with the indicated pharmacological kinase inhibitors (B-D) or dominant-negative kinase expression vectors (E-H). Cells in panel (A) were untreated.

Figure 8:
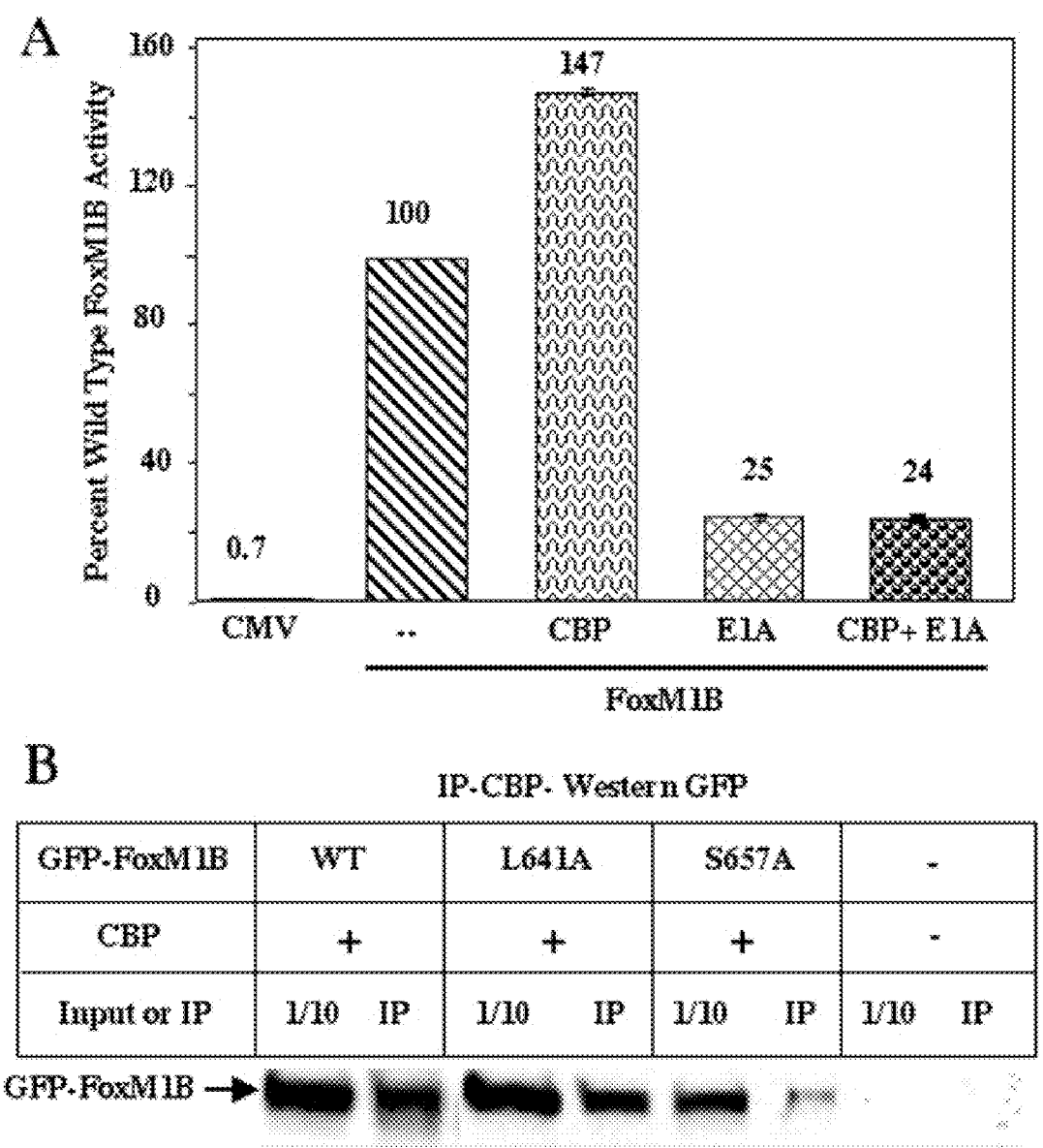

FIG. 8A is a graph demonstrating that inhibition of CBP histone acetyl transferase activity by E1A decreased the FoxM1B transcriptional activity. U20S cells were transiently co-transfected with the reporter 6X-FoxM1B-TATA-Luciferase and CMV-FoxM1B alone or in different combinations with CBP and E1A expression vectors.

FIG. 8B shows the results of Western blot analysis of cell lysates after immunoprecipitation with a monoclonal antibody that recognized CBP. U20S cells were transiently transfected with CBP and either CMV WT GFP-FoxM1B (lanes 1-2), CMV GFP-FoxM1B L641A (lanes 3-4), CMV GFP-FoxM1B S657A (lanes 5-6), or mock transfected (lanes 7-8). The first lane of each set contains 1/10 of the input protein extract (50 ug) and the second lane contains the immunoprecipitated (IP) protein extracts.

Figure 9:
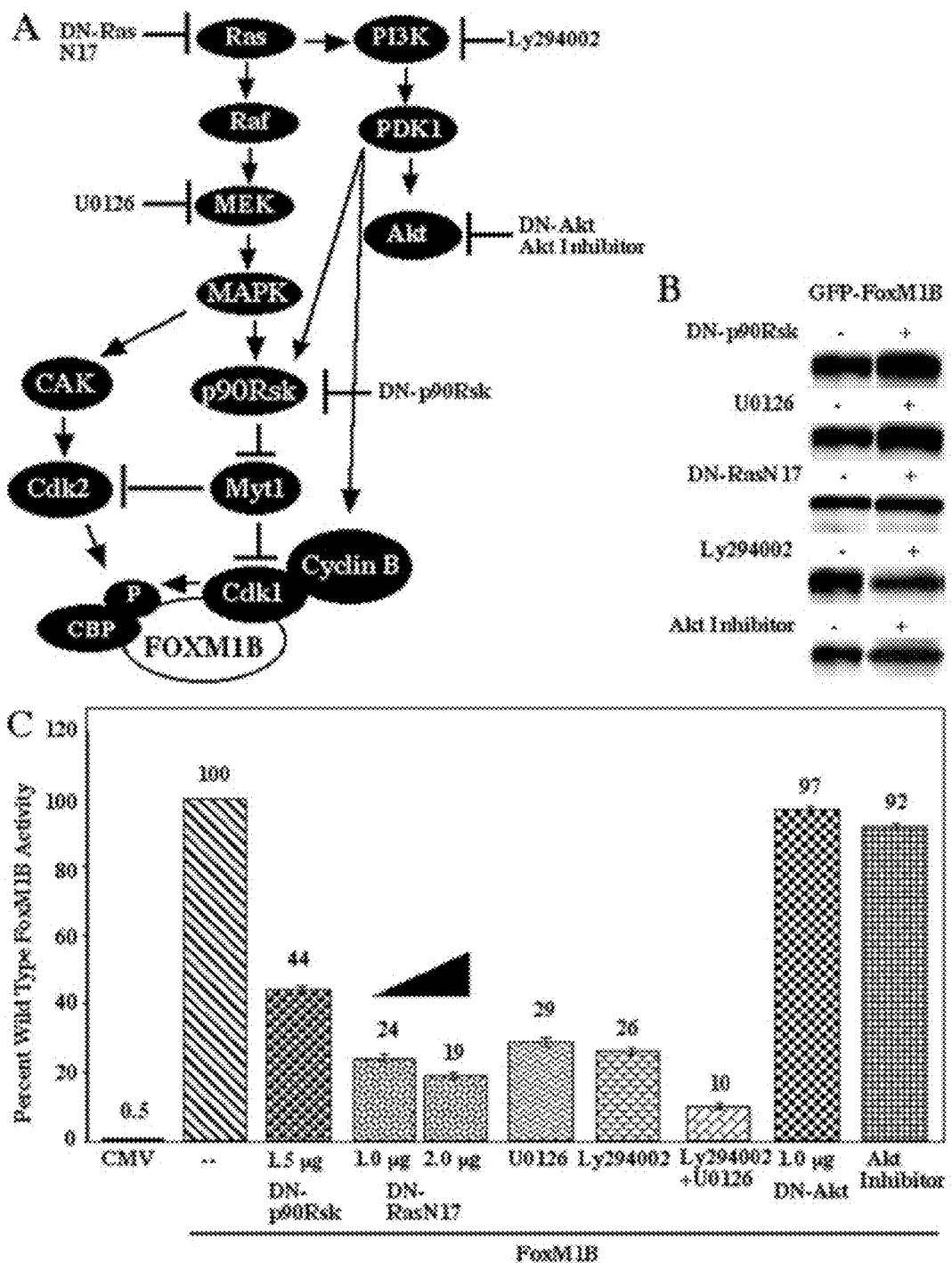

FIG. 9A shows a schematic diagram depicting the Ras/MEK/MAPK/p90Rsk/Myt1 and PI3K/PDK1/p90Rsk/Myt1 pathways, which prevent Myt1 phosphorylation mediated inhibition of Cdk1 activity. Also shown is the action of DN-RasN17, the MEK1/2 inhibitor U0126, PI3K inhibitor Ly294002, DN-Akt and Akt pharmacological kinase inhibitor and DN-p90Rsk.

FIG. 9B shows the results of Western blot analysis with GFP antibody of protein extracts from U20S cells transiently transfected with CMV GFP-FoxM1B plasmid with either CMV DN-p90Rsk or CMV DN-RasN17 or 50 μM of U0126, 50 μM of PI3K inhibitor Ly294002 or 25 μM of Akt inhibitor.

FIG. 9C is a graph demonstrating that inhibition of Ras/MEK/MAPK/p90Rsk and PI3K/PDK1/p90Rsk pathways resulted in diminished FoxM1B transcriptional activity.

U2OS TetR cells were transiently co-transfected with the reporter 6X-FoxM1B-TATA-Luciferase and CMV-TO-FoxM1B (500 ng) with CMV-DN-p90Rsk, CMV-DN-Ras or DN-AKT or with 50 µM of either U0126 or Ly294002 alone or together or with 25 µM of Akt inhibitor. Four separate transfection experiments were performed in triplicate to calculate ±SD.

Figure 10:
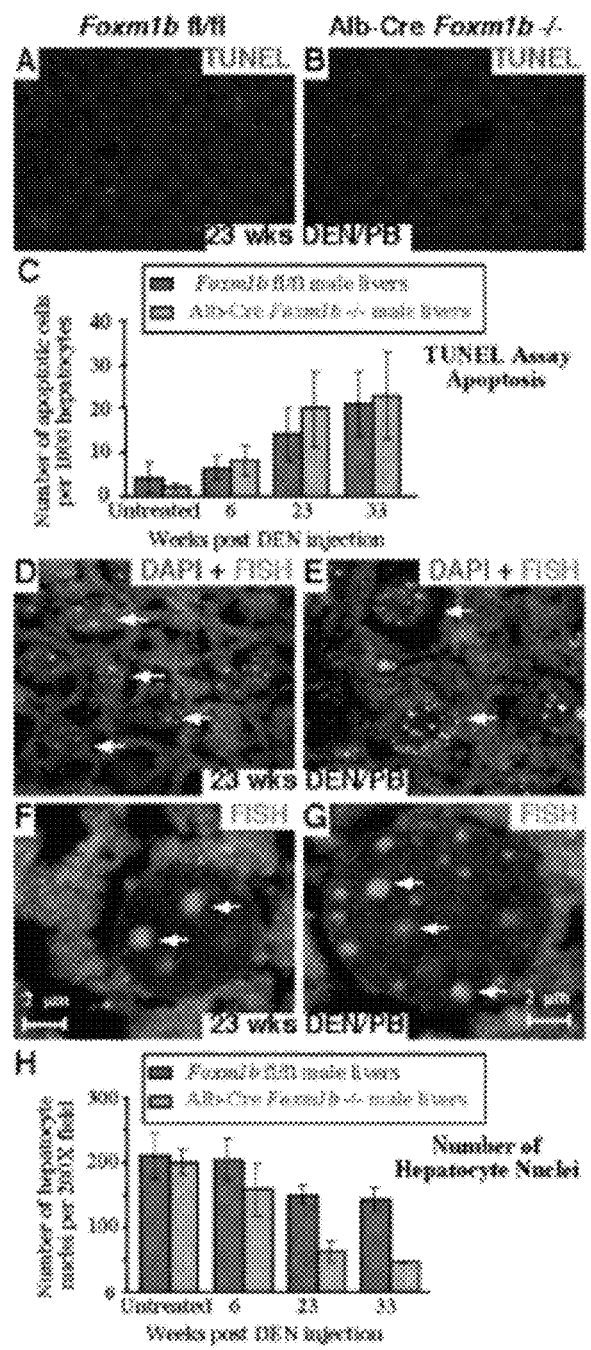

FIGS. 10A-B show fluorescent micrographs of TUNEL assay (100×) demonstrated similar apoptosis levels in Alb-Cre Foxm1b−/− and Foxm1b fl/fl control after 23 weeks of DEN/PB exposure.

FIG. 10C shows a graph of the number of apoptotic cells (TUNEL positive) per 1000 hepatocytes (±SD) in non-tumor regions of livers from male Foxm1b fl/fl or Alb-Cre Foxm1b−/− mice after either 0, 6, 23, or 33 weeks of DEN/PB exposure.

FIGS. 10D-G show high power magnification of hepatocytes in which the nuclei were counterstained with DAPI (630×; D-E) or visualized by Laser Confocal microscopy (F-G; bar indicates 2 µm). A centromere-specific mouse fluorescent in situ hybridization (FISH) probe was used to show that Alb-Cre Foxm1b−/− hepatocyte nuclei possessed an increase in the number of hybridizing chromosomes compared to control hepatocyte nuclei at 23 weeks of DEN/PB treatment.

FIG. 10H is a graph of the mean number of DAPI stained hepatocyte nuclei per 200× field (±SD) in non-tumor regions of livers from male Foxm1b fl/fl or Alb-Cre Foxm1b−/− mice either untreated or after 6, 23, or 33 weeks of DEN/PB exposure. The mean number (±SD) of TUNEL or DAPI positive hepatocyte nuclei per 1000 cells or 200× field was calculated by counting the number of positive hepatocyte nuclei using 5 different liver sections from 3 male mice at the indicated times of DEN/PB exposure.

FIGS. 11A-H shows immunohistochemically stained liver sections from Foxm1b fl/fl and Alb-Cre Foxm1b−/− mice either untreated or treated with DEN/PB for either 6, 23 or 33 weeks stained for nuclear expression of FoxM1B protein. Abundant nuclear staining of FoxM1B protein was induced as early as 6 weeks after DEN/PB exposure in Foxm1b fl/fl hepatocytes surrounding the periportal vein (PV, C), but not in hepatocytes near the central vein (CV). High levels of nuclear FoxM1B protein persisted in hyper-proliferative hepatic adenomas and HCC(C and E, margins of tumor indicated by arrows). As expected, nuclear staining of Foxm1b protein was not found in Alb-Cre Foxm1b−/− hepatocytes at any of the time points following DEN/PB treatment (B, D, F and H). Abbreviations are PV, portal vein and CV, central vein. Magnifications are 200×.

FIGS. 12A-I shows that Alb-Cre Foxm1b−/− livers exhibit normal expression of GST-pi and CAR following DEN/PB treatment. Alb-Cre Foxm1b−/− and Foxm1b fl/fl livers isolated from male mice after 23 weeks of DEN/PB exposure were immunohistochemically stained with antibody specific to Glutathionine-S-transferase placental isoform (GST-pi). Both Alb-Cre Foxm1b−/− and Foxm1b fl/fl hepatocytes were strongly immunostained for GST-pi after 23 weeks of DEN/PB treatment (C-F) but its expression was not detected in untreated control Foxm1b fl/fl mouse liver (A-B). Western blot analysis with liver protein extracts demonstrated that hepatic expression of GST-pi protein was induced as early as 6 weeks following DEN/PB treatment and that its hepatic expression continued following 23 weeks of DEN/PB exposure (G). Normal hepatocyte nuclear levels of the CAR nuclear receptor were found in male Alb-Cre Foxm1b−/− mice following DEN/PB treatment (H-I). Magnifications: A, C, E is 50×; B, D, F, H, I is 200×.

Figure 13:
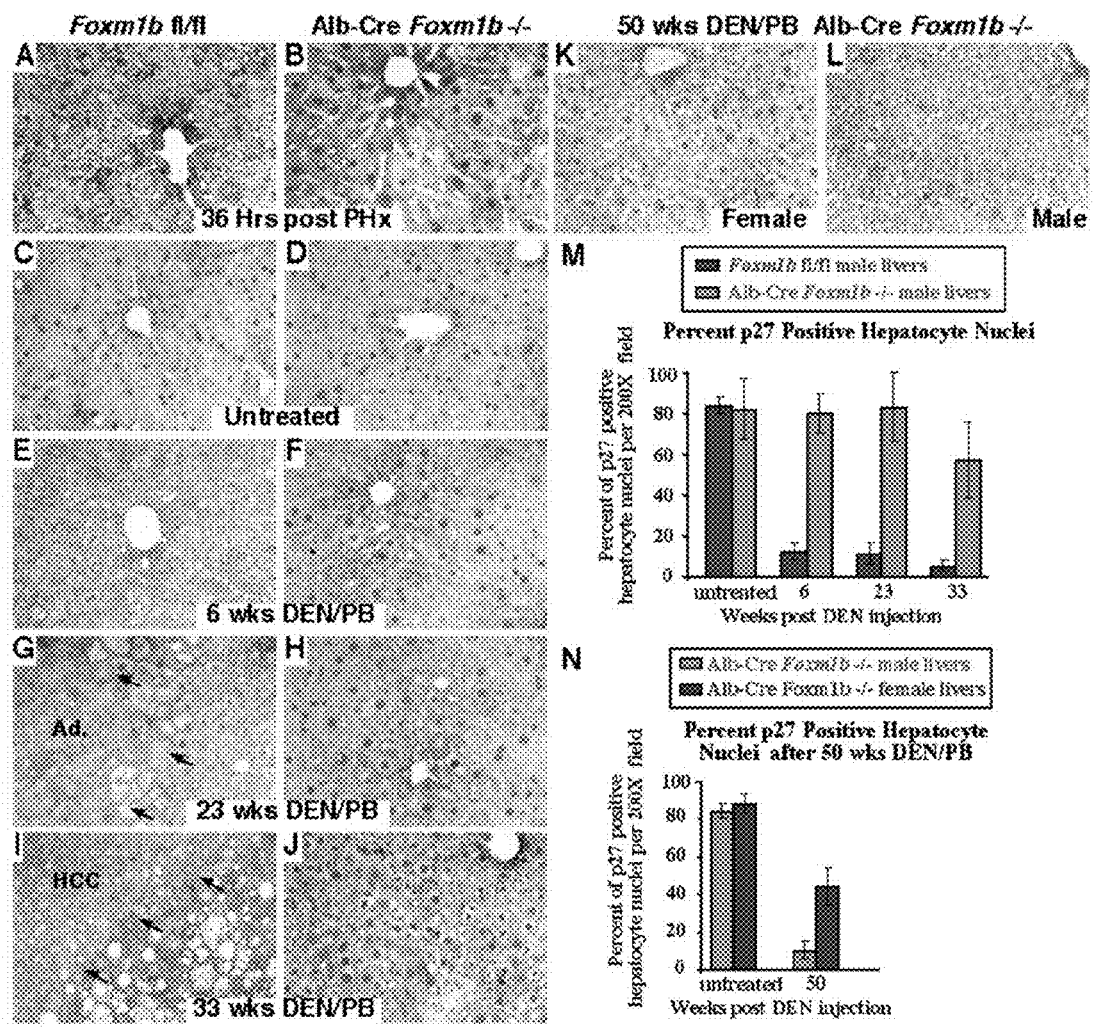

FIGS. 13A-B show $p27^{Kip1}$ immunohistochemical staining of liver sections from untreated Alb-Cre Foxm1b−/− and Foxm1b fl/fl mice.

FIGS. 13C-J show immunohistochemical staining of liver sections from Alb-Cre Foxm1b−/− and Foxm1b fl/fl male mice after either untreated or after 6, 23, or 33 weeks of DEN/PB exposure to examine hepatocyte nuclear expression of $p27^{Kip1}$ protein. In FIGS. 13E and G, the margins of hepatic adenoma (Ad) or hepatocellular Carcinoma (HCC) are indicated by arrows. Magnification: A-J is 200×.

FIG. 13K shows immunohistochemical staining of $p27^{Kip1}$ protein in female Alb-Cre Foxm1b−/− mice hepatocytes after 50 weeks DEN/PB treatment.

FIG. 13L shows immunohistochemical staining of $p27^{Kip1}$ protein in male Alb-Cre Foxm1b−/− mice hepatocytes after 50 weeks of DEN/PB.

FIGS. 13M-N show graphs of percent $p27^{Kip1}$ positive hepatocyte nuclei per 200× field liver section during tumor progression. Number of hepatocyte nuclei per 200× section was determined by DAPI staining.

Figure 14:
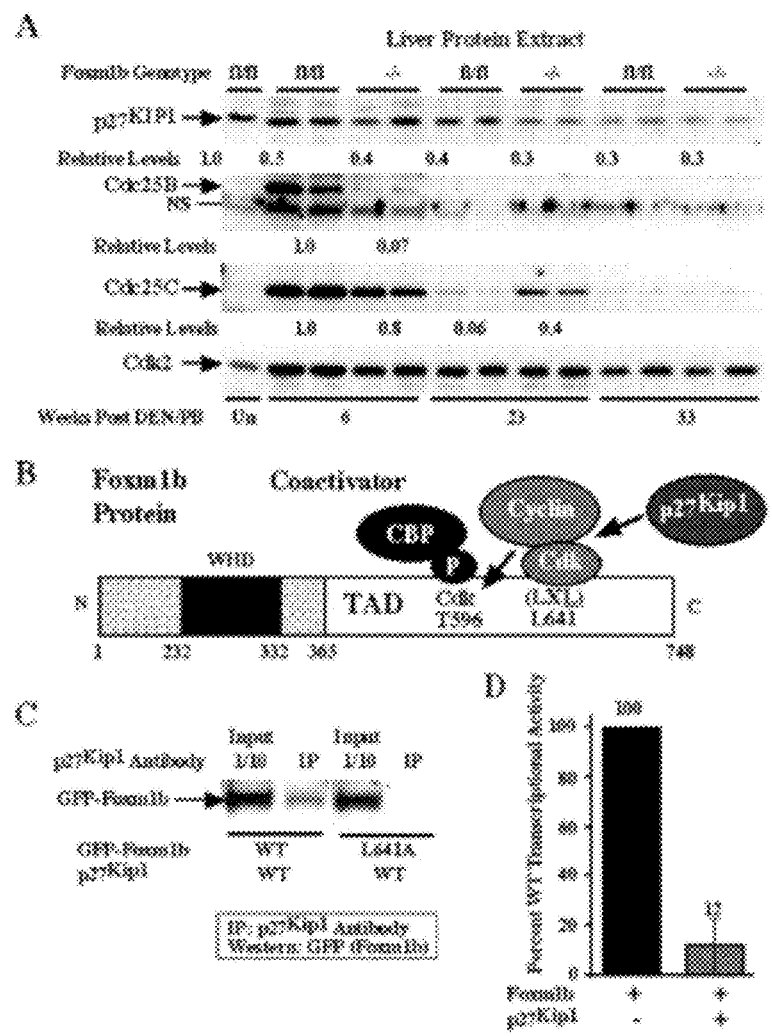

FIG. 14A shows results from Western blot analysis of $p27^{Kip1}$, Cdc25B or Cdc25C protein expression in liver protein extracts isolated from either untreated or DEN/PB treated mice. Expression levels of Cdk2 were used as a loading control.

FIG. 14B is a drawing depicting the FoxM1B winged helix DNA binding domain (WHD), the C-terminal transcriptional activation domain (TAD), and the FoxM1B LXL motif (639-641) that recruits either the Cdk2-Cyclin E/A (S-phase) or Cdk1-Cyclin B (G2 phase) complexes.

FIG. 14C shows co-immunoprecipitation (Co-IP) assays with protein extracts prepared from U2OS cells that were transiently transfected CMV $p27^{Kip1}$ and with CMV expression vectors containing either WT GFP-FoxM1B or GFP-Foxm1b L641A mutant protein that fail to recruit the Cdk-Cyclin complexes. Also shown is a control lane containing 1/10 of the extract used in the Co-IP experiment.

FIG. 14D shows that $p27^{Kip1}$ protein inhibited FoxM1B transcriptional activity in cotransfection assays. Transfections were performed twice in triplicate and used to calculate percent WT FoxM1B transcriptional levels (±SD).

Figure 15:
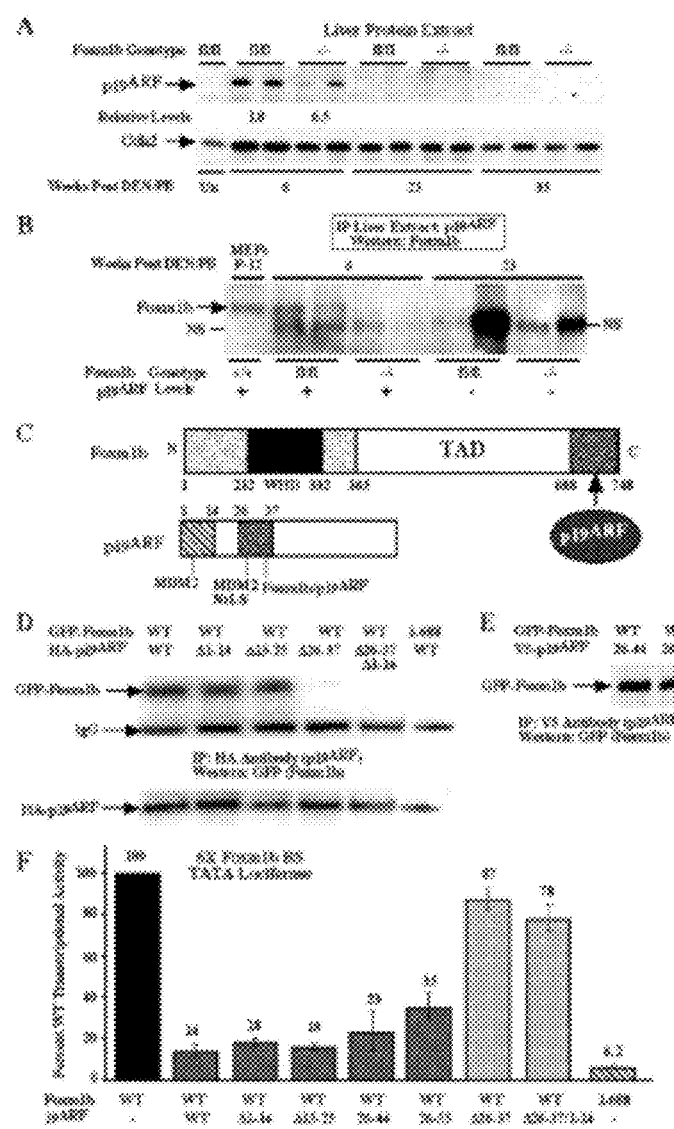

FIG. 15A shows Western Blot analysis, blotting with a $p19^{ARF}$ (p19) antibody, of liver extracts prepared from two mice following either no treatment or 6, 23 and 33 weeks of DEN/PB exposure. Expression levels of Cdk2 were used as a loading control.

FIG. 15B shows co-immunoprecipitation (Co-IP) assays performed with liver protein extracts prepared from Foxm1b fl/fl and Alb-Cre Foxm1b−/− mice following either 6 or 23 weeks of DEN/PB treatment. The protein extracts were first immunoprecipitated with p19 antibody and then analyzed by Western blot analysis with a mouse FoxM1B antibody.

FIG. 15C is a drawing depicting functional domains of the FoxM1B and $p19^{ARF}$ tumor suppressor proteins. Schematically shown is the FoxM1B winged helix DNA binding domain (WHD), the C-terminal transcriptional activation domain (TAD) and the C-terminal region (688-748) required for $p19^{ARF}$ (p19) binding. Schematically shown are the p19 nucleolar localization sequence (NrLS) and the p19 Mdm2 and FoxM1B binding sites.

FIG. 15D shows co-IP assays with protein extracts prepared from U2OS cells that were transiently transfected with CMV green fluorescent protein (GFP)-FoxM1B fusion protein and with p19 expression vectors. These included expression vectors containing either WT p19 protein or N-terminal deletion mutants of the p19 protein (Δ1-14, Δ15-25, Δ26-37, Δ26-37+Δ1-14) that were fused with an hemagglutinin (HA)

epitope tag. The p19 protein was immunoprecipitated from transfected protein extracts with HA antibody followed by Western blot analysis with a monoclonal antibody specific to the GFP protein to detect the GFP-FoxM1B fusion protein.

FIG. 15E shows co-IP assays with protein extracts prepared from U2OS cells that were transiently transfected with CMV GFP-FoxM1B fusion protein and expression vector containing V5 epitope tagged p19$^{ARF}$ 26-44 or p19$^{ARF}$ 26-55 sequences. The p19 protein was immunoprecipitated from transfected protein extracts with V5 epitope antibody followed by Western blot analysis with GFP monoclonal antibody.

FIG. 15F shows that the p19 protein inhibits FoxM1B transcriptional activity in cotransfection assays.

FIGS. 16A-D shows immunostaining of U2OS cells transfected with HA-p19ARF and GFP-FoxM1B expression vectors demonstrating that the HA tagged p19 was able to target nuclear fluorescence of WT GFP-Foxm1b fusion protein (D) to the nucleolus (B, C).

FIGS. 16E-I shows nucleolar targeting of GFP-FoxM1B WT protein in cotransfections with CMV expression vectors containing mutant p19$^{ARF}$ proteins (Δ1-14, Δ15-25, 26-44 or 26-55) that were still able to associate with FoxM1B protein.

Figure 16:
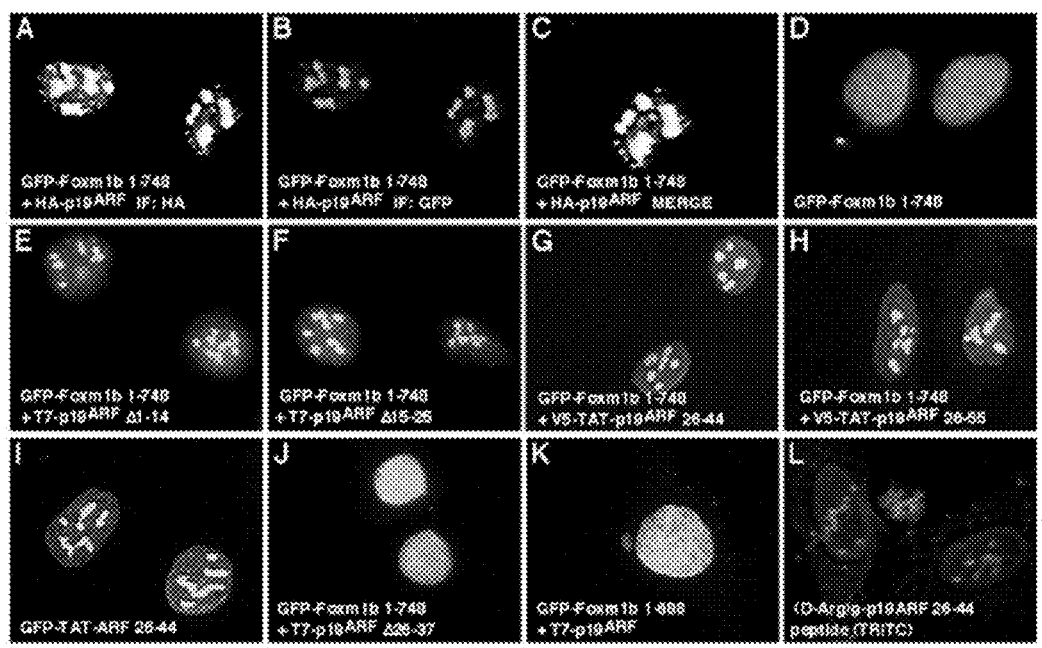

FIG. 16I shows nucleolar fluorescence of CMV GFP-p19$^{ARF}$ 26-44.

FIG. 16J shows nuclear fluorescence of CMV WT GFP-FoxM1B and expression vector containing mutant p19$^{ARF}$ Δ26-37 protein that failed to interact with FoxM1B.

FIG. 16K shows transfection of CMV WT p19 expression vector was unable to elicit nucleolar targeting of GFP-FoxM1B 1-688 protein, which failed to bind to p19 protein.

FIG. 16L shows that treatment of U2OS cells for three days with the TRITC fluorescently tagged (D-Arg)$_9$-p19$^{ARF}$ 26-44 peptide demonstrated that this p19$^{ARF}$ peptide was transduced into the cell and was localized to the nucleolus.

Figure 17:
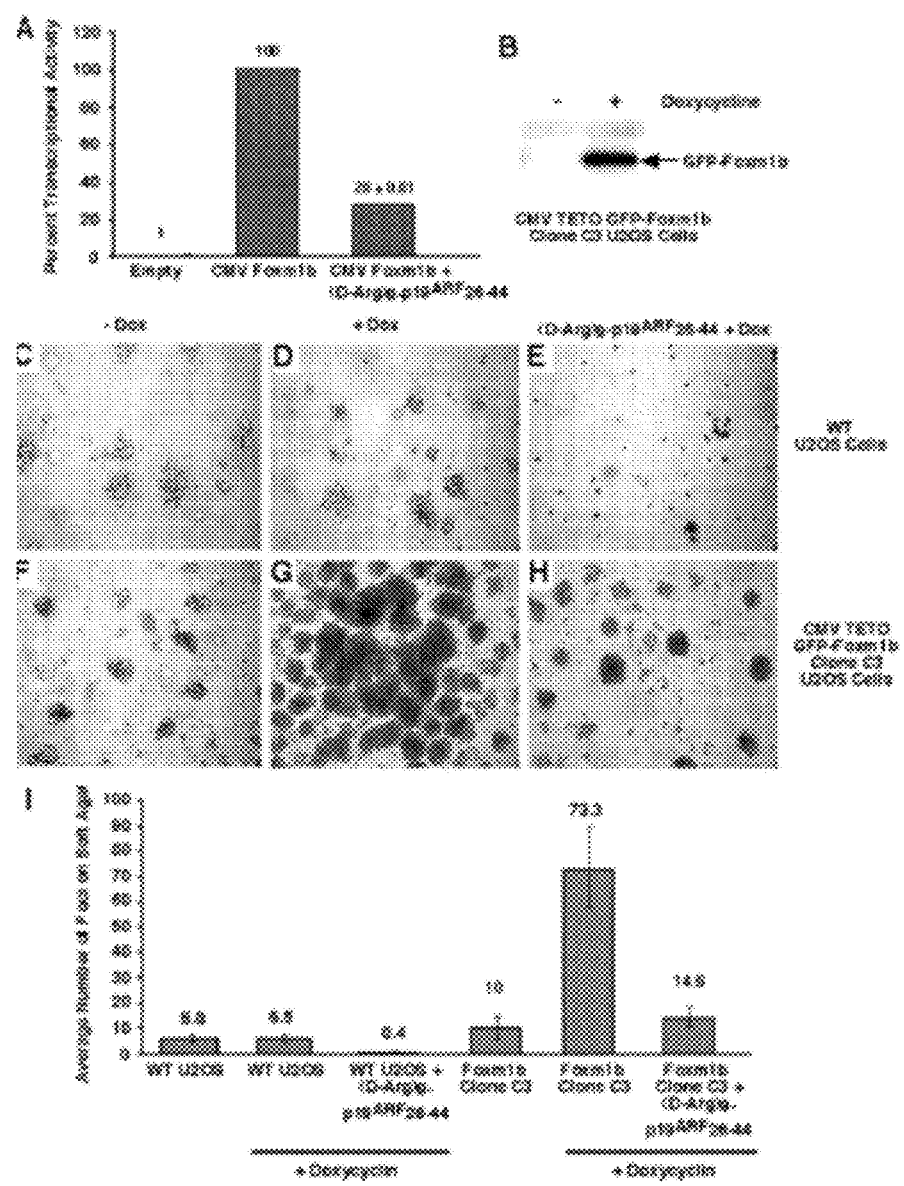

FIG. 17A is a graph showing that the (D-Arg)$_9$-p19$^{ARF}$ 26-44 peptide was an effective inhibitor of FoxM1B transcriptional activity.

FIG. 17B is a Western blot analysis showing that the CMV-TETO GFP-Foxm1b U2OS clone C3 cell line displayed Doxycycline inducible expression of the GFP-FoxM1B fusion protein.

FIGS. 17C-H shows results of colony formation assays wherein the (D-Arg)$_9$-p19$^{ARF}$ 26-44 peptide significantly diminished the ability of induced GFP-FoxM1B to stimulate colony formation of the U2OS clone C3 cells on soft agar. Doxycycline induced FoxM1B-GFP expression stimulated anchorage-independent growth in the U2OS clone C3 cell line (F-G) as assessed by propagation for two weeks on soft agar while the (D-Arg)$_9$-p19$^{ARF}$ 26-44 peptide significantly inhibited colony formation of U2OS cells on soft agar (E and H).

FIG. 17I shows a graph depicting quantitation of FoxM1B induced formation of U2OS cell colonies on soft agar treated or not treated with the (D-Arg)$_9$-p19$^{ARF}$ 26-44 peptide. The number of U2OS colonies of the indicated treatments were counted in 4 to 5 different 100× fields and determined the mean number of cell colonies (±SD).

Figure 18A:
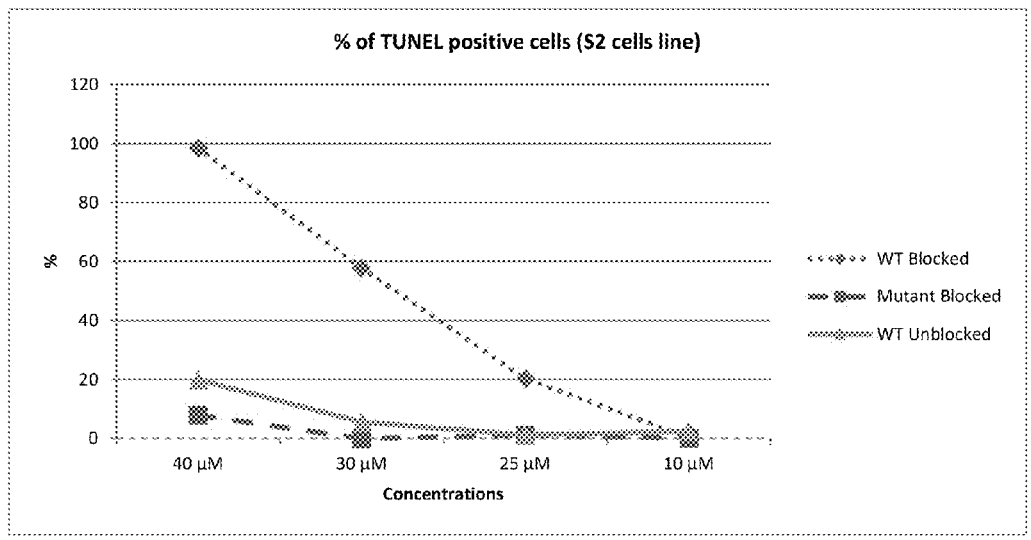
Figure 18B:
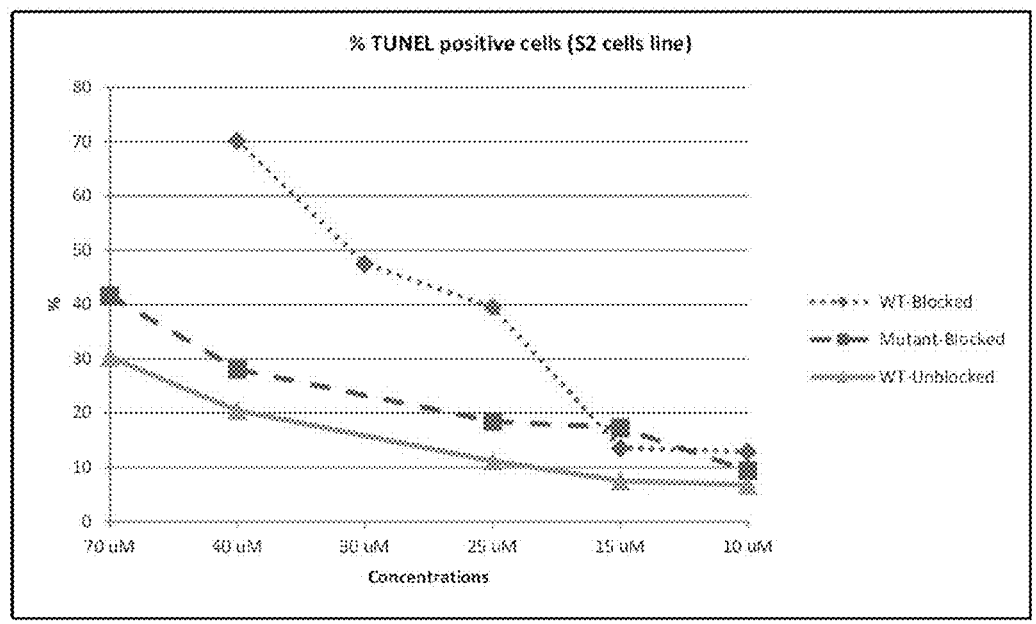

FIGS. 18A and 18B show graphs depicting quantitation of deoxynucleotidyl transferase dUTP nick end labeling ("TUNEL") positive cells treated with either WT-blocked, WT-unblocked or mutant-unblocked (D-Arg)$_9$-p19$^{ARF}$ 26-44 peptide. The cells treated with WT-blocked (D-Arg)$_9$-p19$^{ARF}$ 26-44 peptides had a significantly higher number of TUNEL positive cells compared to cells treated with WT-unblocked and mutant-blocked (D-Arg)$_9$-p19$^{ARF}$ 26-44 peptides. In FIG. 18A WT-unblocked (D-Arg)$_9$-p19$^{ARF}$ 26-44 peptides showed some activity compared to the mutant-blocked peptides at doses higher than 30 μM (statistically significant at 30 and 40 μM). The experiments underlying FIGS. 18A (experiment 1) and 18B (experiment 2) were performed using the same protocol on separate dates.

Figure 19A:
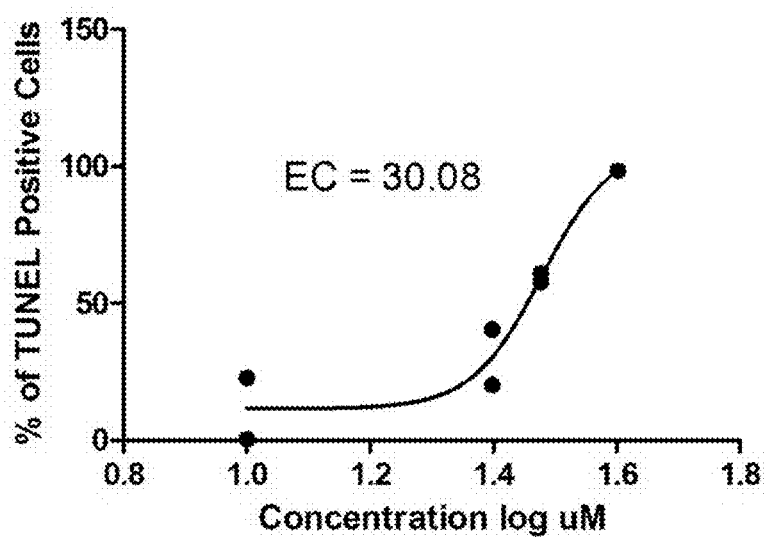
Figure 19B:
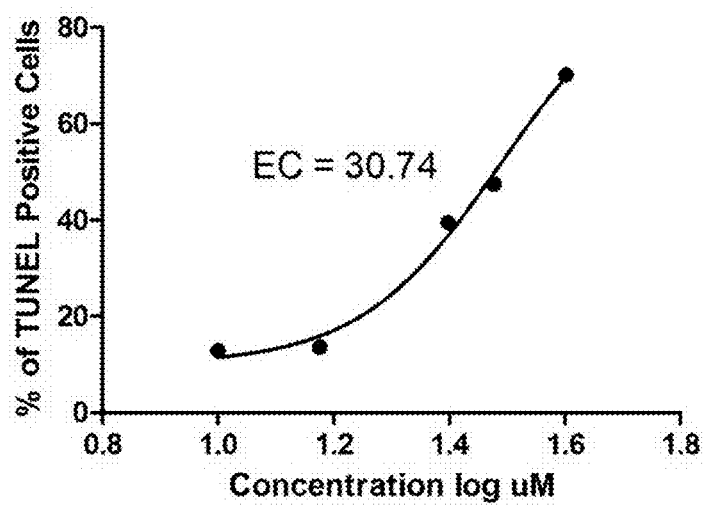

FIGS. 19A and 19B show graphs depicting quantitation of TUNEL positive cells following treatment using various concentrations of the WT-blocked (D-Arg)$_9$-p19$^{ARF}$ 26-44 peptides. The EC50 (D-Arg)$_9$-p19$^{ARF}$ 26-44 peptides for WT-blocked was 30.08 μM and 30.73 μM for FIGS. 19A and 19B, respectively). The experiments underlying FIGS. 19A (experiment 1) and 19B (experiment 2) were performed using the same protocol on separate dates.

Figure 20:
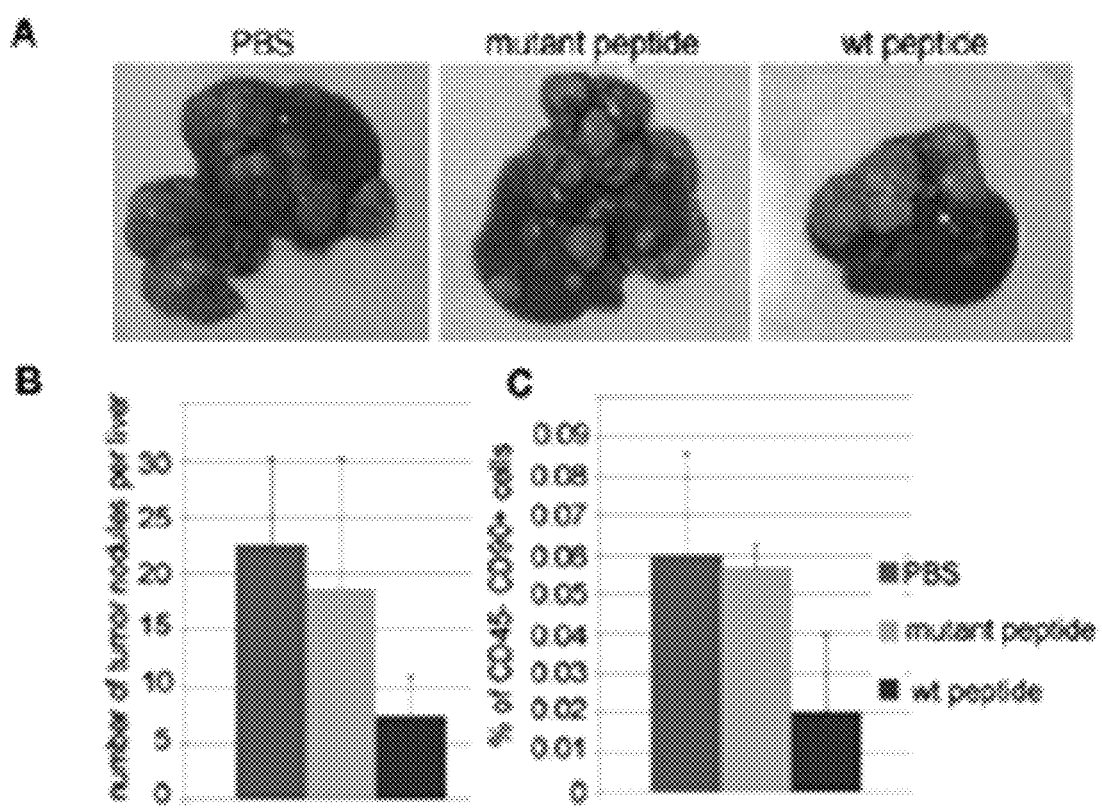

FIG. 20A shows photographs of tumor nodules isolated from ALb-HRasV12 mice treated with PBS, mutant ARF-peptide or ARF-peptide for three weeks.

FIG. 20B is a graph showing the quantification of tumor nodules from ALb-HRasV12 mice treated with PBS, mutant ARF-peptide or ARF-peptide for three weeks. The ARF-peptide treated mice showed a reduction of tumor nodules.

FIG. 20C is a graph showing the percentage of CD45-CD90+ cells from ALb-HRasV12 mice treated with PBS, mutant ARF-peptide or ARF-peptide for three weeks. The results indicate that there was a considerable reduction in the CD45- CD90+ cells in the ARF-peptide treated mice.

FIGS. 21A-21D are graphs showing cell viability measured by proportional luminescence signal generated by cell-titer-glo assay. CreERT2, Foxm1 fl/fl and p53-/- thymic lymphoma (represented by "L1" and "L2") (FIGS. 21A and 21B, respectively), Foxm1 fl/fl and p53-/- thymic lymphoma (represented by "C") (FIG. 21C) and CreERT2, Foxm1 fl/fl and p53-/- sarcoma (represented by "S") (FIG. 21D) were treated with ethanol as vehicle or 800 nM of 4OH-tamoxifen (Tam).

Figure 22:
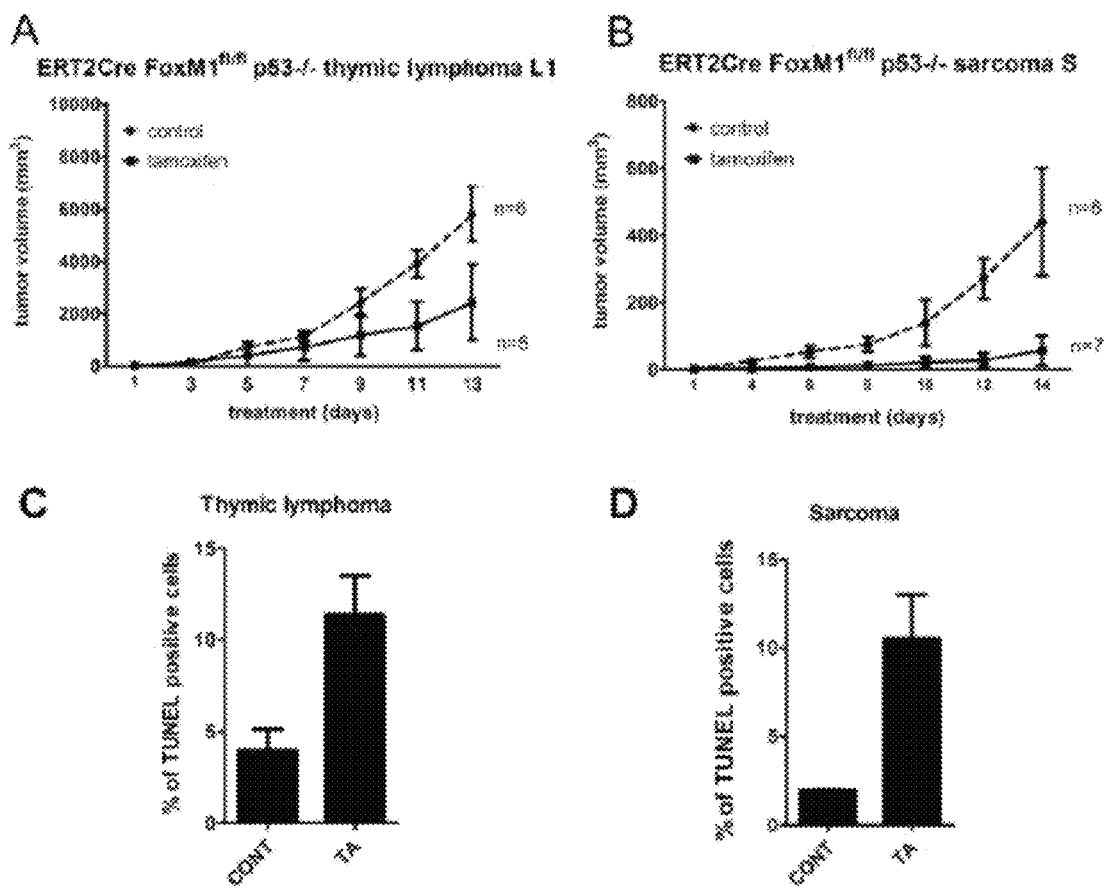

FIGS. 22A and 22B are graphs showing tumor volumes of the subcutaneously inoculated CreERT2 Foxm1 fl/fl and p53-/- thymic lymphoma cell L1 (FIG. 22A) and sarcoma cell S (FIG. 22B) following FoxM1 ablation by tamoxifen and control treatment.

FIGS. 22C and 22D are graphs showing the quantification of percentage of TUNEL positive cell per field of sarcoma (FIG. 22C) and per field of thymic lymphoma (FIG. 22D).

FIGS. 23A-23H are photographs illustrating reduced expression of Survivin and Bmi1 following FoxM1 ablation in p53 null tumors. FIGS. 23A-23D show representative Survivin staining of subcutaneously inoculated CreERT2 Foxm1 fl/fl and p53-/- lymphoma and sarcoma cells following tamoxifen and control treatment. FIGS. 23E-23H show representative Bmi1 staining of subcutaneously inoculated CreERT2 Foxm1 fl/fl and p53-/- lymphoma and sarcoma cells following tamoxifen and control treatment.

Figure 23:
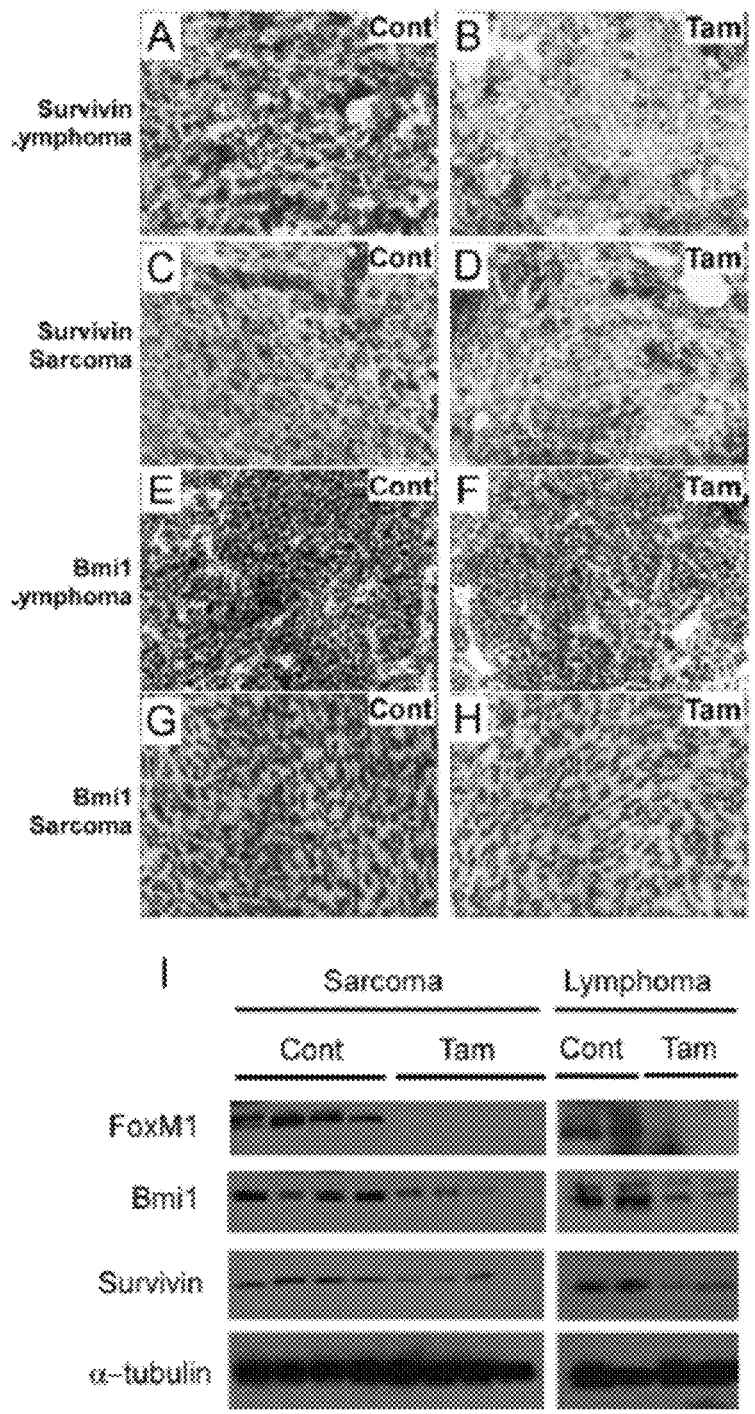

FIG. 23I is a Western blot of protein lysates extracted from allografted tumors assayed for FoxM1, Bmi1 and Survivan. alpha-tubulin was used as a loading control. Lysates were collected from both control oil treated mice and tamoxifen treated mice.

Figure 24:
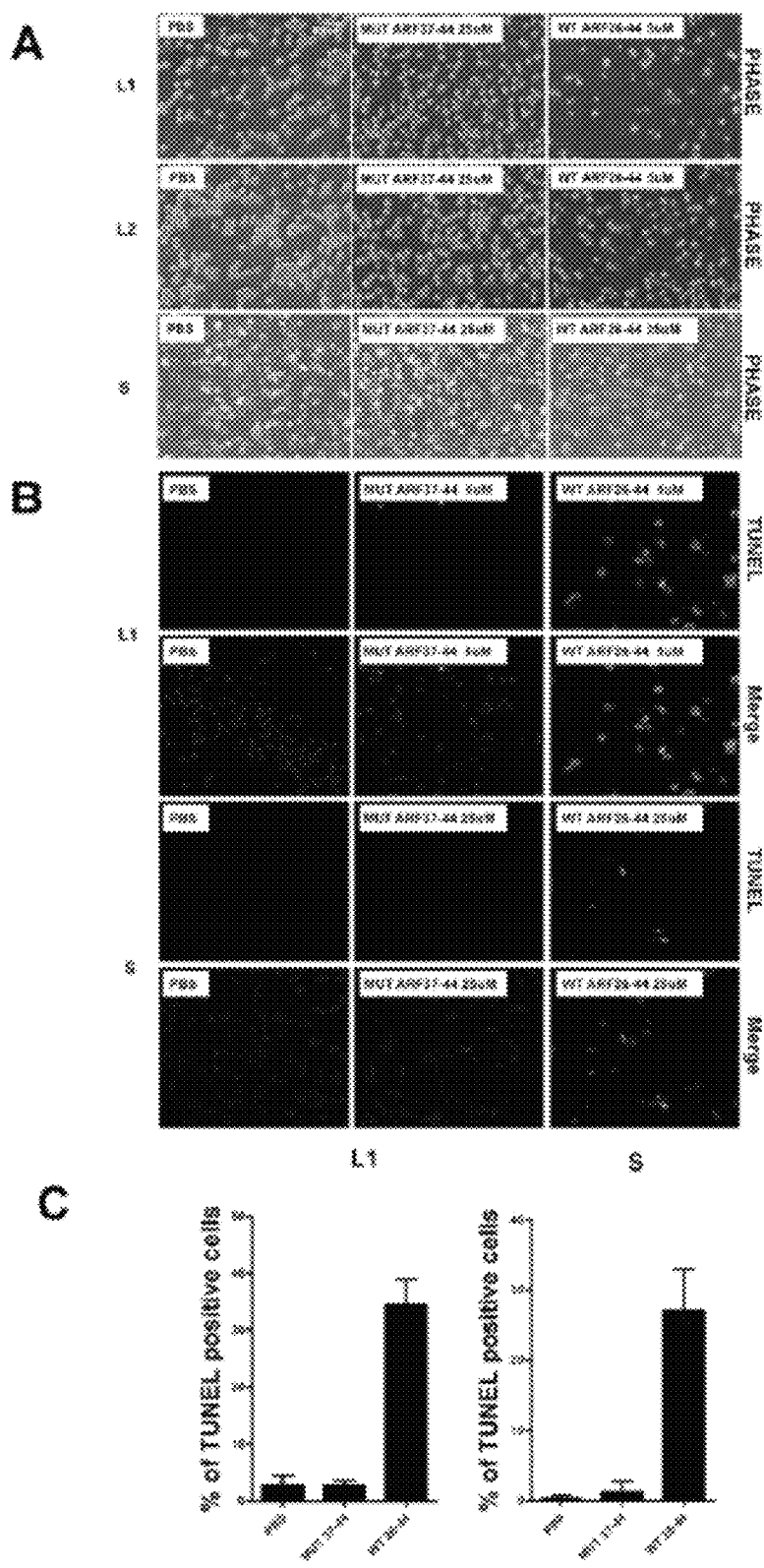

FIG. 24A is phase contrast photographs of CreERT2 Foxm1 fl/fl and p53-/- thymic lymphoma (L1) and sarcoma cells (S) treated with PBS, ARF$_{37-44}$ peptide (Mut) or ARF$_{26-44}$ peptide (WT) for 24 hours.

FIG. 24B is photographs showing TUNEL and DAPI staining of CreERT2 Foxm1 fl/fl and p53-/- thymic lymphoma (L1) and sarcoma cells (S) treated with PBS, ARF$_{37-44}$ peptide (Mut) or ARF$_{26-44}$ peptide (WT). FIG. 24C is a graph showing quantification of percentage of TUNEL positive cells per field.

Figure 25:
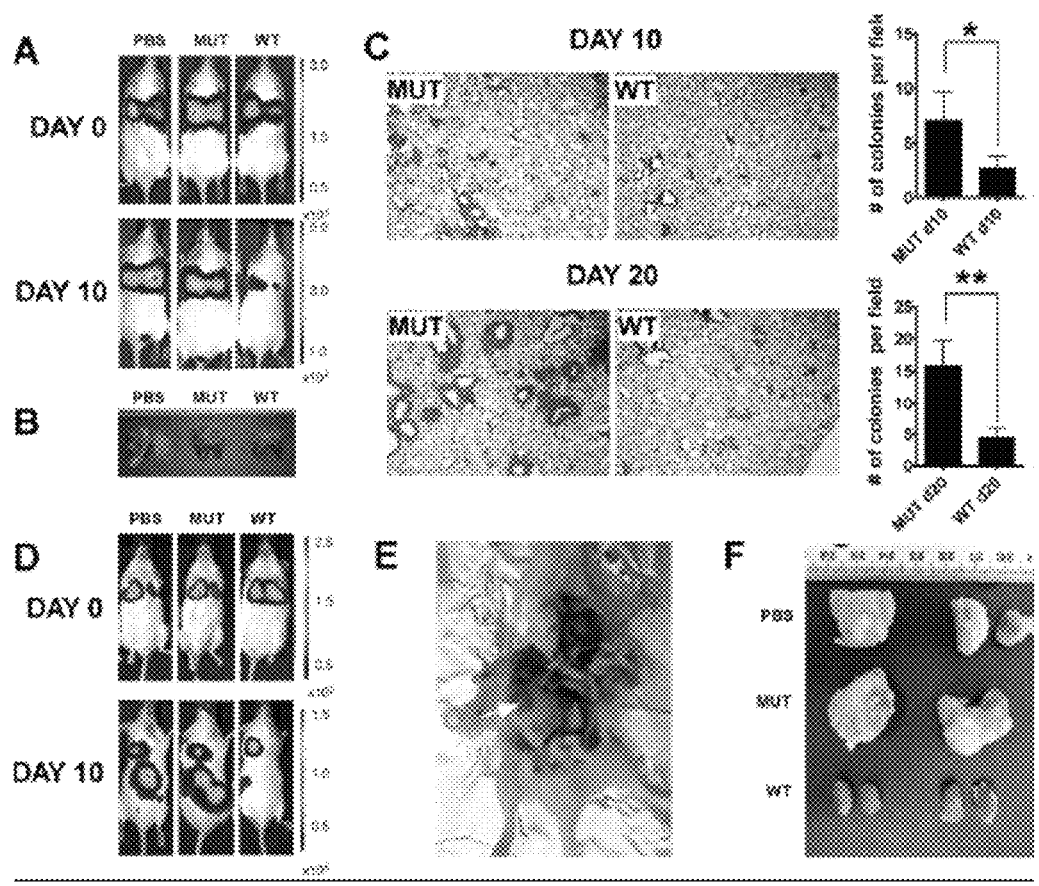

FIG. 25A is photographs illustrating luciferase intensity monitored with IVIS image machine in SCID mice intravenously inoculated with CreERT2 Foxm1 fl/fl and p53−/− sarcoma cells following peptide treatment at 10 days after initial injection and right after injection at day 0.

FIG. 25B is a picture of lung from PBS, $ARF_{37-44}$ peptide (Mut) or $ARF_{26-44}$ peptide (WT) treated mice.

FIG. 25C is pictures of H&E staining of lung tissue section from $ARF_{37-44}$ peptide (Mut) or $ARF_{26-44}$ peptide (WT) treated mice at day 10 and day 20 after initial injection and quantification of the number of the colonies per field of the corresponding lung tissue section.

FIG. 25D is photographs illustrating luciferase intensity monitored with IVIS image machine in SCID mice intravenously inoculated with CreERT2 Foxm1 fl/fl and p53−/− thymic lymphoma cells following peptide treatment at 10 days after initial injection and right after injection at day 0.

FIG. 25E is a photograph of tumor mass in kidney.

FIG. 25F is tumor mass of kidneys dissected from PBS, $ARF_{37-44}$ peptide (Mut) or $ARF_{26-44}$ peptide (WT) treated SCID mice. Representative two mice from each group are shown.

Figure 26:
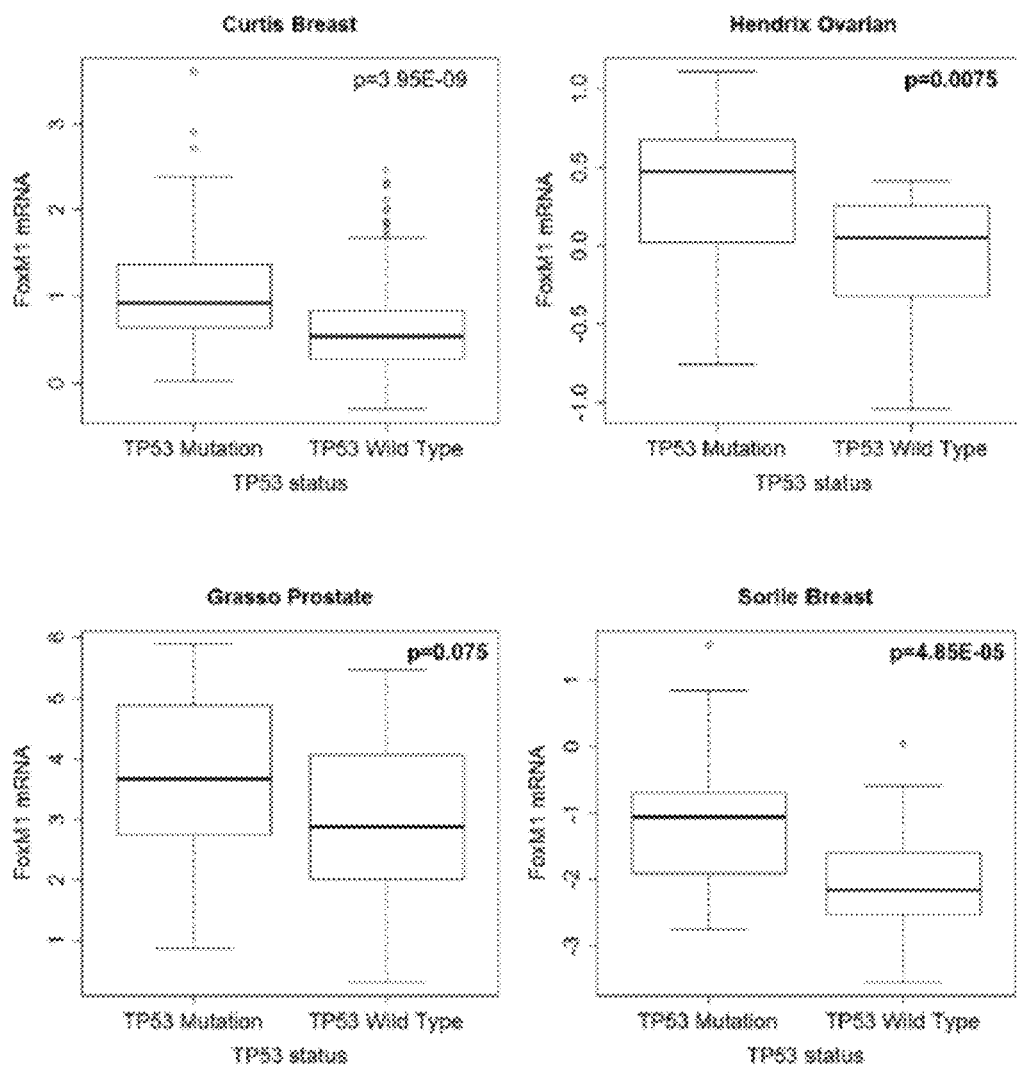

FIG. 26 is box plot of FoxM1 mRNA expression level in tumors harboring mutations in p53 or having wild type p53. Datasets were extracted from ONCOMINE database. P values were calculated using Student's t test.

Figure 27:
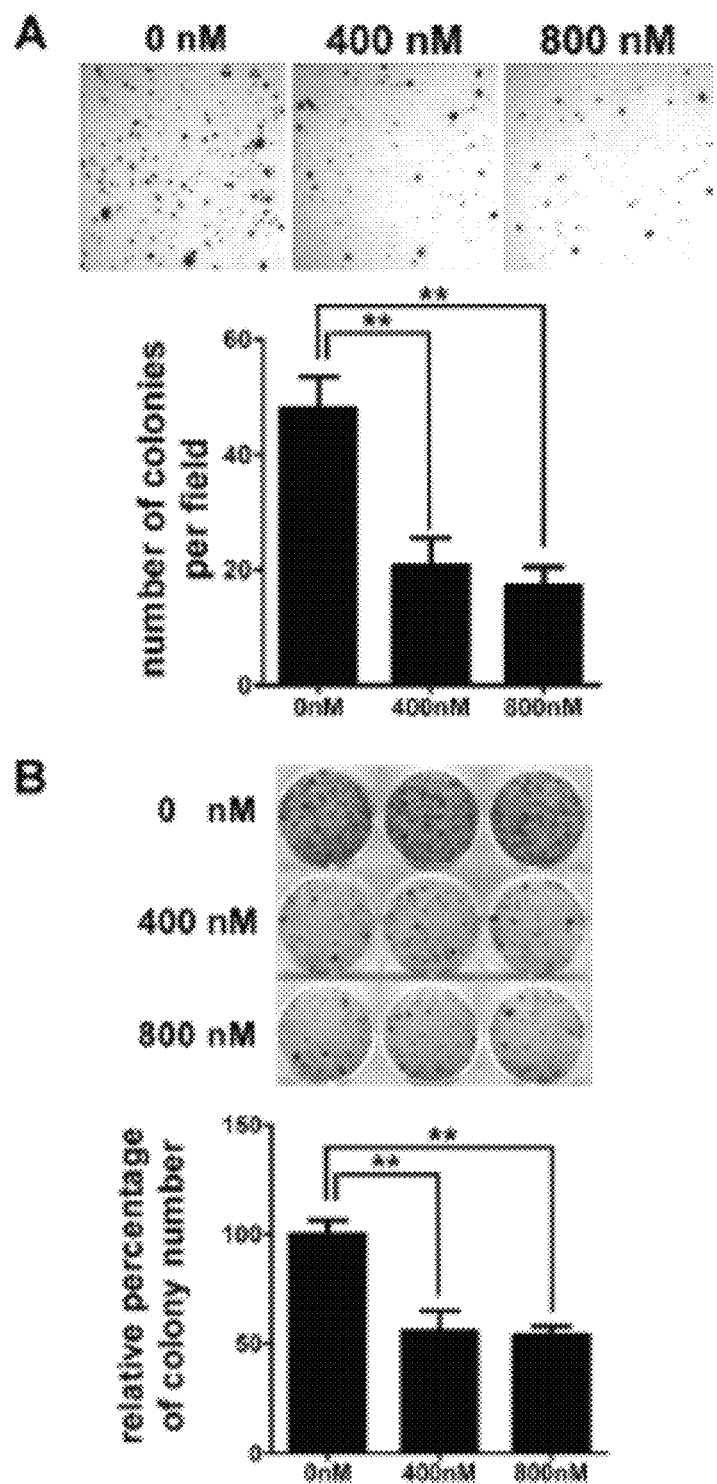

FIG. 27A is representative pictures and quantification of soft agar colonies of CreERT2, Foxm1 fl/fl and p53−/− sarcoma cells following control, 400 nM and 800 nM 4OH-tamoxifen treatment.

FIG. 27B is representative pictures and quantification of foci formation assay of CreERT2, Foxm1 fl/fl and p53−/− sarcoma cells following control, 400 nM and 800 nM 4OH-tamoxifen treatment.

Figure 28:
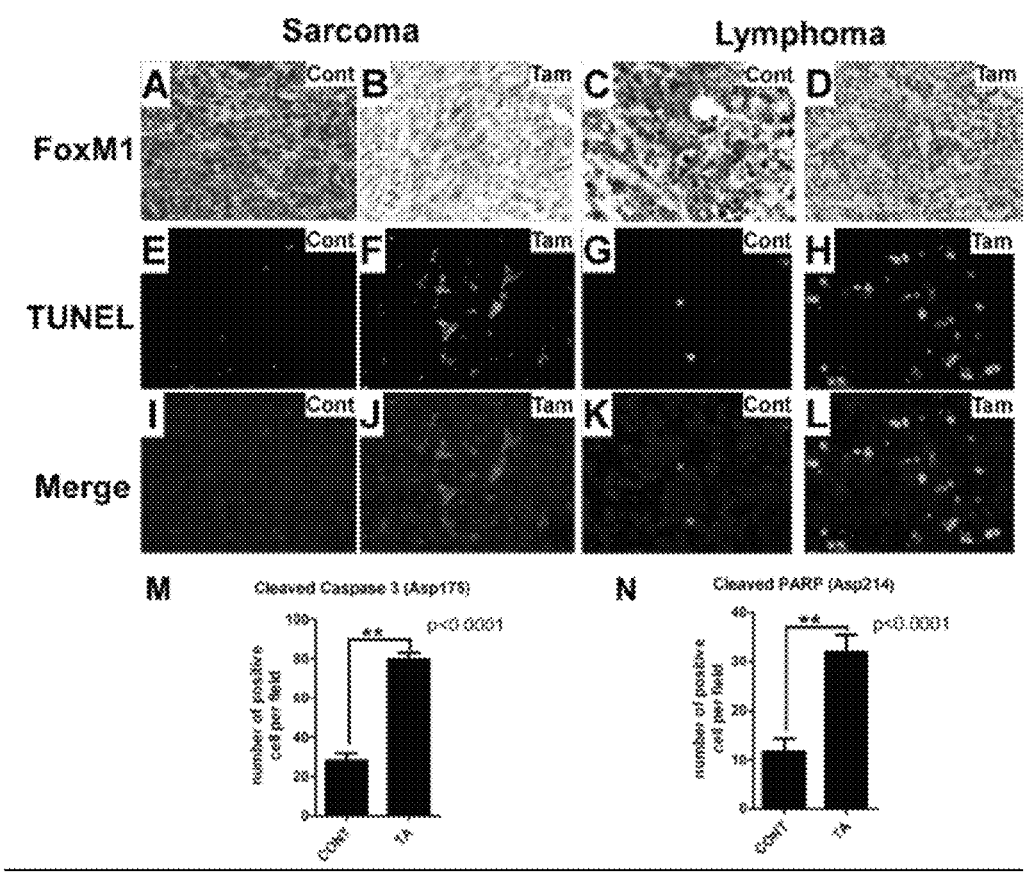

FIGS. 28A-28L are pictures of 5 micron allografted sarcoma tissue and lymphoma tissue treated with tamoxifen or untreated and stained with FoxM1 IHC, TUNEL and/or DAPI. FIGS. 28A-28B illustrate FoxM1 IHC staining of 5 micron allografted sarcoma tissue of control group (FIG. 28A) and tamoxifen treated group (FIG. 28B). FIGS. 28C-28D illustrate FoxM1 IHC staining of 5 micron allografted thymic lymphoma tissue of control group (FIG. 28C) and tamoxifen treated group (FIG. 28D). FIGS. 28E-28F and FIGS. 28I-28J illustrate representative TUNEL and DAPI staining of tumor sections from the subcutaneously inoculated CreERT2 Foxm1 fl/fl and p53−/− sarcoma after tamoxifen or control treatment. FIGS. 28G-28H and FIGS. 28K-28L illustrate representative TUNEL and DAPI staining of tumor sections from the subcutaneously inoculated CreERT2 Foxm1 fl/fl and p53−/− thymic lymphoma after tamoxifen or control treatment.

FIG. 28M shows quantification of the number of positive cleaved-caspase 3 (Asp175) cells per field of thymic lymphoma.

FIG. 28N shows quantification of number of positive cleaved-PARP (Asp214) cells per field of thymic lymphoma.

FIG. 29A is a graph showing viability of CreERT2 Foxm1 fl/fl and p53−/− thymic lymphoma cells at 0 h and 24 hours following non, 5 µM of ARF 26-44 peptide, 5 µM of ARF 37-44 peptide or PBS treatment.

FIG. 29B shows the foci formation of CreERT2 Foxm1 fl/fl and p53−/− sarcoma cells following PBS, 25 µM of ARF 27-44 peptide, or ARF 36-44 peptide treatment.

FIG. 29C is pictures showing cleaved-caspase 3 staining of CreERT2 Foxm1 fl/fl and p53−/− sarcoma cells 24 hours after 25 µM of ARF 27-44 peptide treatment.

DETAILED DESCRIPTION OF THE PREFERRED EMBODIMENTS

Conventional techniques well known to those with skill in the art were used for recombinant DNA production, oligonucleotide synthesis, and tissue culture and cell transformation (e.g., electroporation, lipofection) procedures. Enzymatic reactions and purification techniques were performed according to manufacturers' specifications or as commonly accomplished in the art or as described herein. The techniques and procedures were generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, molecular biology, genetic engineering, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Unless otherwise required by context, singular terms shall include pluralities and plural terms shall include the singular.

DEFINITIONS

As utilized in accordance with the present disclosure, the following terms, unless otherwise indicated, shall be understood to have the following meanings:

The term "isolated protein" referred to herein means a protein encoded by a nucleic acid including, inter alia, genomic DNA, cDNA, recombinant DNA, recombinant RNA, or nucleic acid of synthetic origin or some combination thereof, which (1) is free of at least some proteins with which it would normally be found, (2) is essentially free of other proteins from the same source, e.g., from the same cell or species, (3) is expressed by a cell from a different species, (4) has been separated from at least about 50 percent of polynucleotides, lipids, carbohydrates, or other materials with which it is naturally found when isolated from the source cell, (5) is not linked (by covalent or noncovalent interaction) to all or a portion of a polypeptide to which the "isolated protein" is linked in nature, (6) is operatively linked (by covalent or noncovalent interaction) to a polypeptide with which it is not linked in nature, or (7) does not occur in nature. Preferably, the isolated protein is substantially free from other contaminating proteins or polypeptides or other contaminants that are found in its natural environment that would interfere with its therapeutic, diagnostic, prophylactic or research use.

The terms "polypeptide" or "protein" is used herein to refer to native proteins, that is, proteins produced by naturally-occurring and specifically non-recombinant cells, or by genetically-engineered or recombinant cells, and comprise molecules having the amino acid sequence of the native protein, or sequences that have deletions, additions, and/or substitutions of one or more amino acids of the native sequence. The terms "polypeptide" and "protein" specifically encompass FoxM1B protein, or species thereof that have deletions, additions, and/or substitutions of one or more amino acids of FoxM1B having at least one functional property of the FoxM1B protein. In addition, the terms "polypeptide" and "protein" specifically encompass peptides that can inhibit FoxM1B activity, including the (D-Arg)$_9$-p19$^{ARF}$ 26-44 peptide (SEQ ID NO: 10; rrrrrrrrrKFVRSRRPRTASCALAFVN), the p19$^{ARF}$ 26-44 peptide (SEQ ID NO: 11; KFVRSRRPRTASCALAFVN), and the p19$^{ARF}$ 26-55 peptide (SEQ ID NO: 12; KFVRSRRPRTASCALAFVNMLLRLERILRR), or species thereof that have deletions, additions, and/or substitutions of one or more amino acids of SEQ ID NO: 10, SEQ ID NO: 11, or SEQ ID NO: 12 having the ability to inhibit FoxM1B activity.

The term "naturally-occurring" as used herein refers to an object that can be found in nature, for example, a polypeptide or polynucleotide sequence that is present in an organism (including a virus) that can be isolated from a source in nature and which has not been intentionally modified by man. The term "naturally occurring" or "native" when used in connection with biological materials such as nucleic acid molecules, polypeptides, host cells, and the like, refers to materials which are found in nature and are not manipulated by man. Similarly, "recombinant," "non-naturally occurring" or "non-native" as used herein refers to a material that is not found in nature or that has been structurally modified or synthesized by man.

As used herein, the twenty conventional amino acids and their abbreviations follow conventional usage. See IMMUNOLOGY—A SYNTHESIS, 2nd Edition, (E. S. Golub and D. R. Gren, Eds.), 1991, Sinauer Associates, Sunderland, Mass., which is incorporated herein by reference for any purpose.

FOXM1B, provides an attractive target for anti-cancer therapies because FoxM1B expression typically declines during normal aging (see co-owned U.S. patent application US 2004-0109844 A1, filed Aug., 28 2003, incorporated by reference herein). Thus, FoxM1B provides a selective target that is more active in tumor cells than in normal cells, particularly terminally-differentiated, aged or aging normal cells that surround a tumor, allowing tumor cells to be treated while minimizing the deleterious side-effects of such compounds on normal cells.

In a specific embodiment, the invention provides a polypeptide that inhibits FoxM1B activity in a tumor cell wherein the polypeptide is modified at the N-terminus, at the C-terminus, or at both the N terminus and the C terminus. In order to remove electric charge from polypeptide ends, the polypeptides can be modified by N-terminal acetylation and/or C-terminal amidation. In some embodiments, the modifications can help the polypeptide mimic uncharged natural peptides. In other embodiments, the modified ends are blocked against synthetase activities. In other embodiments, the modified polypeptide has the amino acid sequence of SEQ ID NO:19. Other known modifications to the N and C termini of a polypeptide can also be used according to the invention. In another embodiment, the N and/or C termini of the polypeptide are modified such that polypeptide is less likely or more likely to cyclize. Cyclization of polypeptides has been shown to affect the structural rigidity of the polypeptide. In one embodiment, a linker is provided to facilitate the cyclization of the polypeptide In some embodiments, the polypeptide is modified by amidation. Many bioactive peptides have carboxyl terminal alpha-amide residues. Presence of the alpha-amide can be critical for biological activity. Amidation of peptides can enhance activity of certain polypeptides. Polypeptide amidation is known to one of ordinary skill in the art. Many of the precursor proteins to amidated peptides contain the amino acid sequence -X-Gly-Basic-Basic- where X is the residue that becomes amidated in the mature peptide and the basic residues can be lysine or arginine. Briefly, in a first reaction step the glycine is oxidized to form alpha-hydroxy-glycine. The oxidized glycine cleaves into the C-terminally amidated peptide and an N-glyoxylated peptide. Typically the resulting sequence is —X—NH$_2$. Any combination of these recognized sequences is contemplated by the invention.

In other embodiments, the polypeptide is modified by acetylation. Acetylation occurs when a polypeptide is modified by the attachment of at least one acetyl group, generally at the N-terminus. The acetylation reaction is known to one of ordinary skill in the art, and can be performed, for example, using an acidic anhydride. In some embodiments, the acetylated peptides can serve as optimized enzyme substrates.

Peptide analogs are commonly used in the pharmaceutical industry as non-peptide drugs with properties analogous to those of the template peptide. These types of non-peptide compound are termed "peptide mimetics" or "peptidomimetics." (See Fauchere, 1986, *Adv. Drug Res.* 15: 29; Veber and Freidinger, 1985, *TINS* p. 392; and Evans et al., 1987, *J. Med. Chem.* 30: 1229, which are incorporated herein by reference for any purpose.) Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage such as: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, conformationally-constrained peptides comprising a consensus sequence or a substantially identical consensus sequence variation may be generated by methods known in the art (Rizo and Gierasch, 1992, *Ann. Rev. Biochem.* 61: 387), incorporated herein by reference for any purpose); for example, by adding internal cysteine residues capable of forming intramolecular disulfide bridges which cyclize the peptide.

The term "polynucleotide" as used herein means a polymeric form of nucleotides that are at least 10 bases in length. In certain embodiments, the bases may be ribonucleotides or deoxyribonucleotides or a modified form of either type of nucleotide. The term includes single and double stranded forms of DNA.

In one embodiment, the invention provides methods for inhibiting proliferation of a tumor cell comprising the step of inhibiting FoxM1B activity in the tumor cell. Several methods of inhibiting FoxM1B activity can be used to accomplish the methods of the invention. For example, FoxM1B activity in a cell can be inhibited by causing FoxM1B protein to localize in the cytoplasm, rather than in the nucleus. Causing FoxM1B to localize in the cytoplasm can be accomplished, for example, by contacting a cell with a compound that causes FoxM1B to translocate from the nucleus to the cytoplasm, or that sequesters FoxM1B in the cytoplasm and prevents FoxM1B from translocating from the cytoplasm to the nucleus.

In another embodiment, the inhibitor comprises a polypeptide. In another aspect, the invention provides a modified polypeptide that inhibits FoxM1B activity in a tumor cell. In a preferred embodiment, the polypeptide is isolated.

In certain embodiments, the polypeptide is a chimeric protein. In other embodiments, the polypeptide comprises a viral protein or a fragment thereof. In one embodiment, the polypeptide comprises the HIV Tat peptide. In another embodiment, the polypeptide comprises the HIV Tat peptide of SEQ ID NO:17. In another embodiment, the inhibitor comprises a nine-D-Arg peptide of SEQ ID NO:18. In another embodiment, the inhibitor comprises a p19$^{ARF}$ peptide fragment comprising amino acid residues KFVRSR-RPRTASCALAFVN (SEQ ID NO:16). In a preferred embodiment, the polypeptide comprises (1) a p19$^{ARF}$ peptide fragment comprising amino acid residues KFVRSR-RPRTASCALAFVN (SEQ ID NO:16), and (2) an HIV Tat peptide of SEQ ID NO:17. In another embodiment, the polypeptide comprises (1) a p19$^{ARF}$ peptide fragment comprising amino acid residues KFVRSRRPRTASCALAFVN (SEQ ID NO:16), and (2) a nine-D-Arg peptide of SEQ ID NO:18 that is covalently linked to the N-terminus of the p19$^{ARF}$ peptide fragment. In other embodiments, the polypeptide has the amino acid sequence of SEQ ID NO:19. Amino acid sequences are provided in Table 5.

The polypeptide can be modified at the N-terminus, at the C-terminus or at both the N terminus and the C terminus. Modifications can comprise acetylation, amidation, or any of the other known modifications known in the art and as described. In yet another embodiment, the inhibitor comprises an isolated modified polypeptide that inhibits FoxM1B activity in a tumor cell, said polypeptide comprising (1) a p19$^{ARF}$ peptide fragment comprising amino acid residues (SEQ ID NO:16), and (2) an HIV Tat peptide of SEQ ID NO:17 or a nine-D-Arg peptide of SEQ ID NO:18 that is covalently linked to the N-terminus of the p19$^{ARF}$ peptide fragment, wherein the polypeptide is modified at the N-terminus, at the C-terminus or at both the N terminus and the C terminus.

In one embodiment of the invention, an effective inhibitor of FoxM1B activity causes at least about 50% reduction in FoxM1B activity. Preferably, an effective inhibitor of FoxM1B activity causes at least about 80% reduction in FoxM1B activity. Most preferably, an inhibitor of FoxM1B activity causes at least about 90% reduction in FoxM1B activity.

Assaying for nuclear localization and expression of FoxM1B protein can be accomplished by any method known the art. For example, immunohistochemistry using detectably-labeled primary anti-FoxM1B antibodies, or unlabeled primary anti-FoxM1B and detectably-labeled secondary antibodies (for example, labeled with fluorescent markers, such as fluorescein isothiocyanate, FITC), can be used to visualize FoxM1B protein localization, inter alia, by fluorescence microscopy. Alternative labels, such as radioactive, enzymatic and hapten labels, are within the scope of this invention.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins can be used that are known in the art. Examples of labels for polypeptides include, but are not limited to, the following: radioisotopes or radionuclides (e. $^{3}$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, β-galactosidase, luciferase, alkaline phosphatase), chemiluminescent groups, biotin, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths (such as —(CH$_2$)$_n$—, n=1-50, more preferably 1-20) to reduce steric hindrance.

In certain embodiments, the invention provides a method of inhibiting tumor growth in an animal comprising inhibiting FoxM1B activity in a tumor cell in the animal, for example, by administering to the animal, which has at least one tumor cell present in its body, a therapeutically effective amount of a compound that inhibits FoxM1B activity.

In other embodiments, the invention provides a method of inhibiting tumor growth wherein the tumor has a loss-of-function p53 mutation. Loss-of-function of p53 confers resistance to apoptosis, because p53 stimulates expression of several pro-apoptotic genes, including Puma, Noxa, Bax, Bad, DR4, DR5, Apaf1, Caspase 6 and others (Kuribayashi, et al., 2011, *Cell Cycle.* 10: 2380-2389). P53 also represses expression of anti-apoptotic genes, such as Survivin (Mirza et al., 2002, *Oncogene,* 21: 2613-2622). It is noteworthy that p53 also stimulates several DNA repair genes (Sengupta & Harris, 2005, *Nat Rev Mol Cell Biol,* 6: 44-55). In the absence of p53, reduced DNA repair and apoptosis lead to the accumulation of mutant cells, which contribute to tumor development. For example, p53-null mice, spontaneously develop lymphomas and sarcomas (Donehower, et al., 1992, *Nature,* 356: 215-221). P53 also stimulates expression of the cell cycle inhibitor p21 (Agarwal, et al., 1995, *PNAS,* 92: 8493-8497) and represses FOXM1 (Barsotti & Prives, 2009, *Oncogene,* 28: 4295-4305; Pandit et al., 2009, *Cell Cycle,* 8: 3425-3427), contributing to cell cycle arrest following DNA damage.

In certain embodiments, the invention provides pharmaceutical compositions comprising a therapeutically effective amount of a compound that inhibits FoxM1B expression, nuclear localization or expression and or nuclear localization in mammalian cells together with a pharmaceutically acceptable diluent, carrier, solubilizer, emulsifier, preservative and/or adjuvant. In other embodiments, the invention provides pharmaceutical compositions that comprise a therapeutically effective amount of a compound that inhibits FoxM1B expression in mammalian cells and also induces FoxM1B protein to translocate into the cytoplasm from the nucleus of tumor cells together with a pharmaceutically acceptable diluent, carrier, solubilizer, emulsifier, preservative and/or adjuvant. Such compounds can be identified in screening methods of the invention. The invention further provides pharmaceutical compositions comprising a peptide having an amino acid sequence as set forth in SEQ ID NO: 10, SEQ ID NO: 11, or SEQ ID NO: 12. In other aspects, the pharmaceutical composition comprises a peptide comprising a p19$^{ARF}$ peptide fragment comprising amino acid residues KFVRSR-RPRTASCALAFVN (SEQ ID NO:16), and an HIV Tat peptide of SEQ ID NO:17. In another embodiment, the pharmaceutical composition comprises a peptide a p19$^{ARF}$ peptide fragment comprising amino acid residues KFVRSR-RPRTASCALAFVN (SEQ ID NO:16), and a nine-D-Arg peptide of SEQ ID NO:18. In some embodiments, the pharmaceutical composition comprises a peptide wherein the nine-D-Arg peptide of SEQ ID NO:18 or the HIV Tat peptide of SEQ ID NO:17 is covalently linked to the N-terminus of the p19$^{ARF}$ fragment. In other embodiments, the pharmaceutical composition comprises a peptide having the amino acid sequence of SEQ ID NO:19.

In another aspect, the pharmaceutical composition is a peptide modified at the N-terminus, at the C-terminus, or at both the N terminus and the C terminus. In certain embodiments, the pharmaceutical composition is a peptide modified by acetylation. In other embodiments, the pharmaceutical composition is a peptide modified by amidation. In still other embodiments, the pharmaceutical composition is a peptide modified by both acetylation and amidation.

The term "agent" is used herein to denote a chemical compound, a mixture of chemical compounds, a biological macromolecule, or an extract made from biological materials.

The term "pharmaceutical composition" as used herein refers to a composition comprising a pharmaceutically acceptable carrier, excipient, or diluent and a chemical compound, peptide, or composition as described herein that is capable of inducing a desired therapeutic effect when properly administered to a patient.

The term "therapeutically effective amount" refers to the amount of growth hormone or a pharmaceutical composition of the invention or a compound identified in a screening method of the invention determined to produce a therapeutic response in a mammal. Such therapeutically effective amounts are readily ascertained by one of ordinary skill in the art and using methods as described herein.

As used herein, "substantially pure" means an object species that is the predominant species present (i.e., on a molar basis it is more abundant than any other individual species in the composition). In certain embodiments, a substantially purified fraction is a composition wherein the object species comprises at least about 50 percent (on a molar basis or on a weight or number basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (wherein contaminating species cannot be detected in the composition by conventional detection methods) wherein the composition consists essentially of a single macromolecular species.

The term "patient" includes human and animal subjects.

As used herein, the terms "tumor growth" and "tumor cell proliferation" are used to refer to the growth of a tumor cell. The term "tumor cell" as used herein refers to a cell that is neoplastic. A tumor cell can be benign, i.e. one that does not form metastases and does not invade and destroy adjacent normal tissue, or malignant, i.e. one that invades surrounding tissues, is capable of producing metastases, may recur after attempted removal, and is likely to cause death of the host. Preferably a tumor cell that is subjected to a method of the invention is an epithelial-derived tumor cell, such as a tumor cell derived from skin cells, lung cells, intestinal epithelial cells, colon epithelial cells, colorectal cells, testes cells, breast cells, prostate cells, brain cells, pancreas cells, bone marrow cells, blood lymphocytes, ovary cells or thymus cells.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, $18^{th}$ Edition, (A. R. Gennaro, ed.), 1990, Mack Publishing Company.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions may influence the physical state, stability, rate of in vivo release and rate of in vivo clearance of the antibodies of the invention.

The primary vehicle or carrier in a pharmaceutical composition is aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the FoxM1B-inhibiting product may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound identified in a screening method of the invention is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may be formulated for inhalation. In these embodiments, a compound identified in a screening method of the invention or a FoxM1B inhibitor disclosed herein is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

The pharmaceutical compositions of the invention can be delivered through the digestive tract, such as orally. The preparation of such pharmaceutically acceptable compositions is within the skill of the art. A FoxM1B inhibitor disclosed herein or compounds of the invention that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the FoxM1B inhibitor disclosed herein or compound identified in a screening method of the invention. Diluents, flavorings, low melting point waxes, vegetable oils, lubricants, suspending agents, tablet disintegrating agents, and binders may also be employed.

A pharmaceutical composition may involve an effective quantity of a FoxM1B inhibitor disclosed herein or a compound in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving a FoxM1B inhibitor disclosed herein or compounds of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, *Biopolymers* 22: 547-556), poly (2-hydroxyethyl-methacrylate) (Langer et al., 1981, *J. Biomed. Mater. Res.* 15: 167-277) and Langer, 1982, *Chem. Tech.* 12: 98-105), ethylene vinyl acetate (Langer et al., id.) or poly-D-(−)-3-hydroxybutyric acid (EP 133,988). Sustained release compositions may also include liposomes, which can be prepared by any of several methods known in the art. See e.g., Eppstein et al., 1985, *Proc. Natl. Acad. Sci. USA* 82: 3688-3692; EP 036,676; EP 088,046 and EP 143, 949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The present invention is directed to kits for producing a single-dose administration unit. Kits according to the invention may each contain both a first container having a dried protein compound identified in a screening method of the invention and a second container having an aqueous formulation, including for example single and multi-chambered pre-filled syringes (e.g., liquid syringes, lyosyringes or needle-free syringes).

The effective amount of a pharmaceutical composition of the invention to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the pharmaceutical composition is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

The dosing frequency will depend upon the pharmacokinetic parameters of a FoxM1B inhibitor disclosed herein in the formulation. For example, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In certain embodiments, it may be desirable to use a FoxM1B inhibitor disclosed herein or pharmaceutical compositions thereof in an ex vivo manner. In such instances, cells, tissues or organs that have been removed from the patient are exposed to pharmaceutical compositions of the invention after which the cells, tissues and/or organs are subsequently implanted back into the patient.

Pharmaceutical compositions of the invention can be administered alone or in combination with other therapeutic agents, in particular, in combination with other cancer therapy agents. Such agents generally include radiation therapy or chemotherapy. Chemotherapy, for example, can involve treatment with one or more of the following agents: anthracyclines, taxol, tamoxifene, doxorubicin, 5-fluorouracil, and other drugs known to one skilled in the art.

The following Examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

EXAMPLES

Example 1

Generation of Conditional FoxM1B Knockout Mice

Figure 2:
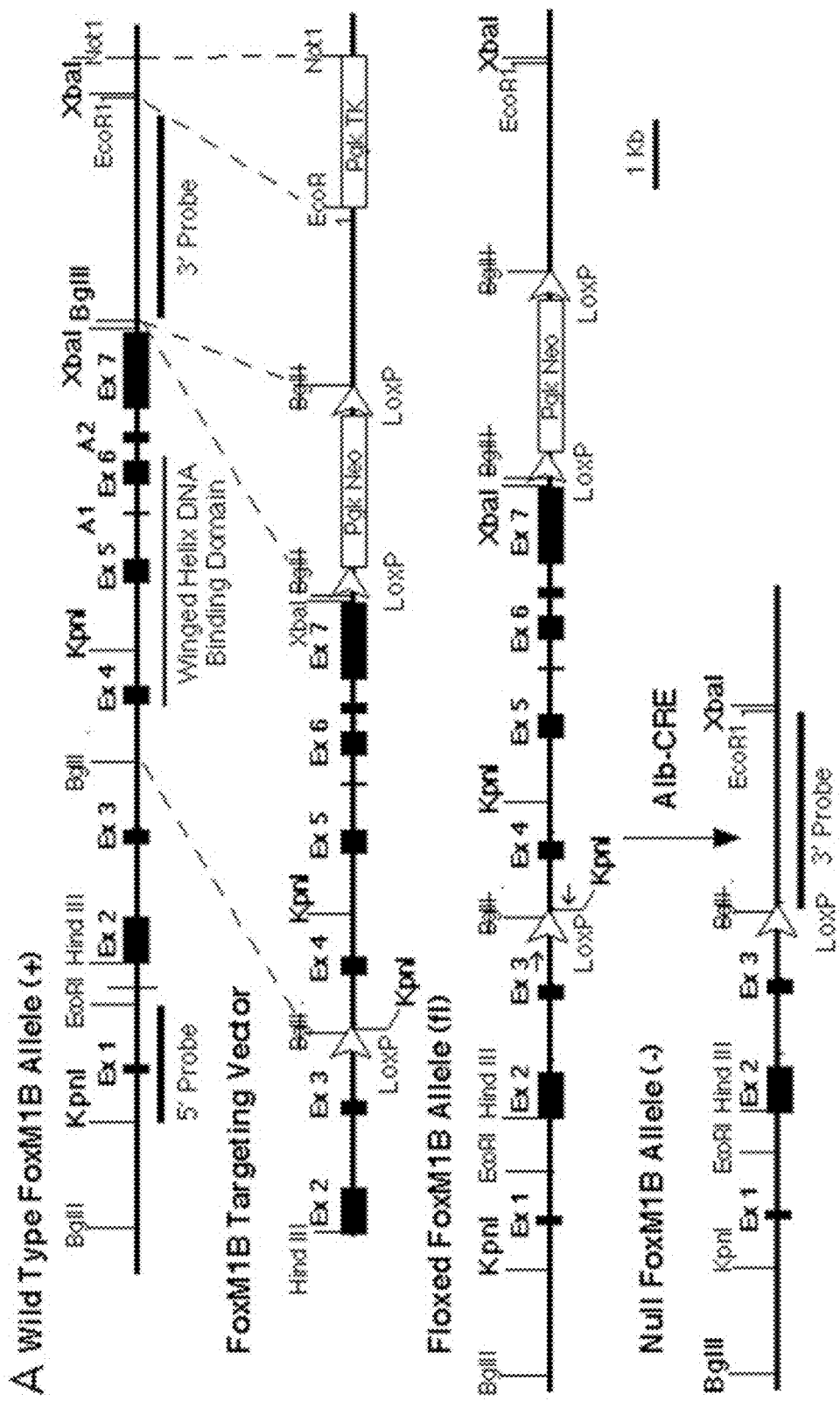
FIG. 2 is a schematic representation of triple-LoxP FoxM1B targeting vector used to generate conditional FoxM1B knockout mice.

FoxM1B knockout mice die immediately after birth. Therefore, to examine the role of FoxM1B in adult tissues, conditional FoxM1B knockout mice were generated using a triple-LoxP FoxM1B targeting vector to create a "Floxed" FoxM1B targeted locus (see FIG. 2 for a schematic diagram of the vector). Cre recombinase-mediated deletion of the FoxM1 genomic sequences spanning the two LoxP sites removes the entire winged helix DNA binding domain and the C-terminal transcriptional activation domain, thereby preventing expression of functional FoxM1 isoforms. Following standard electroporation and culture of mouse embryonic stem (ES) cells to select for homologous recombination (G418 and gangcyclovir), homologous recombinants were identified by Southern blotting of ES cell genomic DNA.

Mouse blastocysts were injected with the ES cells comprising the "Floxed" (fl/+) FoxM1B targeted allele, and chimeric mice with germ line transmission were selected. Viable mice homozygous for the "Floxed" (fl/fl) FoxM1B targeted allele were generated in this manner Mice either homozygous (fl/fl) or heterozygous (fl/+) for the FoxM1B (fl) allele were verified by PCR amplification of mouse genomic DNA with primers that flanked the LoxP site. Breeding the albumin promoter Cre recombinase transgene into the FoxM1B (fl/fl) mouse genetic background allowed hepatocyte deletion of the FoxM1B locus within six weeks after birth, which was verified by Southern blot using liver genomic DNA.

Example 2

TTR-FoxM1B Transgenic Livers Display Increased Size of Hepatic Preneoplastic and Neoplastic Nodules To investigate the influence of increased FoxM1B expression on liver tumor formation, wild type (WT) and TTR-FoxM1B transgenic (TG) CD-1 mice were treated for 23 weeks with diethylnitrosamine (DEN)/Phenobarbital (PB) liver tumor induction (Goldfarb et al., 1983, Environ. Health Perspect. 50:149-161; Russell et al., 1996, Mol. Carcinog. 15:183-189; Slagle et al., 1996, Mol. Carcinog. 15:261-269; Tamano et al., 1994, Carcinogenesis 15:1791-1798). Transgenic CD-1 mice were generated using the −3 kb transthyretin (TTR) promoter to constitutively express the FoxM1B transgene (SEQ ID NO: 1 as shown in FIG. 1) in hepatocytes as described (Ye et al., 1999, Mol. Cell Biol., 19: 8570-8580). At 14 days postnatal of age 17 WT and TTR-FoxM1B TG CD-1 mice received a single IP injection of 5 μg of DEN/g body weight (10 μl/g body weight of 0.05% solution of DEN in water). At 4 weeks of age, mice were placed on water containing 0.05% of PB for 21 weeks. The mice were sacrificed at 25 weeks of age, the livers were fixed in paraformaldehyde, paraffin embedded, sectioned and then H&E stained and examined for tumors. The TTR-FoxM1B TG livers exhibited larger preneoplastic and neoplastic nodules (Table 1; greater than 200 μm in size) and hepatocyte proliferation was stimulated in these hepatic nodules as determined by immunohistochemical staining for Ki67 antigen. However, increased FoxM1B levels did not increase the number of hepatic tumor nodules, suggesting that FoxM1B enhanced the growth of hepatic tumors but did not stimulate tumor initiation.

TABLE 1

| | Size of liver tumor | | |
|---|---|---|---|
| | $R \geq 450\ \mu m^a$ | $450\ \mu m > R \geq 200\ \mu m^b$ | $R < 200\ \mu m$ |
| TTR-FoxM1B TG liver | 3.6 ± 1.3 | 20.3 ± 6.1 | 5.7 ± 4.0 |
| Wild Type Liver | 0.3 ± 0.3 | 8.8 ± 2.5 | 38.8 ± 9.4 |

Table 1 shows the mean number±(s.e.m.) of hepatic preneoplastic or neoplastic nodules (adenomas) per cm³ within the range of sizes shown (n=17 for each genotype). As shown in column 2 (a) and 3 (b), values are significantly different from control mice based on the Student's t-test P=0.019 and P=0.0027, respectively.

Example 3

Figure 3:
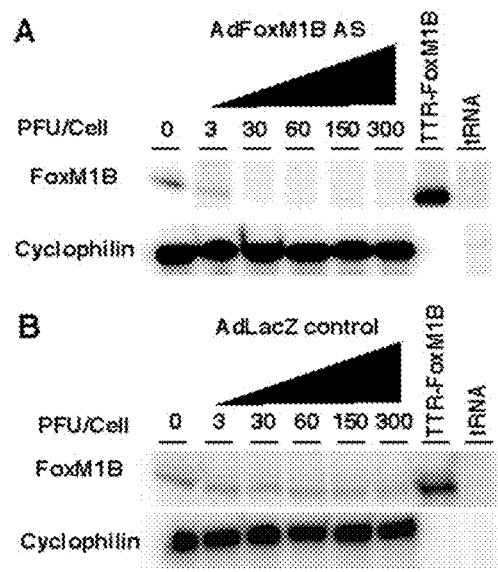
FIGS. 3A and 3B show RNase protection assays (RPA) with a FoxM1B probe after infection of human hepatoma HepG2 cells with Adenovirus expressing antisense human FoxM1B cDNA (AdFoxM1B AS).
Figure 4:
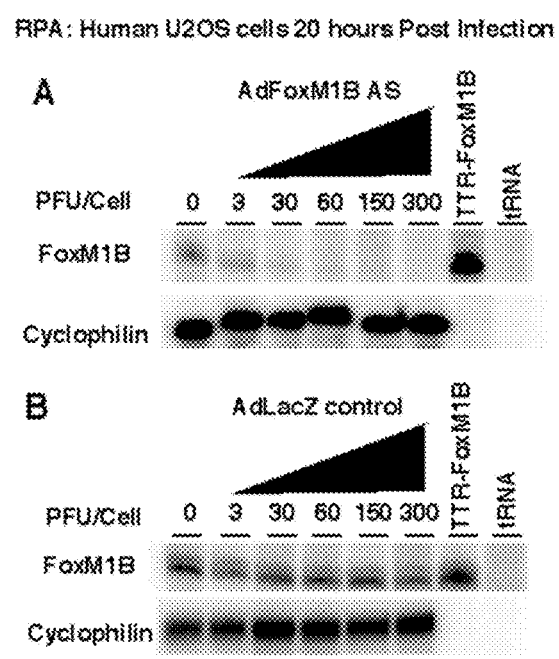

Infection of Proliferating Human Cell Lines with Adenovirus Expressing Antisense Human FoxM1B cDNA Inhibits Expression of Endogenous FoxM1B mRNA Proliferating human hepatoma HepG2 cells were infected with an increasing amounts of plaque forming units (PFU) per cell of either an adenovirus expressing antisense human FoxM1B cDNA (FIG. 3A, AdFoxM1B AS) or Adenovirus expressing bacterial LacZ gene (FIG. 3B, AdLacZ) and total RNA was isolated 20 hours following post infection. Expression of human FoxM1B mRNA was measured using an RNase protection assay (RPA) with a FoxM1B probe as described previously (Ye et al., 1999, Mol. Cell. Biol. 19:8570-8580; Ye et al., 1997, Mol. Cell Biol. 17:1626-1641). These RPA studies demonstrated that AdFoxM1B AS infection at 30 pfu per cell is sufficient to inhibit endogenous FoxM1B expression (FIG. 3A), but AdLacZ control infections did not influence FoxM1B expression (FIG. 3B). Furthermore, AdFoxM1B infection of human osteoblastoma U2OS cells was sufficient to prevent FoxM1B expression in this human tumor cell line as well (FIG. 4). Taken together infection of cells with AdFoxM1B AS is an effective means by which to inhibit FoxM1B expression in tumor cell lines.

Example 4

Generation of FoxM1B Expression Plasmids and Luciferase Reporter Plasmid

The CMV-FoxM1B expression plasmid was generated by PCR amplification of the CMV Human FoxM1B expression plasmid (Ye et al., 1997, *Mol. Cell Biol.* 17:1626-1641) with 5' EcoR1 T-epitope tagged FoxM1B primer: 5'-gcggaattcac-catggctagcatgactggtggacag-caaatgggtTGGCAGAACTCTGTGTCTGAG (SEQ ID NO: 4) and a 3' antisense primer that hybridized to the CMV expression vector SV-40 poly A region: 5'-gtttgtccaattatgtca (SEQ ID NO: 5). The resulting 3.3 KB FoxM1B PCR product was digested with EcoR1 and HindIII, generating the 2.5 KB EcoRI-HindIII T7 tagged FoxM1B cDNA fragment and removing 800 nucleotides from the 3' untranslated region. This FoxM1B cDNA fragment was subsequently cloned in the corresponding sites in the CMV expression vector (Pani et al., 1992, *Mol. Cell Biol.* 12:3723-373245).

A CMV pEGFP-FoxM1B expression plasmid was generated by liberating a 2.5 KB EcoRI-HindIII fragment from the CMV FoxM1B expression vector. The HindIII site was made blunt by T4 polymerase fill in reaction and then the FoxM1B cDNA fragment was cloned into EcoRI-SmaI sites of the pEGFP-C2 expression plasmid (Clontech). The CMV tetracycline operator (CMV-TO) FoxM1B expression plasmid was generated by excising an EcoRI-BamHI fragment from pEGFP-FoxM1B expression plasmid. The BamHI site was made blunt by a T4 polymerase reaction and then the FoxM1B cDNA fragment was cloned into EcoRI and EcoRV sites of the pcDNA4-TO expression plasmid (T-Rex system, Invitrogen).

A 6×FoxM1B/FoxA TATA-Luciferase utilized 6 copies of the FoxM1B/FoxA binding site (TTTGTTTGTTTG; SEQ ID NO: 6) from the cdx-2 promoter region driving expression of the CMV-TATA box luciferase reporter gene as described previously (Rausa et al., 2003, *Mol. Cell. Biol.* 23:437-449; Samadani et al., 1996, *Mol. Cell. Biol.* 16:6273-6284; Ye et al., 1997, *Mol. Cell Biol.* 17:1626-1641).

Example 5

FoxM1B-Dependent Transcription Requires the 596 Cdk Phosphorylation Site and Binding of Cdk1/Cdk2 Proteins Through the FoxM1B LXLXXL Sequence Previous transfection studies demonstrated that the FoxM1B transcriptional activation domain was contained within the carboxyl-terminal 365 to 748 amino acid residues (Ye et. al., 1997. *Mol. Cell. Biol.* 17:1626-1641). Searching the FoxM1B C-terminal sequence for Cdk1/2 consensus phosphorylation sites X-pS/T-P-X-R/K revealed three potential Cdk1/2 sites at residues 585, 596 and 657 in the FoxM1B protein (FIG. 5A). In order to assess the transcriptional function of these potential FoxM1B Cdk1/2 sites, site-directed mutagenesis was used to alter either Thr or Ser residue to an Ala residue to prevent their Cdk phosphorylation in vivo. Transient transfection assays with 6×FoxM1B TATA-luciferase reporter and CMV vectors expressing either WT or Cdk1/2 mutant FoxM1B protein revealed that mutation of Cdk1/2 sites at either 585 or 657 resulted in only a marginal decrease (20% to 30%) in FoxM1B transcriptional activity (FIG. 5B). In contrast, mutation of the FoxM1B 596 Thr residue (FoxM1B T596A) caused an 80% decrease in transcriptional activity, suggesting that this particular Cdk1/2 phosphorylation site plays an important role in FoxM1B-dependent transcription (FIG. 5B). Moreover, FoxM1B was unable to activate expression of the TATA-luciferase control reporter in cotransfection assays, demonstrating that the multimerized FoxM1B binding sites were required for FoxM1B-dependent transcriptional activation (FIG. 5B).

To identify FoxM1B sequences involved in the interaction with Cdk proteins, site-directed mutagenesis was used to convert the Leu 641 residue to an Ala residue thereby disrupting the FoxM1B LXL (639-641) motif shown in FIG. 5A, which has been shown to bind to Cdk-Cyclin proteins as efficiently as the Cyclin-binding Cy (RXL) motif (Takeda et al., 2001, *J Biol Chem* 276:1993-1997; Wohlschlegel et al., 2001, *Mol Cell Biol* 21:4868-4874). Transient transfection assays demonstrated that FoxM1B L641A mutant protein displayed an 80% reduction in transcriptional activity (FIG. 5B). Furthermore, increasing amounts of the CMV FoxM1B L641A expression vector inhibited transcriptional activity of the WT FoxM1B protein in cotransfection assays, suggesting that the CMV FoxM1B L641A mutant protein functioned as a dominant negative inhibitor. Moreover, both GFP-T7-FoxM1B L641A and GFP-T7-FoxM1B T596A mutant proteins are retained in the nucleus (FIG. 4A-C), indicating that their diminished transcriptional activity was not due to inhibition of nuclear localization.

To determine whether the FoxM1B T596A or FoxM1B L641A mutant proteins exhibited diminished protein association with either the Cdk1 or Cdk2 protein, co-immunoprecipitation (Co-IP) experiments were performed with protein extracts prepared from U2OS cells transfected with either CMV T7-FoxM1B WT or mutant expression constructs (FIG. 5C). The transfected U2OS cell extracts were Co-IP with either Cdk1 or Cdk2 antibody and then FoxM1B protein was visualized by Western blot analysis with the T7 epitope Tag monoclonal antibody. These studies demonstrated that CMV T7-FoxM1B L641A mutant protein was unable to interact with either Cdk1 or Cdk2 proteins, whereas the FoxM1B mutant proteins disrupted in each of the Cdk1 phosphorylation sites could efficiently associate with the Cdk proteins (FIG. 5C). These results suggested that retention of the second Leu residue within the LXL sequence was essential for interaction between FoxM1B and Cdk proteins, and that FoxM1B binding of either Cdk1 or Cdk2 Cyclin protein complexes was required for its transcriptional activity.

To examine whether the Cdk1-Cyclin B complex phosphorylates the FoxM1B protein, Co-immunoprecipitation (Co-IP) Cdk1 in vitro kinase assays were performed with $^{32}P$ labeled y-ATP. Protein extracts prepared from U2OS cells transfected with either CMV GFP-T7-FoxM1B WT or GFP-T7-FoxM1B Cdk mutant expression vectors were co-immunoprecipitated with Cdk-1 antibody and were then used for radioactive Cdk1 in vitro kinase assay. The proteins phosphorylated in the Co-IP Cdk1 in vitro kinase reaction were resolved on SDS-PAGE and visualized by autoradiography. Consistent with reduced transcriptional activity, the Cdk1 Co-IP kinase assay demonstrated that GFP-T7-FoxM1B T596A mutation exhibited reduced phosphorylation by the Cdk1 protein, whereas Cdk1 phosphorylated the GFP-T7-FoxM1B T585A and GFP-T7-FoxM1B S657A proteins to levels found with the GFP-T7-FoxM1B WT protein (FIG. 5D). As expected, the GFP-T7-FoxM1B L641A mutant protein failed to interact efficiently with Cdk1 protein (FIG. 5C)

and therefore only low levels of FoxM1B L641A mutant protein were available for Cdk1 phosphorylation in the Co-IP Cdk1 kinase assay (FIG. 5D).

To examine Cdk phosphorylation in vivo, protein extracts were prepared from serum stimulated U2OS cells transfected with either CMV T7-FoxM1B WT, CMV T7-FoxM1B T596A or CMV FoxM1B L641A expression constructs. These protein extracts were IP with the T7 antibody and then Western blot analysis with the MPM2 monoclonal antibody was used to determine Cdk phosphorylation in vivo. These results demonstrated that Cdk phosphorylation of T7-FoxM1B WT protein was increased following serum stimulation and that the FoxM1B Thr 596 residue was required for phosphorylation by the Cdk-Cyclin complexes in vivo (FIG. 5E). Furthermore, in vivo Cdk phosphorylation of the T7-FoxM1B L641A mutant protein was significantly reduced (FIG. 5E), suggesting that recruitment of the Cdk-Cyclin complex by the FoxM1B LXL sequence was critical for its efficient Cdk phosphorylation in vivo.

Example 6

FoxM1B-Dependent Transcription is Stimulated by Increased Cdk1 Activity and CBP Co-Activator Levels CMV-FoxM1B and the 6×FoxM1B TATA luciferase constructs were co-transfected with increasing amounts of CMV-DN-Cdk1 or cells were treated with increasing concentration of the pharmacological Cdk1 inhibitor Alsterpaullone (FIG. 6A) to demonstrate that Cdk1 activity is necessary for FoxM1B transcriptional activity. Inhibiting Cdk1 activity with either dominant negative (DN) Cdk1 or a pharmacologically active concentration of Alsterpaullone (1 μM) caused an 80% to 90% reduction in FoxM1B transcriptional activity (FIG. 6C). Neither DN-Cdk1 nor Alsterpaullone (1 μM) altered nuclear localization of transfected CMV GFP-FoxM1B protein (FIGS. 7A, B and E), suggesting that inhibiting Cdk1 activity alone diminished FoxM1B-dependent transcription. Furthermore, co-transfection of CMV WT-Myt1 kinase, which negatively regulates Cdk1 activity through phosphorylation, resulted in a 64% reduction in FoxM1B transcriptional activity (FIG. 6C). Consistent with these findings, stimulation of Cdk1 activity by co-transfection of either CMV Cdc25B or Cdc25C phosphatases enhanced FoxM1B transcriptional activity by 3.4-fold and 1.7-fold, respectfully (FIGS. 6B and 6D). Furthermore, co-transfection of CMV Cdc25B and CMV CBP together significantly augmented CBP-mediated stimulation of FoxM1B transcriptional activity from 1.4-fold to 6.2-fold increase (FIG. 6D). Taken together, these results provided evidence that Cdk1 activity was required to stimulate FoxM1B transcriptional activity.

Example 7

FoxM1B Transcriptional Activity Involves Recruitment of CBP Through Phosphorylation of the FoxM1B 596 Cdk1 Site Co-transfection assays were performed with CMV-CBP or CMV-Adenovirus E1A alone or in combination to determine if FoxM1B transcriptional activity required the CBP co-activator protein. Co-transfection of CMV-CBP stimulated FoxM1B transcriptional activity by 50%, whereas inhibition of CBP function with E1A resulted in a 75% reduction in FoxM1B transcriptional activity (FIG. 8A). These studies suggested that recruitment of the p300/CBP family of coactivator proteins was essential for FoxM1B transcriptional activation.

U2OS cells were transiently transfected with CMV-CBP and either CMV GFP-FoxM1B, CMV GFP-FoxM1B comprising an L641A mutation, or CMV GFP-FoxM1B comprising all T596A mutation to determine if the critical FoxM1B 596 Cdk1 phosphorylation site was required for recruitment of CBP. Protein extracts were prepared 48 hours after transfection, and then used for immunoprecipitation with CBP antibody followed by Western blot analysis with GFP monoclonal antibody. These co-IP experiments demonstrated that both WT and FoxM1B L641A mutant proteins could efficiently interacted with the CBP protein (FIG. 8B). In contrast, disruption of the FoxM1B Cdk1 phosphorylation site at Thr residue 596 significantly diminished FoxM1B's ability to associate with the CBP protein (FIG. 8B). Taken together these results showed that FoxM1B phosphorylation by Cdk1-Cyclin B complex was required for recruitment of the p300/CBP coactivator protein, serving as a mechanism for proliferation-specific stimulation of FoxM1B transcriptional activity.

Example 8

Blocking the Ras-MAPK and PI3K-PDK1 Pathways Diminished FoxM1B Transcriptional Activity, but Inhibiting Akt Did not Influence FoxM1B-Dependent Transcription The role of the MAPK and PI3K pathways in regulating FoxM1B activity was examined using FoxM1B transcription assays performed in U2OS cells that were either treated with the pharmacological MEK1/2 inhibitor U0126 or PI3K inhibitor Ly294002, or co-transfected with CMV DN-RasN17 expression vector (FIG. 9A). These transfection studies demonstrated that inhibition of MEK1/2, PI3K or Ras caused a 70 to 80% reduction in FoxM1B-dependent transcription (FIG. 9C), a finding consistent with the important roles of Ras/MAPK and PI3K/PDK1 pathways in Cdk1-Cyclin B activation. In contrast, blocking the Akt pathway with either CMV DN-Akt or the Akt pharmacological kinase inhibitor did not significantly alter FoxM1B transcriptional activity (FIG. 9C). Furthermore, combining the MEK1/2 (U0126) and PI3K (Ly294002) inhibitors resulted in a 90% reduction in FoxM1B-dependent transcription demonstrating the importance of the Ras/MAPK and PI3K/PDK1 pathway in regulating FoxM1B transcriptional activity (FIG. 9C). Co-transfection of CMV DN-p90Rsk (FIG. 9A) resulted in a 56% reduction in FoxM1B transcriptional activity (FIG. 9C), which was similar to the transcriptional reductions found with CMV WT-Myt1 (FIG. 6C). Addition of the Ras/MEK1/2 or PI3K/Akt pathway inhibitors did not diminish expression (FIG. 9B) or nuclear localization of GFP-FoxM1B protein (FIGS. 7C, D, G and H), suggesting that these inhibitors caused decreases in FoxM1B transcriptional activity. However, co-transfection of DN-p90Rsk resulted in redistribution of a portion of GFP-FoxM1B fluorescence to the periphery of the nucleus (FIG. 7F), suggesting that p90Rsk signaling may influence FoxM1B nuclear localization. Taken together, these studies demonstrated that FoxM1B transcriptional activity required Cdk1-Cyclin B1 activation, which was mediated by growth factor stimulation of the Ras/MAPK and PI3K/PDK1 signaling cascades.

Example 9

Alb-Cre Foxm1b-/- Livers Fail to Develop Hepatic Adenomas or Hepatocellular Carcinomas after DEN/PB Treatment A well-established Diethylnitrosamine (DEN)/Phenobarbital (PB) liver tumor induction protocol (see Tamano et al., 1994, *Carcinogenesis* 15:1791-1798; Sargent et al., 1996, *Cancer Res.* 56:2985-91; Kalinina et al., 2003, *Oncogene* 22:6266-6276) was used to determine whether Foxm1b was required for proliferative expansion during mouse liver tumor formation. A single intraperitoneal (IP) injection of the tumor initiator Diethylnitrosamine (DEN) was given at 14 days postnatally to the entire mouse litter containing both Foxm1b fl/fl (control) and Alb-Cre Foxm1b-/-(experimental) pups. Two weeks later, the mice were placed on drinking water containing 0.05% of the liver tumor promoter Phenobarbital (PB) for the duration of the liver tumor induction experiment.

Eight control Foxm1b fl/fl mice and 11 experimental Alb-Cre Foxm1b-/- mice were sacrificed at 23 weeks of DEN/PB exposure and seven control Foxm1b fl/fl and 13 experimental Alb-Cre Foxm1b-/- mice were sacrificed at 33 weeks following DEN/PB treatment (Table 2).

In addition, rabbit polyclonal antibodies specific to α-fetoprotein (AFP) (Dako Corp., Carpinteria, Calif.) proteins were used for immunohistochemical detection of 5 μm liver sections using methods described previously (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316). AFP and BrdU positive immunofluorescent cells were detected in the Foxm1b fl/fl HCC liver tumors induced by DEN/PB exposure, which identified proliferating AFP-positive hepatocellular carcinoma cells. Fetal hepatocytes express abundant levels of (AFP), its hepatic expression is extinguished postnatally, but AFP expression is reactivated in HCC (Kunnath and Locker, 1983, *Embo J* 2:317-324; Chen et al., 1997, *Crit. Rev Eukaryot Gene Expr* 7:11-41). Thus, these studies suggested that Foxm1b is required for proliferative expansion during tumor development of hepatic adenomas and HCC.

Together, these experiments demonstrated that male Alb-Cre Foxm1b-/- mice were resistant to developing HCC in response to 33 weeks of DEN/PB exposure, a treatment sufficient to induce multiple HCC tumors in male Foxm1b fl/fl mice (Table 2).

Furthermore, control Foxm1b fl/fl and experimental Alb-Cre Foxm1b-/- mice were treated with DEN/PB for 50

TABLE 2

Number of tumors per cm² liver tissue after 23 or 33 weeks of DEN/PB treatment

| DEN/PB & Sex | Foxm1b fl/fl Mice | | | | Alb-Cre Foxm1b -/- Mice | | | |
|---|---|---|---|---|---|---|---|---|
| | [1]# Mice | [2]Adenomas | # Mice | Carcinomas | # Mice | Adenomas | # Mice | Carcinomas |
| 23 weeks Male | 3 | 14.2 ± 5.2 | 3 | 0.5 ± 1.0 | 6 | 0 | 6 | 0 |
| 33 weeks Male | 3 | 11.2 ± 0.6 | 3 | 3.8 ± 0.9 | 7 | 0 | 7 | 0 |
| 23 weeks Female | 5 | 3.5 ± 1.7 | 5 | 0 | 5 | 0 | 5 | 0 |
| 33 weeks Female | 4 | 21.0 ± 6.9 | 4 | 0 | 6 | 0 | 6 | 0 |

[1]# Mice: Number of mice (male or female) analyzed for liver tumors after either 23 or 33 weeks of Diethylnitrosamine (DEN)/Phenobarbital (PB) treatment.
[2]Number of liver tumors per cm² liver tissue ± SD (adenomas or hepatocellular carcinomas greater than 0.1 mm in size) determined from Hematoxylin and Eosin stained liver sections obtained from four different mouse liver lobes.

Livers were harvested from male Foxm1b fl/fl and Alb-Cre Foxm1b-/- mice after 6 weeks of DEN/PB exposure to provide an early time point during liver tumor promotion. Liver sections were histologically stained with Hematoxylin and Eosin (H&E) and hepatocyte DNA replication was determined by immunofluorescent detection of BrdU that had been administered in drinking water 4 days before sacrificing the mice following the procedure described in Ledda-Columbano et al., 2002, *Hepatology* 36:1098-1105. After 23 weeks of DEN/PB treatment, H&E stained liver sections from Foxm1b fl/fl male mice revealed numerous hepatic adenomas with abundant BrdU labeling (Table 2). Highly proliferative hepatocellular carcinomas (HCC) with abundant BrdU labeling were visible in liver sections from each of the male control Foxm1b fl/fl mice following 33 weeks of DEN/PB exposure (Table 2). Furthermore, significant numbers of hyper-proliferative adenomas were found in liver sections from female and male Foxm1b fl/fl mice after 33 weeks of DEN/PB treatment (Table 2). No hepatic adenomas or HCC were detected in male or female Alb-Cre Foxm1b-/- mice at either 23 or 33 weeks following DEN/PB exposure (Table 2). At 6, 23 and 33 weeks following DEN/PB treatment, low levels of BrdU incorporation were found in Foxm1b deficient hepatocytes, which was approximately 30% of BrdU labeling levels found in Foxm1b fl/fl hepatocytes of non-tumor regions following DEN/PB exposure.

weeks to determine whether Foxm1b deficient livers were resistant to a prolonged hepatic tumor induction protocol. After 50 weeks of DEN/PB exposure, all nine female Alb-Cre Foxm1b-/- mice were devoid of any liver tumors, whereas HCC tumors were found in all four control female livers with one additional control female mouse dying prematurely. Following 50 weeks of DEN/PB exposure, no liver tumors were found in two out of the four male Alb-Cre Foxm1b-/- mice, while one male mouse exhibited hepatic adenomas and the last male mouse displayed HCC tumors that were negative for Foxm1b protein staining. These studies indicated that following prolonged DEN/PB tumor promotion hepatic tumors were found in a subset of the male Alb-Cre Foxm1b-/- livers, suggesting that they developed secondary mutations that allowed tumor formation bypassing the block in Foxm1b-/- hepatocyte proliferation.

Example 10

Alb-Cre Foxm1b-/- Male Mouse Hepatocytes Exhibited No Elevation in Apoptosis and Increased Hypertrophy in Response to DEN/PB Treatment TUNEL staining of liver sections from DEN/PB treated mice was used to determine whether increased apoptosis contributed to the failure of male Alb-Cre Foxm1b-/- mice to develop liver tumors in response to 33 weeks of DEN/PB treatment. The TUNEL assay was performed using the ApoTag Red in situ apoptosis detection kit from Intergen (Purchase, N.Y.) according to the manufacturer's recommendations. No difference was found in hepatocyte apoptosis between Alb-Cre Foxm1b−/− and Foxm1b fl/fl mice after 6, 23, or 33 weeks of DEN/PB exposure (FIG. 10A-C). These results suggested that the absence of liver tumors in Foxm1b−/− mice following DEN/PB exposure was not due to an increase in hepatocyte apoptosis.

Hypertrophy of the Alb-Cre Foxm1b−/− hepatocytes was significantly increased compared to that of control hepatocytes (non-tumor liver regions) at 23 weeks of DEN/PB exposure (FIG. 10D-E). A centromere-specific FISH probe purchased from Vysis Inc. (Downers Grove, Ill.) was used to hybridize paraffin embedded liver sections according to manufacturer's protocol, demonstrating that Alb-Cre Foxm1b−/− hepatocyte nuclei possessed an increase in hybridizing chromosomes compared to control hepatocyte nuclei at 23 weeks of DEN/PB treatment (FIG. 10E-G). To quantitate this increase in size, the number of DAPI stained hepatocyte nuclei were counted (per 200× field) in Foxm1b fl/fl and Alb-Cre Foxm1b−/− liver sections and the data for each of the time points following DEN/PB exposure was plotted (FIG. 10H). The mean number (±SD) of DAPI positive hepatocyte nuclei per 1000 cells or 200× field by counting the number of positive hepatocyte nuclei using 5 different 200× liver sections from 3 distinct male mice at the indicated times of DEN/PB exposure or untreated. After 23 or 33 weeks of DEN/PB exposure, half the number of hepatocyte nuclei per 200× field was found in Foxm1b−/− livers compared to Foxm1b fl/fl control liver (FIG. 10H). The data suggested that Foxm1b deficient hepatocytes undergo greater hypertrophy and become more polyploid than Foxm1b fl/fl control hepatocytes at 23 and 33 weeks of DEN/PB treatment. These results suggested that Alb-Cre Foxm1b−/− hepatocytes exhibited low levels of DNA replication with a significant reduction in mitosis as was previously found in Foxm1b deficient hepatocytes during liver regeneration and development (Korver et al., 1998, *Nucleic Acids Res* 25:1715-1719; Wang et al., 2002, *Proc Natl Acad Sci USA* 99:16881-16886). Moreover, Alb-Cre Foxm1b−/− hepatocytes displayed normal serum levels of albumin, bilirubin and glucose after 33 weeks of DEN/PB exposure indicating that their livers functioned normally.

Example 11

Figure 11:
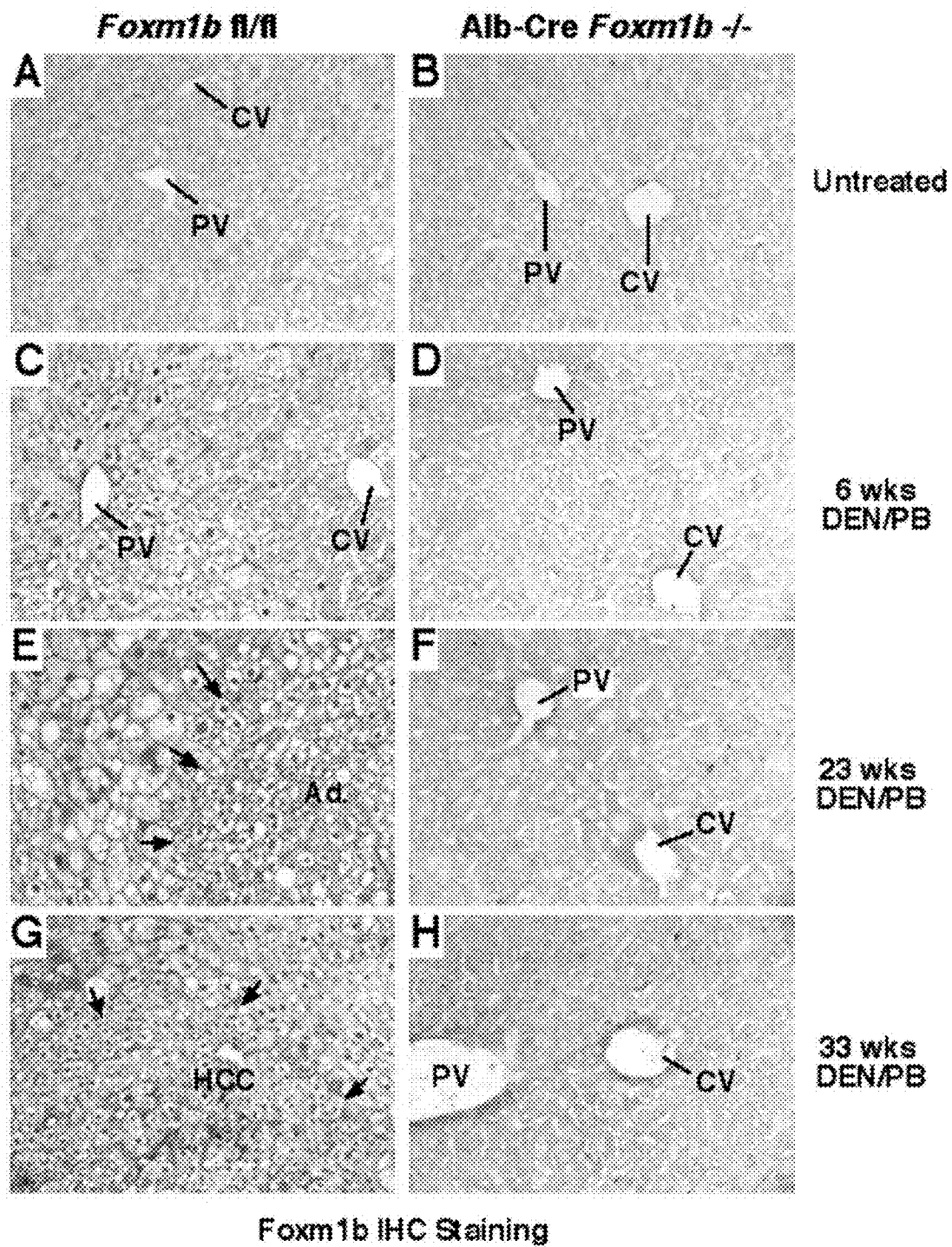

Hepatocyte Expression of Nuclear Foxm1b Protein Increases Prior to Tumor Formation and Continues During Tumor Progression Immunohistochemical staining of liver sections with an antibody specific to Foxm1b protein (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316) demonstrated that untreated hepatocyte nuclei displayed no significant expression of the Foxm1b protein (FIG. 11A-B). Abundant nuclear staining of Foxm1b protein was detected in periportal Foxm1b fl/fl hepatocytes as early as 6 weeks of DEN/PB (FIG. 11C), yet these hepatocytes failed to exhibit abundant BrdU incorporation levels. High levels of nuclear FoxM1B protein persisted in hyper-proliferative liver adenomas and HCC at 23 weeks and 33 weeks following DEN/PB exposure (FIGS. 11E and G). As expected, nuclear staining of FoxM1B protein was not found in Alb-Cre Foxm1b−/− hepatocytes at any of the time points following DEN/PB treatment (FIGS. 11D, F and H), confirming that the Alb-Cre transgene protein efficiently deleted the Foxm1b floxed targeted allele in hepatocytes (Wang et al., 2002, *Proc Natl Acad Sci USA* 99:16881-16886). These studies demonstrated that hepatocyte nuclear levels of FoxM1B were induced in control hepatocytes prior to tumor formation following DEN/PB treatment and that this nuclear expression persisted in hepatic adenomas and HCC.

Example 12

Figure 12:
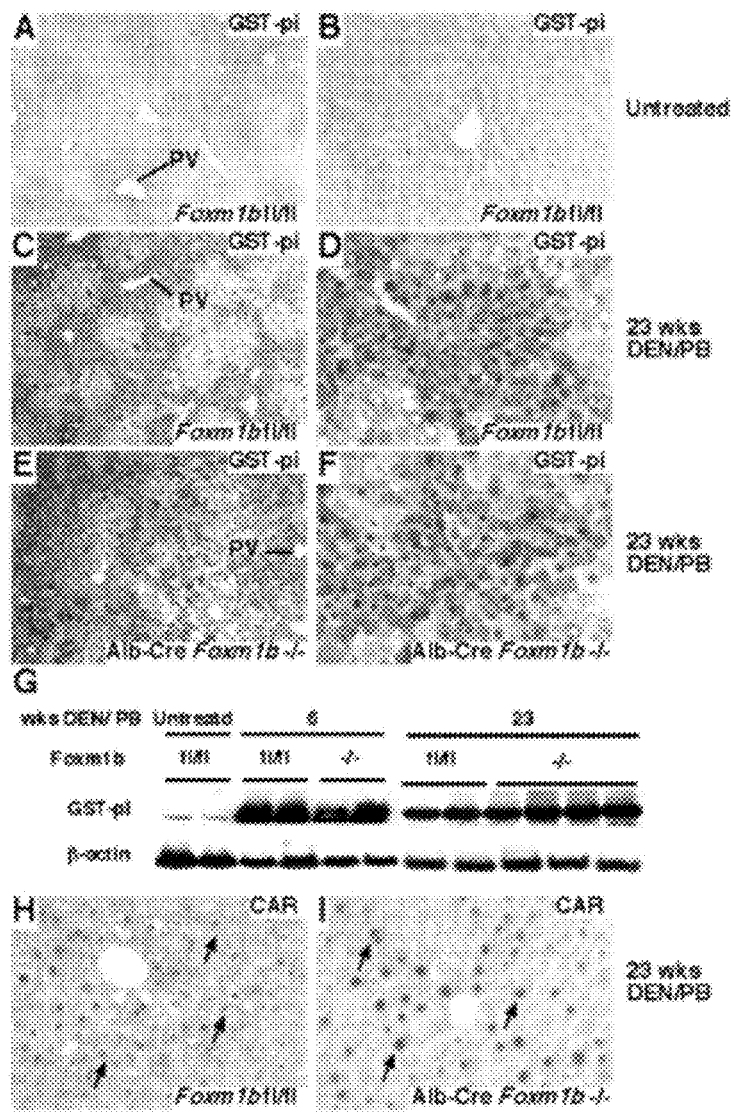

Alb-Cre Foxm1b−/− Livers Exhibit Normal Expression of GST-Pi and CAR Following DEN/PB Treatment Glutathionine-S-transferase placental isoform (GST-pi) is an early marker for "altered enzyme foci" in response to DEN/PB exposure (Hatayama et al., 1993, *Carcinogenesis* 14:537-538). Rabbit polyclonal antibodies specific to GST-pi (Dako Corp., Carpinteria, Calif.) proteins were used for immunohistochemical detection of 5 μm liver sections using methods described previously (Ye et al., 1997, Mol Cell Biol 17:1626-1641; Ye et al., 1999, *Mol. Cell Biol.* 19:8570-8580; Wang et al., 2002, *J. Biol. Chem.* 277:44310-44316). GST-pi expression was not detected in liver sections of untreated control mice (FIG. 12A-B), but both Alb-Cre Foxm1b−/− and Foxm1b fl/fl hepatocytes were strongly immunostained for GST-pi after 23 weeks of DEN/PB treatment (FIG. 12C-F). Western blot analysis demonstrated that hepatic expression of GST-pi protein was induced as early as 6 weeks following DEN/PB treatment in both Alb-Cre Foxm1b−/− and Foxm1b fl/fl livers with continued expression after 23 weeks of DEN/PB exposure (FIG. 12G). Phenobarbital (PB) stimulates nuclear translocation of the constitutive androstane receptor (CAR) nuclear receptor (Chawla et al., 2001, *Science* 294:1866-1870). No difference in nuclear staining of the CAR receptor was found between Foxm1b fl/fl and Alb-Cre Foxm1b−/− hepatocytes following DEN/PB treatment (FIG. 12H-I), indicating that the Foxm1b deficient hepatocytes were still responsive to the PB tumor promoter. Taken together, the data suggest that Alb-Cre Foxm1b−/− livers responded normally to DEN/PB tumor induction and expressed the "altered enzyme foci" GST-pi marker, but that they failed to undergo the proliferation required for tumor progression.

Example 13

Persistent Nuclear Accumulation of the Cdk Inhibitor p27$^{Kip1}$ Protein and Diminished Cdc25B Expression in Alb-Cre Foxm1b−/− Livers Follows DEN/PB Exposure Liver regeneration studies demonstrated that increased expression of Foxm1b protein was associated with reduced hepatocyte nuclear levels of the Cdk inhibitor p27$^{Kip1}$ protein (Wang et al., 2002, *Proc Natl Acad Sci USA* 99:16881-16886; Wang et al., 2002, *J. Biol. Chem.* 277:44310-44316; Krupczak-Hollis et al., 2003, *Hepatology* 38:1552-1562). Consistent with these findings, persistent nuclear accumulation of hepatocyte p27$^{Kip1}$ protein was found only in Alb-Cre Foxm1b−/− liver sections at 36 hours after partial hepatectomy (PHx; FIG. 13A-B). Nuclear expression of p27$^{Kip1}$ protein was examined in mouse liver sections from untreated and DEN/PB treated mice using immunohistochemical staining. Rabbit polyclonal antibodies specific to p27$^{kip1}$ (Cell Signaling, Beverly, Mass.) proteins were used for immunohistochemical detection of 5 μm liver sections using methods described previously (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316). Similar hepatocyte levels of nuclear p27$^{Kip1}$ protein were found in untreated Alb-Cre Foxm1b–/– and Foxm1b fl/fl mice (FIG. 13C-D), a finding consistent with abundant nuclear expression of the Cdk inhibitor p27$^{Kip1}$ protein in quiescent hepatocytes (Kwon et al., 2002, *J Biol Chem* 277:41417-41422). Hepatocyte nuclear staining of p27$^{Kip1}$ protein was significantly diminished in Foxm1b fl/fl hepatocytes beginning at 6 weeks and continuing through 33 weeks after DEN/PB treatment (FIGS. 13E, G, I and M).

Furthermore, nuclear expression of p27$^{Kip1}$ protein was undetectable in hepatic tumor cells at all time points following DEN/PB treatment (FIGS. 13G and I). In contrast, hepatocyte nuclear staining of p27$^{Kip1}$ protein was sustained in Alb-Cre Foxm1b–/– mice at 6, 23 and 33 weeks after DEN/PB exposure (FIGS. 13F, H, J and M). After 50 weeks DEN/PB treatment, nuclear staining of p27$^{Kip1}$ protein was sustained in Female Alb-Cre Foxm1b–/– mouse hepatocytes (FIGS. 13K and N) and these livers were resistant to development of adenomas and HCC. In contrast, male Alb-Cre Foxm1b–/– mouse hepatocytes exhibited nearly undetectable nuclear staining of p27$^{Kip1}$ protein after 50 weeks of DEN/PB exposure (FIGS. 13L and N) and was associated with 50% of the male Alb-Cre Foxm1b–/– mice developing liver tumors. These results suggested that an increase in liver tumor incidence in male mice following prolonged response to DEN/PB treatment was associated with loss of hepatocyte nuclear levels of p27$^{Kip1}$ protein.

Diminished hepatocyte DNA replication in regenerating Alb-Cre Foxm1b–/– livers was associated with increased nuclear levels of the Cdk inhibitor p21$^{Cip1}$ protein (Wang et al., 2002, *Proc Natl Acad Sci USA* 99:16881-16886). Immunostaining of liver sections demonstrated that nuclear expression of p21$^{Cip1}$ protein in Alb-Cre Foxm1b–/– and Foxm1b fl/fl hepatocytes was similar and restricted to hepatocytes surrounding the central vein after 6, 23 or 33 weeks of DEN/PB treatment. The similar expression pattern of nuclear p21$^{Cip1}$ protein in hepatocytes of DEN/PB treated mice suggested that elevated p21$^{Cip1}$ protein levels were unlikely to be involved in suppressing tumor formation in Alb-Cre Foxm1b–/– livers.

Western blot analysis revealed similar levels of total p27$^{Kip1}$ protein in Foxm1b fl/fl and Alb-Cre Foxm1b–/– liver extracts at 6, 23 or 33 weeks following DEN/PB exposure (FIG. 14A). These results suggested that Foxm1b deficiency resulted in sustained hepatocyte levels of nuclear p27$^{Kip1}$ protein after DEN/PB treatment without changing total expression of the p27$^{Kip1}$ protein.

The Western blot was then stripped and probed sequentially with antibodies specific to the Cdk-activating Cdc25B or Cdc25C phosphatases (Santa Cruz Biotech) at a concentration of 1:1000. Foxm1b fl/fl control livers exhibited a transient increase in expression of the M-phase promoting Cdc25B phosphatase protein at 6 weeks after DEN/PB exposure, whereas hepatic levels of Cdc25B protein were significantly diminished in Alb-Cre Foxm1b–/– livers (FIG. 14A). Similar levels of Cdc25C protein are found in liver extracts from Alb-Cre Foxm1b–/– and Foxm1b fl/fl mice after 6 weeks of DEN/PB treatment (FIG. 14A). However, diminished hepatic expression of Cdc25B and Cdc25C proteins is observed at either 23 or 33 weeks after DEN/PB exposure (FIG. 14A). Taken together, the data suggested that decreased proliferation in Alb-Cre Foxm1b–/– hepatocytes was likely due to sustained nuclear levels of Cdk inhibitor p27$^{Kip1}$ protein and diminished expression of the Cdk1-activator Cdc25B.

Example 14

The Cdk Inhibitor p27$^{Kip1}$ Protein Associates with FoxM1B Through the Cdk-Cyclin Complexes and Inhibits its Transcriptional Activity FoxM1B transcriptional activity requires an LXL Cdk docking site (639-641) that recruits either the Cdk2-Cyclin E/A (S-phase) or Cdk1-Cyclin B (G2 phase) complexes to the FoxM1B transcriptional activation domain, which is required for efficient phosphorylation of the FoxM1B Cdk 596 site (Major et al., 2004, *Mol. Cell. Biol.* 24:2649-2661). Retention of this Foxm1b Cdk site at Thr 596 residue was found to be essential for transcriptional activity by mediating phosphorylation dependent recruitment of the CREB Binding Protein (CBP) histone acetyltransferase (Major et al., 2004, *Mol. Cell. Biol.* 24:2649-2661).

Protein extracts were prepared from U2OS cells that were transiently transfected with the CMV p27$^{Kip1}$ and CMV expression constructs containing either WT GFP-Foxm1b or the GFP-FoxM1B L641A mutant that failed to interact with the Cdk-Cyclin complexes (Major et al., 2004, *Mol. Cell. Biol.* 24:2649-2661). These U2OS cell transfected lysates were immunoprecipitated (IP) with the p27$^{Kip1}$ antibody (Cell Signaling, Beverly, Mass.; 1:1000) followed by Western blot analysis with GFP antibody. These Co-IP experiments demonstrated that the p27$^{Kip1}$ protein associated with the WT FoxM1B protein, whereas p27$^{Kip1}$ was unable to bind to the GFP-FoxM1B L641A mutant protein (FIG. 14C). These results suggested that the p27$^{Kip1}$ protein associated with the Cdk-Cyclin complexes, which are recruited by the FoxM1B transcriptional activation domain through the LXL Cdk docking motif (FIG. 14B).

In addition, U2OS cells were transiently transfected with the 6×FoxM1B-TATA-luciferase reporter plasmid (Rausa et al., 2003, *Mol Cell Biol* 20:8264-8282; Major et al., 2004, *Mol. Cell. Biol.* 24:2649-2661) with the CMV WT FoxM1B and p27$^{Kip1}$ expression vectors to determine whether the p27$^{Kip1}$ protein could inhibit Foxm1b transcriptional activity. Transfected cells were harvested at 48 hours after transfection and processed for dual luciferase assays to determine FoxM1B transcriptional activity. Cotransfection of p27$^{Kip1}$ expression vector caused a significant reduction in FoxM1B transcriptional activity (FIG. 14D). This finding was consistent with the ability of the p27$^{Kip1}$ protein to inhibit kinase activity of the Cdk-Cyclin complexes (Polyak et al., 1994, *Genes Dev* 8:9-22; Zerfass-Thome et al., 1997, *Mol Cell Biol* 17:407-415) required for FoxM1B transcriptional activity through Cdk phosphorylation dependent recruitment of the CBP coactivator protein (Major et al., 2004, *Mol. Cell. Biol.* 24:2649-2661).

Example 15

Endogenous p19$^{ARF}$ Tumor Suppressor Associates with FoxM1B Protein in Liver Extracts Prepared from Mice Following 6 Weeks of DEN/PB Exposure Hepatic expression of p19 protein in livers from mice exposed to DEN/PB was examined by Western blot analysis. For Western blotting, 100 μg of total protein extracts prepared from liver following the procedure in Rausa et al., 2000, *Mol Cell Biol* 20:8264-8282) were separated on SDS-PAGE and transferred to PVDF membrane (BioRAD). Rabbit antibodies specific to p19$^{ARF}$ (AB80; GeneTex, San Antonio, Tex.; 1:750) proteins were used as primary antibody. The primary antibody signals were amplified by HRP-conjugated secondary antibodies (Bio-Rad, Hercules, Calif.), and detected with Enhanced Chemiluminescence Plus (ECL-plus, Amersham Pharmacia Biotech, Piscataway, N.J.).

Western Blot analysis demonstrated that hepatic expression of p19 protein was induced at 6 weeks after DEN/PB exposure, but liver expression of p19 was significantly diminished by 23 weeks following DEN/PB exposure (FIG. 15A), a finding consistent with those obtained with other tumors (Sherr and McCormick, 2002, *Cancer Cell* 2:103-112).

Co-immunoprecipitation (Co-IP) assays were performed with liver protein extracts prepared from Foxm1b fl/fl and Alb-Cre Foxm1b−/− mice following either 6 or 23 weeks of DEN/PB treatment (FIG. 15B) to determine whether the p19 tumor suppressor protein associated with the FoxM1B protein. For Co-IP experiments, 500 μg of protein extract prepared from DEN/PB treated liver were immunoprecipitated with p19$^{ARF}$ antibody (AB80; GeneTex, San Antonio, Tex.; 2 μg) followed by Western Blot analysis with mouse antibody FoxM1B protein (1:5000). The signals from the primary antibody were amplified by HRP conjugated anti-mouse IgG (Bio-Rad, Hercules, Calif.), and detected with Enhanced Chemiluminescence Plus (ECL-plus, Amersham Pharmacia Biotech, Piscataway, N.J.). As a positive control, Co-IP experiments were performed with protein extracts prepared from mouse embryo fibroblasts (MEFs) that were cultured in vitro for 12 passages to induce endogenous protein expression of the p19 tumor suppressor (Kamijo et al., 1997, *Cell* 91:649-659). These Co-IP studies demonstrated efficient association between endogenous FoxM1B and p19 proteins in extracts prepared from either Foxm1b fl/fl livers at 6 weeks of DEN/PB exposure or late passage MEFs, but not with liver extracts from Alb-Cre Foxm1b−/− mice (FIG. 15B). Negative controls showed that Foxm1b protein failed to Co-IP with p19 in protein extracts prepared from Foxm1b fl/fl livers at 23 weeks of DEN/PB treatment, which no longer expressed the p19 protein but continued to express Foxm1b protein (FIGS. 15B and 11C).

Example 16

FoxM1B and p19 Cotransfection Assays and Synthesis of (D-Arg)$_9$-p19$^{ARF}$ 26-44 Peptide Human osteosarcoma U2OS cells were maintained in DMEM supplemented with 10% fetal calf serum, 1×Pen/Strep and 1×L-Glutamine (Gibco). For transient transfection, U2OS cells were plated in six-well plates and transfected using Fugene 6 reagent (Roche) according to the manufacturer's protocol. Cells were transfected with 500 ng of CMV WT FoxM1B 1-748 alone or with CMV expression vectors containing either WT T7-p19$^{ARF}$ or N-terminal mutant T7-p19 protein (Δ1-14, Δ15-25, Δ26-37, or Δ26-37+Δ1-14) or V5-TAT-p19$^{ARF}$ 26-44 or V5-TAT-p19$^{ARF}$ 26-55 sequences and with 1.5 μg of a 6×FoxM1B TATA-Luciferase reporter. Ten nanograms of CMV-Renilla luciferase reporter plasmid were included as an internal control to normalize transfection efficiency. Cotransfection assays were also performed with 500 ng of CMV FoxM1B 1-688 and 6×FoxM1B TATA-Luciferase reporter and 10 ng of CMV-*Renilla* internal control. Twenty-four hours post-transfection, cells were prepared for dual luciferase assays (Promega). Luciferase activity was determined as percent of wild type FoxM1B activity following normalization to *Renilla* activity. Experiments were performed at least four times in triplicate and mean±SD determined.

The Sigma-Genosys company (The Woodlands, Tex.) synthesized a (D-Arg)$_9$-p19ARF 26-44 peptide (rrrrrrrrrK-FVRSRRPRTASCALAFVN; SEQ ID NO: 10) containing nine D-Arg residues (SEQ ID NO: 14) at the N-terminus, which has been demonstrated to enhance cellular uptake of polypeptides (Wender et al., 2000, *Proc Natl Acad Sci USA* 97:13003-13008). The (D-Arg)$_9$-p19ARF 26-44 peptide was tagged with a fluorescent Lissamine (TRITC) on the N-terminus and acetylated at the C-terminus and was purified by high-pressure liquid chromatography (Sigma-Genosys). Cotransfection assays were also performed with 500 ng of CMV FoxM1B 1-688, 6×FoxM1B TATA-Luciferase reporter and 10 ng of CMV-Renilla internal control. The transfected U2OS cells were treated with 12 μM of the p19$^{ARF}$ rrrrrrrrrK-FVRSRRPRTASCALAFVN (SEQ ID NO: 10) peptide for 24 hours and then harvested for dual luciferase assays (Promega) as described above.

U2OS cells were transiently transfected in 2 well chamber slides (Nunc) with CMV GFP-FoxM1B expression constructs in the presence or absence of either CMV WT T7-p19$^{ARF}$, CMV HA-p19$^{ARF}$, or CMV expression constructs containing either N-terminal mutant T7-p19$^{ARF}$ proteins (Δ1-14, Δ15-25, or Δ26-37) or V5-TAT-p19$^{ARF}$ proteins (26-44; SEQ ID NO: 11, or 26-55; SEQ ID NO: 12). U2OS cells were transiently transfected with CMV EGFP expression vector containing the TAT-p19$^{ARF}$ proteins (26-44; SEQ ID NO: 11, or 26-55; SEQ ID NO: 12). Forty-eight hours post transfection, cells were fixed in 4% Para-formaldehyde for 20 minutes at room temperature. GFP fluorescence or immunofluorescence with anti-HA antibody following TRITC conjugated secondary antibody was detected using a Zeiss microscope. U2OS cells were treated with 12 μM of the rrrrrrrrrKFVRSRRPRTASCALAFVN (SEQ ID NO: 10) peptide for 24 hours and then analyzed for TRITC fluorescence as described above.

Example 17

Creation of Doxycycline Inducible CMV-TETO GFP-FoxM1B U2OS Cell Line and Soft Agar Assays The T-REx™-U2OS cells were purchased from Invitrogen Life Technologies (Catalog No. R712-07). The T-REx™-U2OS cells express the Tet repressor from pCEP4/tetR that was episomally maintained in tissue culture medium containing 10% fetal calf serum and drug selection with 50 μg/ml of Hygromycin B. Tetracycline regulation in the T-REx System was based on the binding of tetracycline to the TET repressor and de-repressing of the CMV-TETO promoter controlling expression of the gene of interest (Yao et al., 1998, *Hum Gene Ther* 9:1939-1950). The pcDNA4-TO GFP-FoxM1B expression plasmid provided in the T-REx™ system was generated as described previously (Major et al., 2004, *Mol. Cell. Biol.* 24:2649-2661) and transfected T-REx™-U2OS cells with linearized pcDNA4-TO GFP-Foxm1b expression plasmid to select clonal Doxycycline inducible GFP-Foxm1b U2OS cell lines. CMV-TETO GFP-FoxM1B U2OS clones were isolated by selection for three weeks with tissue culture medium containing 50 μg/ml of Hygromycin B and 250 μg/ml of Zeocin. The CMV-TETO GFP-Foxm1b U2OS clone C3 cell line was selected for the soft agar assays because it exhibited intermediate expression of the GFP-Foxm1b fusion protein in response to 1 μg/ml of Doxycycline (Sigma D-9891) as determined by Western blot analysis with GFP monoclonal antibody. Wild type U2OS cells or CMV-TETO GFP-Foxm1b U2OS clone C3 cells were grown in medium with or without 1 µg/ml of Doxycycline for 2 days prior to either adding the (D-Arg)$_9$-p19$^{ARF}$ 26-44 peptide or left untreated. A concentration of 12 µM of p19$^{ARF}$ peptide (rrrrrrrrrKFVRSR-RPRTASCALAFVN; SEQ ID NO: 10) was added to the cells for 24 hours prior to splitting the cells for the soft agar assays using procedures described previously (Conzen et al. 2000, Mol Cell Biol 20:6008-6018). U2OS cells (10$^5$) were plated subconfluently in a 6 well plates in 0.7% agarose on a 1.4% agarose bed in the presence or absence of 12 µM of the (D-Arg)$_9$-p19$^{ARF}$ 26-44 peptide and 1 µg/ml of Doxycycline. Every 4 days the tissue culture medium containing 10% fetal calf serum, 12 µM of the (D-Arg)$_9$-p19$^{ARF}$ 26-44 peptide and 1 µg/ml of Doxycycline was replaced. Controls included growth in medium containing 10% fetal calf serum with or without 1 µg/ml of Doxycycline. U2OS cell colonies that were larger than 1 mm in size were scored after two weeks of growth on the soft agar.

Example 18

The p19$^{ARF}$ 26 to 44 Sequences are Sufficient to Associate with and Inhibit FoxM1B Transcriptional Activity To identify p19$^{ARF}$ protein sequences essential for association with FoxM1B protein, Co-IP assays were performed with protein extracts prepared from transiently transfected U2OS cells, which lack endogenous expression of the p19$^{ARF}$ tumor suppressor protein (Martelli et al., 2001, Proc Natl Acad Sci USA 98:4455-4460). U2OS cells were co-transfected with CMV Green Fluorescent Protein (GFP)-FoxM1B expression vector and CMV expression plasmids containing either WT p19$^{ARF}$ protein or N-terminal deletion mutants of the p19$^{ARF}$ protein (Δ1-14, Δ15-25, Δ26-37, or Δ26-37+Δ1-14) that were fused to the HA epitope tag (Weber et al., 2000, Mol Cell Biol 20:2517-2528). Protein extracts were incubated with HA antibody to immunoprecipitate (IP) the HA-p19$^{ARF}$ protein followed by Western blot analysis with a monoclonal antibody specific to GFP protein to detect the GFP-FoxM1B fusion protein. These Co-IP experiments demonstrated that the N-terminal 25 amino acid residues of the p19$^{ARF}$ (p19) protein were dispensable for association with the GFP-FoxM1B protein (FIG. 15C-D). In contrast, the p19 amino acid residues 26 to 37 were essential for association with the GFP-Foxm1b fusion protein (FIG. 15C-D). Furthermore, retention of the C-terminal 60 amino acids from the FoxM1B protein (688-748) was required for p19 protein binding (FIG. 15C-D).

To identify p19 protein sequences that are sufficient for association with FoxM1B protein, Co-IP assays were performed with protein extracts prepared from U2OS cells that were transiently transfected with CMV GFP-FoxM1B expression plasmid and the CMV expression vector containing the V5 epitope tagged p19$^{ARF}$ 26-44 or p19$^{ARF}$ 26-55 sequences. At the amino terminus of either the p19$^{ARF}$ sequences 26 to 44 or 26 to 55, we placed the protein transduction/nuclear localization domain (MGYGRKKRRQRRR; SEQ ID NO: 13) from the HIV-TAT protein (Becker-Hapak et al., 2001, Methods 24:247-256). Protein extracts were incubated with the V5 epitope tag antibody to IP the p19 protein followed by Western blot analysis with GFP monoclonal antibody to detect the GFP-FoxM1B fusion protein. These Co-IP experiments demonstrated that p19 amino acid residues 26-44 were sufficient to associate with the FoxM1B protein (FIG. 15E).

To determine whether formation of the p19-FoxM1B protein complex could effectively inhibit FoxM1B transcriptional activity, U2OS cells were transiently transfected with the 6×Foxm1b-TATA-luciferase reporter plasmid (Rausa et al., 2003, Mol. Cell. Biol. 23:437-449; Major et al., 2004, Mol. Cell. Biol. 24:2649-2661) and the CMV WT FoxM1B and p19 expression vectors (FIG. 15F). These cotransfection assays demonstrated that both WT p19 and mutant T7-p19$^{ARF}$Δ1-14, T7-p19$^{ARF}$Δ15-25, V5-TAT-p19$^{ARF}$ 26-44 and V5-TAT-p19$^{ARF}$ 26-55 proteins that retained their ability to associate with FoxM1B protein (FIG. 15D-E) were able to significantly decrease FoxM1B transcriptional activity (FIG. 15F). In contrast, the T7-p19$^{ARF}$Δ26-37 proteins, which no longer associated with the FoxM1B protein (FIG. 15D) were unable to significantly reduce FoxM1B transcriptional activity in these cotransfection assays (FIG. 15F). Interestingly, deletion of the FoxM1B C-terminal sequences required for association with p19 protein (FIG. 15D; Foxm1b 1-688) was also found to be essential for FoxM1B transcriptional activity (FIG. 15F). These studies demonstrated that FoxM1B transcription factor was a novel inhibitory target for the p19$^{ARF}$ tumor suppressor, a finding consistent with the important role of FoxM1B in proliferative expansion during liver tumor progression.

Example 19

The p19$^{ARF}$ Tumor Suppressor Targets FoxM1B Protein to the Nucleolus

U2OS cell cotransfection studies demonstrated that HA tagged p19 was able to target GFP-FoxM1B fusion protein to the nucleolus (FIG. 16A-C). While GFP-FoxM1B 1-748 full-length protein exhibited nuclear staining (FIG. 16D), nucleolar targeting of GFP-FoxM1B fusion protein was found in cotransfections with expression vectors containing either WT p19 or mutant p19 proteins that were still able to associate with FoxM1B protein (FIG. 16E-F). The GFP-FoxM1B protein was targeted to the nucleolus by expression vectors containing either the V5-TAT-p19$^{ARF}$ 26-44 or V5-TAT-p19$^{ARF}$ 26-55 sequences (FIG. 16G-H) and these p19 sequences were also localized to the nucleolus (FIG. 16I). In contrast, nuclear fluorescence was found with the GFP-FoxM1B WT protein that was transfected with the CMV p19$^{ARF}$Δ26-37 mutant that failed to associate with FoxM1B protein (FIG. 16J). Likewise, cotransfection assays with the CMV WT p19 and CMV GFP-FoxM1B 1-688 expression vectors showed nuclear fluorescence of the mutant GFP-Foxm1b 1-688 protein, a finding consistent with this FoxM1B mutant's inability to associate with the p19 protein (FIGS. 16K and 15B). These studies suggested that association between the p19 tumor suppressor and FoxM1B resulted in targeting FoxM1B to the nucleolus and FoxM1B transcriptional inhibition.

Example 20

(D-Arg)$_9$ p19$^{ARF}$ 26 to 44 Peptide Significantly Reduces Both FoxM1B Transcriptional Activity and Foxm1b Induced Cell Colony Formation on Soft Agar The p19$^{ARF}$ 26-44 peptide containing nine D-Arg residues (SEQ ID NO: 14) at the N-terminus was fluorescently tagged with Lissamine (TRITC) on the N-terminus and acetylated at the C-terminus as described above. Treatment of U2OS cells with 12 of the (D-Arg)$_9$-p19$^{ARF}$ 26-44 peptide (rrrrrrrrrK-FVRSRRPRTASCALAFVN; SEQ ID NO: 10) for three days demonstrated that this (D-Arg)$_9$-p19$^{ARF}$ 26-44 peptide was efficiently transduced into all of the cells and that its fluorescence localized to the nucleolus (FIG. 16L). Furthermore, exposure of U2OS cells with 12 µM of the (D-Arg)$_9$-p19$^{ARF}$ 26-44 peptide for five days caused neither toxicity nor any increases in apoptosis. Furthermore, treatment of U2OS cells with 12 µM of the (D-Arg)$_9$-p19$^{ARF}$ 26-44 peptide that were transfected with CMV-FoxM1B expression vector and the 6×FoxM1B-TATA-luciferase plasmid resulted in significant reduction in FoxM1B transcriptional activity (FIG. 17A), suggesting that this p19$^{ARF}$ peptide was an effective inhibitor of FoxM1B transcriptional activity.

In addition, the tetracycline (TET) regulated T-REx™ System described above was used to conditionally express the GFP-FoxM1B protein in U2OS cells to determine whether conditional overexpression of FoxM1B protein could enhance anchorage-independent growth of U2OS cells. The CMV-TETO GFP-FoxM1B expression plasmid was transfected into T-REx™-U2OS cells (containing TET repressor) and clonal U2OS cell lines were selected that were Doxycycline-inducible for GFP-FoxM1B expression. In response to Doxycycline treatment, the CMV-TETO GFP-FoxM1B U2OS clone C3 cell line displayed inducible intermediate levels of the GFP-FoxM1B fusion protein (FIG. 17B). The U2OS clone C3 cell line was selected to examine whether doxycycline induced FoxM1B-GFP expression enhanced anchorage-independent growth as assessed by propagation for two weeks on soft agar (Conzen et al., 2000, *Mol Cell Biol* 20:6008-6018). The soft agar experiments demonstrated that induced expression of GFP-FoxM1B protein caused a significant increase in anchorage-independent growth as evidenced by increasing the number and size of U2OS cell colonies on soft agar (FIGS. 17G and I) compared to uninduced controls (FIG. 17F) or the WT U2OS cells (FIG. 17C-D).

The results suggested that the FoxM1B protein displayed oncogenic properties by stimulating anchorage-independent growth of U2OS cell colonies on soft agar. In order to determine whether the (D-Arg)$_9$-p19$^{ARF}$ 26-44 peptide inhibited FoxM1B induced colony formation of U2OS cells on soft agar, the Doxycycline induced U2OS clone 3 cells were treated with 12 µM of the (D-Arg)$_9$-p19$^{ARF}$ 26-44 peptide one day prior to plating and was added at this concentration of (D-Arg)$_9$-p19$^{ARF}$ 26-44 peptide in the soft agar and growth medium throughout the duration of the experiment as described above. The results of these soft agar studies demonstrated that the (D-Arg)$_9$-p19$^{ARF}$ 26-44 peptide significantly diminished the ability of induced GFP-FoxM1B to stimulate colony formation of the U2OS clone C3 cells on soft agar (FIGS. 17H and I). Furthermore, the (D-Arg)$_9$-p19$^{ARF}$ 26-44 peptide significantly diminished the ability of the parental U2OS cells to form colonies on soft agar (FIGS. 17E and I). Taken together these studies suggested that the (D-Arg)$_9$-p19$^{ARF}$ 26-44 peptide is an effective inhibitor of both FoxM1B mediated transcriptional activation and FoxM1B induced stimulation in anchorage-independent growth that is required for cellular transformation.

Example 21

WT-Blocked p19$^{ARF}$ 26-44 Peptide Induced Apoptosis More Significantly than WT-Unblocked and Mutant-Blocked p19$^{ARF}$ 26-44 Peptide Activity as Shown by TUNEL Assay Wildtype-blocked ("WT-blocked") (D-Arg)$_9$-p19$^{ARF}$ 26-44 peptides, wildtype-unblocked ("WT-unblocked") (D-Arg)$_9$-p19$^{ARF}$ 26-44 peptides and mutant blocked (D-Arg)$_9$-p19$^{ARF}$ 26-44 peptides were prepared under good laboratory practice ("GLP") conditions and received from Genemed Synthesis, Inc. (San Antonio, Tex.). Terminals of the WT-blocked and mutant-blocked peptide were blocked by acetylation on N-terminus and by amidation on C-terminus.

TUNEL assay was used to measure apoptosis in S2 cells treated with WT-blocked, mutant-blocked or WT-unblocked (D-Arg)$_9$-p19$^{ARF}$ 26-44 peptides. (D-Arg)$_9$-p19$^{ARF}$ 26-44 peptide treatment of cells was performed in 8-well chamber slides for TUNEL staining. On Day 0, 20,000 cells per well were seeded in the 8-well chamber slides. On Day 1, slides were replenished with fresh media containing one of the following concentrations of either WT-blocked, mutant-blocked or WT-unblocked (D-Arg)$_9$-p19$^{ARF}$ 26-44 peptides: 10, 15, 25, 30, 40 and 70 µM for 24 hours. On Day 2, TUNEL staining was performed following the manufacture's protocol (ApopTag® Fluorescein In Situ Apoptosis Detection Kit from CHEMICON® International, S7110). The percent of apoptosis of S2 cells (±SD) was measured by counting the number of TUNEL-positive cells (green fluorescence) per 1,000 nuclei as visualized by DAPI (blue fluorescence) counterstaining. The experiment was repeated in a second experiment using the same protocol. Statistical analysis and EC$_{50}$ calculation were performed using GraphPad Prism software.

The results demonstrated that WT-blocked (D-Arg)$_9$-p19$^{ARF}$ 26-44 peptides induced significantly higher apoptosis compared to WT-unblocked and mutant-blocked (D-Arg)$_9$-p19$^{ARF}$ 26-44 peptides. (FIGS. 18A and 18B, Tables 3 and 4). WT-unblocked (D-Arg)$_9$-p19$^{ARF}$ 26-44 peptides showed some activity compared to the mutant-blocked peptide at doses higher than 30 µM (statistically significant at 30 and 40 µM) in Experiment #1 only. (FIG. 18A, Table 3). There was reproducibility of the apoptotic effect of WT-blocked peptide between the two experiments in the TUNEL assay (EC$_{50}$ for blocked ARF peptide were 30.08 µM and 30.73 µM for Feb. 15, 2012 and Apr. 11, 2012, respectively) (FIGS. 19A and 19B).

TABLE 3

% of TUNEL Positive S2 Cells after Treatment with WT-Blocked, WT-Unblocked and Mutant (D-Arg)$_9$-p19$^{ARF}$ 26-44 Peptides - Experiment 1

| Concentration | WT Blocked | | | Mutant Blocked | | WT Unblocked | | |
|---|---|---|---|---|---|---|---|---|
| µM/Well | Mean | SD | P | Mean | SD | Mean | SD | P |
| 40 | 98.48 | 3.03 | <0.05* | 8.01 | 7.43 | 19.94 | 4.34 | <0.05** |
| 30 | 57.78 | 34.22 | <0.05* | 0 | 0 | 5.59 | 2.1 | <0.05** |
| 25 | 20.27 | 14.04 | <0.05* | 1.18 | 1.42 | 1.27 | 1 | |
| 10 | 0.46 | 0.54 | | 0.2 | 0.39 | 2.46 | 3.29 | |

*when compared with mutant-blocked and WT-unblocked
**when compared with mutant-blocked

TABLE 4

% of TUNEL Positive S2 Cells after Treatment with WT-Blocked, WT-Unblocked and Mutant (D-Arg)$_9$-p19$^{ARF}$ 26-44 Peptides - Experiment 2

| Concentration µM/Well | WT Blocked | | | Mutant Blocked | | WT Unblocked | | |
|---|---|---|---|---|---|---|---|---|
| | Mean | SD | P | Mean | SD | Mean | SD | P |
| 70 | N/A | N/A | | 41.64 | 11.18 | 30.34 | 13.34 | |
| 40 | 70.17 | 10.27 | <0.05* | 28.08 | 16.72 | 20.51 | 2.75 | |
| 30 | 47.52 | 7.03 | | N/A | N/A | N/A | N/A | |
| 25 | 39.48 | 12.35 | <0.05* | 18.51 | 5.42 | 11.19 | 1.68 | <0.05** |
| 15 | 13.6 | 3.75 | <0.05*** | 17.31 | 7.74 | 7.56 | 1.33 | <0.05** |
| 10 | 12.91 | 3.27 | <0.05*** | 9.42 | 4.24 | 6.79 | 2.22 | |

*when compared with mutant-blocked and WT-unblocked
**when compared with mutant-blocked
***when compared with WT-unblocked
N/A—Not tested Example 22

ARF-Peptide Preferentially Eliminated Liver Cancer Stem Cells (LCSCs)

ALb-HRasV12 mice were used to demonstrate that ARF peptides as provided herein were capable of preferentially eliminating liver cancer stem cells (LCSCs). ALb-HRasV12 mice are a transgenic strain that expresses activated Ras in the liver. These mice developed hepatocellular carcinoma (HCC) by 9 months of age. Alb-HRasV12 mice at 9 months of age were injected with either PBS, mutant peptide or ARF-peptide (3 animals per group) at 5 mg/kg every day for a period of 3 weeks. The mice were then sacrificed one week later and HCC nodules were quantified (FIGS. 20A and 20B). In addition, single cell suspensions from the 8 different tumor nodules from the three treatment groups were assayed for CD90$^+$/CD45$^-$ cells by fluorescence-activated cell sorting (FACS). As shown in FIG. 20C, there was a considerable reduction in the number of the CD90$^+$/CD45− cells in the ARF-peptide injected samples suggesting that the ARF peptide preferentially eliminates liver cancer stem cells.

Example 23 p53 Null Thymic Lymphoma and Sarcoma Cells Required FoxM1 for Survival

To investigate the effect of FoxM1 depletion in p53 loss-of-function tumors, a strain of triple transgenic mice harboring CreERT2, Foxm1 fl/fl and p53−/− alleles were generated by crossing the three individual strains. The CreERT2 strain (Strain 01XAB) was obtained from Tyler Jacks' laboratory (Massachusetts Institute of Technology, USA). Foxm1b fl/fl strain was generated as previously described (Wang et al., 2002, Proc Natl Acad Sci USA, 99: 16881-16886). The C57Bl/6 p53+/− strain was obtained from the Jackson Laboratories (Bar Harbor, Me.).

Triple transgenic mice developed a spectrum of spontaneous tumors, consistent with their p53 null background (Donehower et al., 1992, Nature 356: 215-221.) The presence of CreERT2 allele in the triple transgenic strain permitted Cre recombinase expression upon 4-OH tamoxifen treatment to excise flox flanked Foxm1 alleles and thus silenced FoxM1 expression. However, attempts to study the effects of Foxm1 deletion on endogenous lymphomas/sarcomas were inconclusive mainly because the lymphomas/sarcomas developed at different times in the cohorts of mice used. Also, since the Foxm1 alleles were deleted in most cell types in this system, it was difficult to avoid the effects of Foxm1-deletion in the other cell types on the lymphoma/sarcoma development and progression. Therefore, lymphoma/sarcoma cells were isolated from the triple transgenic and analyzed in host mice. Two thymic lymphoma (L1 and L2) and a sarcoma (S) triple transgenic cell lines were generated from endogenous tumors. In addition, a control thymic lymphoma line (C) isolated from Foxm1 fl/fl p53−/− tumor was established in parallel. Specifically, thymic lymphoma tissue was isolated from the thymus of mice and sarcoma was isolated from a tumor encompassing the rear leg of the mouse. Tumors were excised, minced and enzymatically dissociated with 0.25% trypsin or papain (10 µl/ml). Cells were then washed and replaced with fresh media. Thymic lymphoma cells grew in suspension and sarcoma cells were adherent and maintained in DMEM medium supplemented with 10% fetal bovine, L-glutamine and penicillin-streptomycin.

Figure 21:
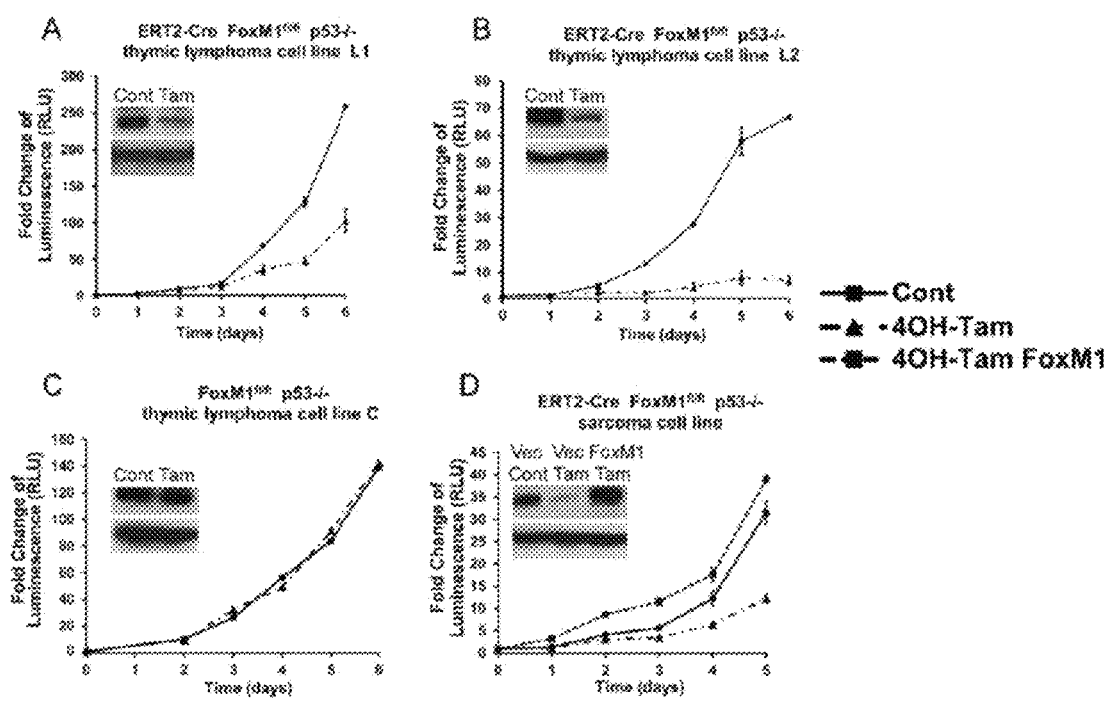

The deletion efficiency of FoxM1 was tested by immunoblot and confirmed that FoxM1 expression was significantly reduced in triple transgenic lines L1, L2 and S but not in control line C upon treatments with 4-OH tamoxifen (FIGS. 21A-D). A sarcoma line stably transduced with exogenous FoxM1 expression was also generated, and treatment with 4-OH tamoxifen did not diminish exogenous FoxM1 expression in those cells (FIG. 21D).

To examine the effect of FoxM1 ablation, growth curves were plotted following 4-OH tamoxifen treatment. Cells were counted and seeded at a density of 2×10$^3$ cells per well in triplicate in 48-well plate (Corning). Cell growth was monitored by measuring the luminescent signal using the CellTiter-Glo kit (Promega) following the manufacturer's protocol. FoxM1 deletion led to a profound decrease in the cell viability starting from an early time point in all of the three triple transgenic lines L1, L2 and S (FIGS. 21A, 21B and 21D). The control lymphoma cell line C (FIG. 21C) as well as the sarcoma cells stably expressing the exogenous FoxM1 (FIG. 21D) did not exhibit inhibition, demonstrating that the phenotype was caused by FoxM1 ablation.

Tumorigenic properties of the sarcoma cells were tested by performing soft agar assay. For soft agar assay, cells were counted and plated in six-well plates in 0.35% agarose on a 0.7% agarose bed in triplicate for 2 weeks. For foci formation assay, one thousand cells were plated in six-well plates for 2 weeks. In both assays, colonies were stained with crystal violet and counted after 3 weeks. Photographs of these colonies were taken using a dissecting microscope.

FoxM1 deletion significantly reduced the ability of cells to grow under anchorage-independent conditions (FIG. 27A). Cells after FoxM1 deletion formed about 60% less colonies on soft agar plate compared to control cells. In addition, cells without FoxM1 also formed about 50% less colonies on adherent plate (FIG. 27B).

These results indicated that FoxM1 function was important for the survival and tumorigenicity of tumor cells with p53 loss of function.

Example 24

FoxM1 Ablation Diminished Expression of Survivin and Bmi1 in p53 Null Tumors Accompanied by Apoptosis To validate a strategy of targeting FoxM1 in tumors harboring p53 loss of function for the treatment of cancer, a nude mice allograft model was utilized, using nu/nu nude mice obtained from Charles River Laboratories (Wilmington, Mass.).

In these experiments, one million thymic lymphoma (L1) or sarcoma (S) triple transgenic cells were injected subcutaneously into the rear flank of each nude mouse. About one week after injection, when the tumors became palpable, animals were randomized into two treatment groups and intraperitoneally administered either tamoxifen (1 mg/per injection) or corn oil (vehicle) every other day for two weeks. Tumor sizes were measured thereafter with calipers and calculated as one-half (length×height×width).

For both p53 null tumor lines, tumors in the vehicle-treated control group grew significantly faster than of the tumors treated with tamoxifen (FIGS. 22A and B). FoxM1 expression in these tumors was examined by performing immunohistochemical staining. The following antibodies were used: FoxM1 (Santa Cruz: sc-500), Survivin (Novus Biologicals: NB500-201), α-tubulin (Sigma: T6074), Cleaved-PARP (Asp214) (Cell Signaling: #9544), Bmi1 (Cell Signaling; #5856), and Cleaved Caspase-3 (Asp175) (Cell Signaling #9661). Horseradish peroxidase-conjugated secondary antibodies (Bio-rad) were used to amplify the signal from primary antibody binding. Protein lysates were prepared in NP-40 lysis buffer consisted of 1% NP-40, 5% glycerol, 20 nM (3-glycerophosphate, 2 mM NaF, 5 mM EDTA, 5 mM EGTA and freshly added protease inhibitor cocktail (Roche).

FoxM1 expression was significantly reduced following two-weeks of tamoxifen treatment, while in the vehicle-treated group abundant FoxM1 staining was detected, consistent with FoxM1 over-expression in tumor cells (FIG. 28A-28D).

To investigate the basis for delayed tumor growth, apoptosis of the tumor cells was assayed using TUNEL staining. In both lymphoma- and sarcoma-derived tumor sections, an increased number of apoptotic cells were observed following FoxM1 depletion as evidenced by an increased number of TUNEL positive cells (FIG. 22C-D, FIG. 28E-28L). Cleaved caspase-3 and cleaved PARP, two apoptosis markers, were assayed, and significant increases in the number of cleaved caspase-3 and cleaved PARP positive cells were detected in FoxM1-depleted cells (FIG. 28M-28N). These observations suggested that inhibition of p53−/− tumors following loss of FoxM1 resulted from enhanced tumor cell apoptosis. Increased apoptosis upon FoxM1-depletion was unexpected because p53−/− tumor cells are generally resistant to apoptosis (Lopes et al., 1997, *J Biol Chem.* 272: 12893-12896). Survivin, which belongs to the inhibitor of apoptosis protein (IAP) family, is a known transcriptional target of FoxM1 that plays important roles in both cell cycle regulation and inhibition of apoptosis (Wang et al., 2005, *Mol Cell Biol*, 25: 10875-10894; Altieri, D. C., 2003, *Oncogene*, 22: 8581-8589). Expression of Survivin, which is abundant in control groups for both p53 null lymphoma and sarcoma, was down-regulated following depletion of FoxM1 (FIG. 23A-D, I), consistent with reduced Survivin levels to contribute to apoptosis of HCC cells (Gusarova et al., 2007, *J Clin Invest*, 117: 99-111). Bmi1, another FoxM1-induced gene (Wang et al., 2010, *Cancer Res.* 71: 4292-4302; Li et al., 2008, *J Biol Chem.* 283: 16545-16553), was assayed in the tumor sections, and expression of Bmi1 was largely diminished in FoxM1-ablated tumors (FIG. 23E-H, I), consistent with the capacity to protect tumor cells from apoptotic stimuli (Jacobs et al., 1999, *Genes Dev*, 13: 2678-2690). These observations suggested roles for Bmi1 and Survivin in the survival of the p53−/− lymphoma and sarcoma.

Example 25

ARF-Derived Peptide Inhibitor of FoxM1 Induced Apoptosis in p53 Null Tumor Cells A peptide (ARF 26-44) derived from the mouse tumor suppressor ARF has been described that inhibits the activity of FoxM1 by re-localizing it to the nucleolus (Kalinichenko et al., 2004, *Genes Dev*, 18: 830-850; Gusarova, G. A., et al., 2007, *J Clin Invest*, 117: 99-111). A cell-penetrating form of the peptide efficiently targets FoxM1 in liver tumors (U.S. Pat. No. 8,029,980) Moreover, using the DEN/PB induced mouse hepatocellular carcinoma model, the ARF-peptide was able to inhibit HCC progression by inducing apoptosis (Gusarova et al., 2007, *J Clin Invest*, 117: 99-111), and to block the metastatic growth of the HCC cells (Park et al., 2011, *EMBO Mol Med*, 3: 21-34).

These experiments were performed to determine if modifying the termini conferred any advantages on these peptides when administered to an animal. Both wild type ARF 26-44 (rrrrrrrrrKFVRSRRPRTASCALAFVN) (SEQ ID NO 10) and mutant ARF 37-44 (rrrrrrrrrSCALAFVN) (SEQ ID NO 21) peptides were synthesized by Genemed Synthesis Inc. (San Antonio, Tex.). The N-terminus of each peptide was fused with nine D-Arg(r) residues. Both wild type and mutant peptides were blocked with amidation on C-terminus and acetylation on N-terminus. For sarcoma cells, mice were treated with 5 mg/kg body weight of peptide every other day for 10 times. For lymphoma cells, mice were treated with 2.5 mg/kg body weight of peptide every other day for 10 times.

Figure 29:
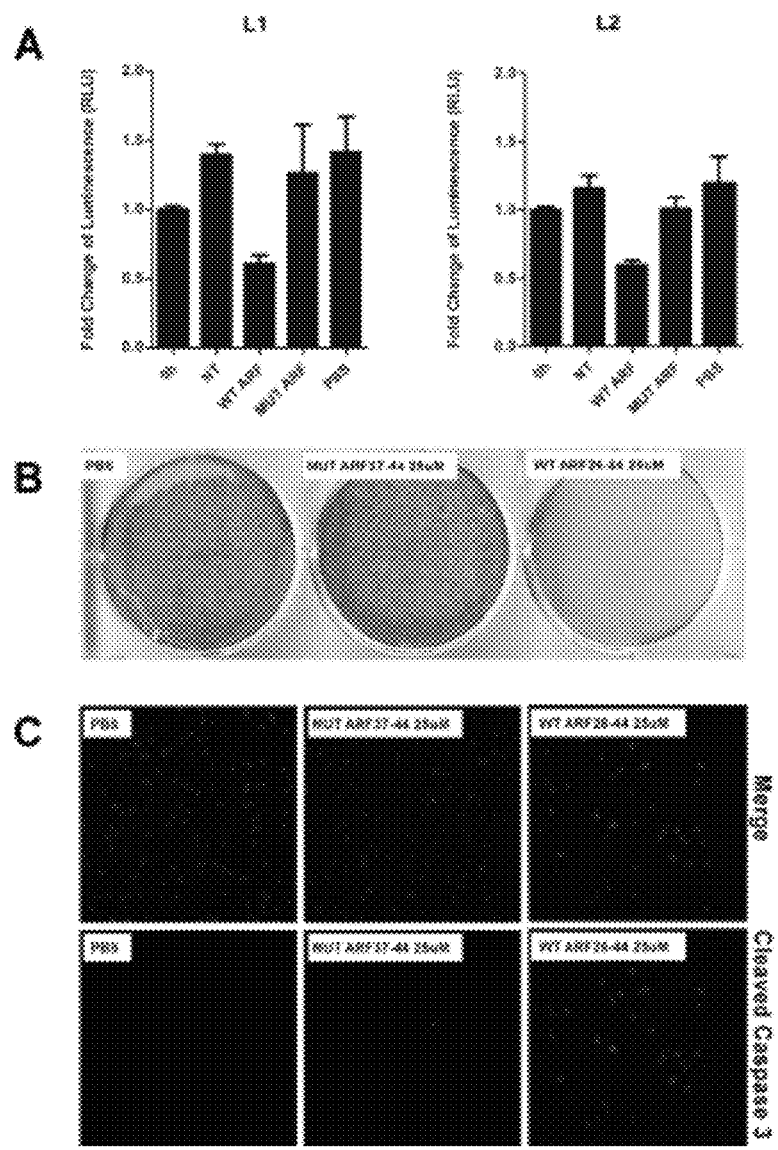

In order to determine whether the ARF-peptide was able to inhibit the p53 null tumors, the effect of the peptide was examined in vitro. The mutant peptide (ARF 37-44), which lacked the interacting domain with FoxM1, was used as a control. One day after treatment the wild type ARF-peptide treated p53 null thymic lymphoma cell lines L1 and L2 underwent apoptosis. The number of viable cells was much less following treatment with wild type ARF peptide compared with cells treated with the mutant-peptide or PBS (FIG. 24A). Induction of apoptosis by the wild type peptide was demonstrated by TUNEL staining (FIG. 24B). A similar effect was observed in p53 null sarcoma cells (FIG. 24A-B). However, compared to the sarcoma lines, the p53−/− lymphoma cells were more sensitive to the ARF-peptide, where 5 µM of peptide was able to cause significant apoptosis (FIG. 24A). Cell growth and foci formation assay, as well as cleaved caspase-3 staining were performed to confirm the finding (FIG. 29).

Example 26

ARF-Peptide Effectively Reduces the Colonization of p53 Null Tumor Cells In Vivo To test the therapeutic effect of the ARF-peptide on p53 null tumors in vivo, p53 null lymphoma/sarcoma cells were introduced into the circulation of SCID mice through intravenous injection. ICR SCID mice were obtained from Taconic Farms (Germantown, N.Y.). Both p53 null sarcoma and lymphoma cells were stably transduced before injection with lentivirus carrying a gene conferring luciferase expression. Specifically, cells were stably transduced with pFU-L2G luciferase construct obtained from Sanjiv Sam Gambhir (M. D., Ph.D) of Stanford University as optimized by Dr.

Huiping Liu (Liu et al., *Proc Natl Acad Sci USA*, 107: 18115-18120). This construct enabled expression of both the bioluminescence and green fluorescence protein. eGFP positive cells were sorted by Beckman Coulter MoFlo. 3×10⁶ cells were suspended in cold PBS and injected through the tail vein of SCID mice. Live animal imaging was performed using an IVIS Spectrum optical imaging machine (Caliper Life Sciences, Alameda, Calif.). Shortly after injection, comparable fluorescence was detectable in the lung by injecting luciferin using Xenogen IVIS spectrum in vivo imaging machine (FIGS. 25A and D). Mice were randomized into three groups and were treated with PBS, mutant-peptide or the wild type ARF-peptide for 10 injections every other day by intraperitoneal injection. Ten days after tumor inoculation, p53 null sarcoma cells were found to colonize the lung (FIG. 25C). After 20 days following the initial inoculation, compared to the PBS and the mutant peptide treated mice, the amount of luciferase signal from the wild type ARF-peptide treated mice was significantly reduced. The mice were sacrificed and lung sections were analyzed for tumor colonies. Consistent with the fluorescence signal, fewer tumors were observed on the surface of the lungs of mice treated with the wild type ARF peptide (FIG. 25B). A reduced number of tumor colonies that were larger than 100 μm×100 μm were detected in the lungs of the wild type ARF peptide treated mice (FIG. 25C). For the p53 null thymic lymphoma cells, metastatic growth in kidney was observed, consistent with murine thymic lymphoma cells having a tendency to colonize kidney, liver and spleen (Aoudjit et al., 1998, *Blood*, 91: 623-629). Around 20 days after inoculation, mice treated with PBS and the mutant ARF peptide displayed strong luciferase signals from colonized lymphoma cells in the lower back region. On the other hand, wild type ARF-peptide treated mice emitted very little fluorescence, indicating inhibition of colonized tumors. When the mice were sacrificed, large tumor masses were found in the kidney by microscopic examination in the PBS and in the mutant peptide treated mice. Atypical pale coloration and enlargement of the kidney were observed in these mice, and these mice carried a large tumor mass that encompassed the two kidneys, the connective tissues and the spinal cords. In contrast, kidneys from the wild-type peptide-treated mice retained their original size and structure, with only a small white mass beginning to build up on the surface of the kidney (FIGS. 25E and F). These results indicated that wild type ARF-peptide was able to efficiently block renal metastasis of the p53 null thymic lymphoma.

It should be understood that the foregoing disclosure emphasizes certain specific embodiments of the invention and that all modifications or alternatives equivalent thereto are within the spirit and scope of the invention as set forth in the appended claims.

TABLE 5

Select Amino Acid Sequences

| SEQ ID NO. | DESCRIPTION | AMINO ACID SEQUENCE |
|---|---|---|
| 15 | Full length mouse p19Arf | MGRRFLVTVRIQRAGRPLQERVFLVKFVRSRRPRTASCAL AFVNMLLRLERILRRGPHRNPGPGDDDGQRSRSSSSAQLR CRFELRGPHYLLPPGDRRSAGRLPGHAGGAARVRGSAGCA RCLGSPAARLGPRAGTSRHRAIFAFRWVLFVFRWVVFVYR WERRPDRRA |
| 16 | p19Arf 26-44 | KFVRSRRPRTASCALAFVN |
| 17 | HIV Tat protein transduction/nuclear localization domain | MGYGRKKRRQRRR |
| 18 | 9 D-Arg | RRRRRRRRR |
| 19 | 9 D-Arg- p19Arf 26-44 with modifications at the N and C termini | (MOD)-RRRRRRRRRKFVRSRRPRTASCALAFVN-(MOD) |
| 20 | Full length human p19Arf | MVRRFLVTLRIRRACGPPRVRVFVVHIPRLTGEWAAPGAPAA VALVLMLLRSQRLGQPLPRRPGHDDGQRPSGGAAAAPRRGA QLRRPRHSHPTRARRCPGGLPGHAGGAAPGRGAAGRARCLG PSARGPG |

We claim:

1. A method of eliminating a liver cancer stem cell comprising the step of contacting the liver cancer stem cell with a polypeptide comprising (1) a p19Arf peptide fragment comprising amino acid residues KFVRSRRRPTASCALAFVN (SEQ ID NO: 16), and (2) an HIV Tat peptide of SEQ ID NO:17 or a nine-D-Arg peptide of SEQ ID NO:18 that is covalently linked to the N-terminus of the p19Arf peptide fragment, wherein the polypeptide is modified at both the N terminus and the C terminus, wherein the N terminus is modified by acetylation and wherein the C terminus is modified by amidation.

2. The method of claim 1, wherein the modified polypeptide has the amino acid sequence of SEQ ID NO:19.

* * * * *